US011845994B2

(12) United States Patent
Velculescu et al.

(10) Patent No.: US 11,845,994 B2
(45) Date of Patent: Dec. 19, 2023

(54) RESPONSE TO EGFR BLOCKADE

(71) Applicants: The Johns Hopkins University, Baltimore, MD (US); University of Torino, Turin (IT)

(72) Inventors: Victor E. Velculescu, Dayton, MD (US); Eniko Papp, Baltimore, MD (US); Vilmos Adleff, Baltimore, MD (US); Andrea Bertotti, Turin (IT); Livio Trusolino, Turin (IT)

(73) Assignees: The Johns Hopkins University, Baltimore, MD (US); University of Torino, Turin (IT)

( * ) Notice: Subject to any disclaimer, the term of this patent is extended or adjusted under 35 U.S.C. 154(b) by 91 days.

(21) Appl. No.: 17/225,717

(22) Filed: Apr. 8, 2021

(65) Prior Publication Data

US 2021/0301352 A1    Sep. 30, 2021

Related U.S. Application Data

(62) Division of application No. 15/541,521, filed as application No. PCT/US2016/012268 on Jan. 6, 2016, now Pat. No. 10,982,287.

(60) Provisional application No. 62/100,110, filed on Jan. 6, 2015.

(51) Int. Cl.
| | |
|---|---|
| *C12Q 1/6886* | (2018.01) |
| *A61K 39/395* | (2006.01) |
| *C07K 16/28* | (2006.01) |
| *C12Q 1/68* | (2018.01) |
| *A61P 35/00* | (2006.01) |
| *A61K 39/00* | (2006.01) |

(52) U.S. Cl.
CPC .......... *C12Q 1/6886* (2013.01); *A61K 39/395* (2013.01); *A61P 35/00* (2018.01); *C07K 16/2863* (2013.01); *C12Q 1/68* (2013.01); *A61K 2039/505* (2013.01); *A61K 2039/55* (2013.01); *C07K 2317/24* (2013.01); *C07K 2317/76* (2013.01); *C12Q 2600/106* (2013.01); *C12Q 2600/156* (2013.01); *C12Q 2600/158* (2013.01)

(58) Field of Classification Search
CPC .................................................... C12Q 1/6886
USPC ...................................................... 424/133.1
See application file for complete search history.

(56) References Cited

U.S. PATENT DOCUMENTS

| | | | |
|---|---|---|---|
| 10,982,287 B2 | 4/2021 | Velculescu | |
| 2012/0294867 A1 | 11/2012 | Denis et al. | |
| 2018/0346987 A1 | 12/2018 | Velculescu | |

FOREIGN PATENT DOCUMENTS

WO    WO 2016/015788    2/2016

OTHER PUBLICATIONS

Zhang et al (J Pharmacol Sci, 2014, 77-83).*
Lin et al (Nature Genetics, 2014, 46(5): 467-473).*
Heist et al (Journal of Thoracic Oncology, 2012, 7(12): 1775-1780).*
Azuma et al (Oncotarget, 2014, 5(15): 5908-5919).*
Goke et al (Digestion, 2013, 88: 172-181).*
A. Algars, M. Lintunen, 0. Carpen, R. Ristamaki, J. Sundstrom, EGFR gene copy number assessment from areas with highest EGFR expression predicts response to antiEGFR therapy in colorectal cancer. Br J Cancer 105, 255 (Jul. 12, 2011).
A. Bardelli et al., Amplification of the MET receptor drives resistance to anti-EGFR therapies in colorectal cancer. Cancer discovery 3, 658 (Jun. 2013).
A. Bardelli et al., Mutational analysis of the tyrosine kinome in colorectal cancers. *Science* 300, 949 (May 9, 2003).
A. Bertotti et al., A molecularly annotated platform of patient-derived xenografts ("xenopatients") identifies HER2 as an effective therapeutic target in cetuximab resistant colorectal cancer. Cancer discovely 1, 508 (Nov. 2011).

(Continued)

*Primary Examiner* — Sean E Aeder
(74) *Attorney, Agent, or Firm* — Fish & Richardson P.C.

(57) ABSTRACT

Recent large-scale analyses have demonstrated that the genomic landscape of human cancer is complex and variable among individuals of the same tumor type. Such underlying genetic differences may in part be responsible for the varying therapeutic responses observed in cancer patients. To examine the effect of somatic genetic changes in colorectal cancer on sensitivity to a common targeted therapy, we performed complete exome sequence and copy number analyses of 129 tumors that were KRAS wild-type and analyzed their response to anti-EGFR antibody blockade in patient-derived tumorgraft models. In addition to previously identified genes, we detected mutations in ERBB2, EGFR, FGFR1, PDGFRA, and MAP2K1 as potential mechanisms of primary resistance to this therapy. Alterations in the ectodomain of EGFR were identified in patients with acquired resistance to EGFR blockade. Amplifications and sequence changes in the tyrosine kinase receptor adaptor gene IRS2 were identified in tumors with increased sensitivity to anti-EGFR therapy. Therapeutic resistance to EGFR blockade could be overcome in tumorgraft models through combinatorial therapies targeting actionable genes. These analyses provide a systematic approach to evaluate response to targeted therapies in human cancer, highlight additional mechanisms of responsiveness to anti-EGFR therapies, and provide additional avenues for intervention in the management of colorectal cancer.

2 Claims, 90 Drawing Sheets

(56) References Cited

OTHER PUBLICATIONS

A. K. Murugan, J. Dong, J. Xie, M. Xing, MEK1 mutations, but not ERK2 mutations, occur in melanomas and colon carcinomas, but none in thyroid carcinomas. Cell Cycle 8, 2122 (Jul. 1, 2009).
A. Pavlicek et al., Molecular predictors of sensitivity to the insulin-like growth factor 1 receptor inhibitor Figitumumab (CP-751,871). Mal Cancer Ther 12, 2929 (Dec. 2013).
A. Sartore-Bianchi et al., PIK3CA mutations in colorectal cancer are associated with clinical resistance to EGFR-targeted monoclonal antibodies. Cancer Res 69, 1851 (Mar. 1, 2009).
B.O. Van Emburgh, A. Sartore-Bianchi, F. Di Nicolantonio, S. Siena, A. Bardelli, Acquired resistance to EGFR-targeted therapies in colorectal cancer. Afol Oneal, (May 14, 2014).
Baker et al., Chromosome 17 deletions and p53 gene mutations m colorectal carcinomas. *Science* 244, 217 (Apr. 14, 1989).
C. Bettegowda et al., Detection of circulating tumor DNA in early- and late-stage human malignancies. Sci Transl ~Med 6, 224ra24 (Feb. 19, 2014).
C. Mao et al., BRAF V600E mutation and resistance to anti-EGFR monoclonal antibodies in patients with metastatic colorectal cancer: a meta-analysis. Molecular biology reports 38, 2219 (Apr. 2011).
C. Montagut et al., Identification of a mutation in the extracellular domain of the Epidermal Growth Factor Receptor conferring cetuximab resistance in colorectal cancer. Nat Afed 18, 221 (Feb. 2012).
C. S. Karapetis et al., K-ras mutations and benefit from cetuximab in advanced colorectal cancer. N Engl J Afed 359, 1757 (Oct. 23, 2008).
D. W. Parsons et al., Colorectal cancer: mutations in a signaling pathway. Nature 436, 792 (Aug. 11, 2005).
E. Baralis, A. Bertotti, A. Fiori, A. Grand, LAS: a software platform to support oncological data management. Journal of medical systems 36 Suppl 1, S81 (Nov. 2012).
E. Day et al., IRS2 is a candidate driver oncogene on 13q34 in colorectal cancer. International journal of experimental pathology 94, 203 (Jun. 2013).
E. Garralda et al., Integrated next-generation sequencing and avatar mouse models for personalized cancer treatment. Clin Cancer Res 20, 2476 (May 1, 2014).
E. Van Cutsem, A. Cervantes, B. Nordlinger, D. Arnold, E.G. W. G. on behalf of the, Metastatic colorectal cancer: ESMO Clinical Practice Guidelines for diagnosis, treatment and follow-up. Annals of oncology: official journal of the European Society for Medical Oncology I ESMO, (Sep. 4, 2014).
F. Goke et al., Fibroblast growth factor receptor 1 as a putative therapy target m colorectal cancer. Digestion 88, 172 (2013).
G. Joslyn et al., Identification of deletion mutations and three new genes at the familial polyposis locus. Cell 66, 601 (1991).
G. Perkins, C. Pilati, H. Blons, P. Laurent-Puig, Beyond KRAS status and response to anti-EGFR therapy in metastatic colorectal cancer. Pharmacogenomics 15, 1043 (May 2014).
Galimi et al., "Genetic and expression analysis of MET, MACC1, and HGF in metastatic colorectal cancer: response to met inhibition in patient xenografts and pathologic correlations," *Clin Cancer Res* 17, 3146 (May 15, 2011).
H. Davies et al., Mutations of the BRAF gene in human cancer. Nature, (Jun. 9, 2002).
H. Rajagopalan et al., Tumorigenesis: RAF/RAS oncogenes and mismatch-repair status. Nature 418, 934. (2002).
International Preliminary Report on Patentability and Written Opinion in International Application No. PCT/US2016/012268, dated Jul. 11, 2017, 4 pages.
J. Groden et al., Identification and characterization of the familial adenomatous polyposis coli gene. Cell 66, 589 (1991).
J. L. Bos et al., Prevalence of ras gene mutations in human colorectal cancers. Nature 327, 293 (1987).
J. L. Marks et al., Novel MEK1 mutation identified by mutational analysis of epidermal growth factor receptor signaling pathway genes in lung adenocarcinoma. Cancer Res 68, 5524 (Jul. 15, 2008).

J. Tol et al., Markers for EGFR pathway activation as predictor of outcome in metastatic colorectal cancer patients treated with or without cetuximab. Eur J Cancer 46, 1997 (Jul. 2010).
J. weiss et al., Frequent and focal FGFR1 amplification associates with therapeutically tractable FGFR1 dependency in squamous cell lung cancer. Sci Transl Afed 2, 62ra93 (Dec. 15, 2010).
J. Wesche, K. Haglund, E. M. Haugsten, Fibroblast growth factors and their receptors in cancer. Biochem J 437, 199 (Jul. 15, 2011).
Janjigian et al. Clin. Canc. Res. 2011, 17(8):2521-2527.
K. Koefoed et al., Rational identification of an optimal antibody mixture for targeting the epidermal growth factor receptor. mAbs 3, 584 (Nov.-Dec. 2011 ).
K. W. Kinzler et al., Identification of a gene located at chromosome 5q21 that is mutated in colorectal cancers. Science 251, 1366 (1991).
K. Yonesaka et al., Activation of ERBB2 signaling causes resistance to the EGFR directed therapeutic antibody cetuximab. Sci Transl JYfed 3, 99ra86 (Sep. 7, 2011).
L. A. Diaz, Jr. et al., The molecular evolution of acquired resistance to targeted EGFR blockade in colorectal cancers. Nature 486, 537 (Jun. 28, 2012).
L. A. Diaz, Jr., M. Sausen, G. A. Fisher, V. E. Velculescu, Insights into therapeutic resistance from whole-genome analyses of circulating tumor DNA. Oncotarget 4, 1856 (Oct. 2013).
M. C. Heinrich et al., PDGFRA activating mutations in gastrointestinal stromal tumors. Science 299, 708 (Jan. 31, 2003).
M. Keniry, R. Parsons, The role of PTEN signaling perturbations m cancer and in targeted therapy. Oncogene 27, 5477 (Sep. 18, 2008).
M. Moroni et al., Gene copy number for epidermal growth factor receptor (EGFR) and clinical response to antiEGFR treatment in colorectal cancer: a cohort study. Lancet Oneal 6, 279 (May 2005).
M. Moroni et al., Somatic mutation of EGFR catalytic domain and treatment with gefitinib in colorectal cancer. Annals of oncology: official journal of the European Society for Medical Oncology 16, 1848 (Nov. 2005).
M. Voigt et al., Functional dissection of the epidermal growth factor receptor epitopes targeted by panitumumab and cetuximab. Neoplasia 14, 1023 (Nov. 2012).
Matsushima et al., "V843I, a Lung Cancer Predisposing EGFR Mutation, Is Responsible for Resistance to EGFR Tyrosine Kinase Inhibitors," Journal of Oncology, 2014, 9(9): 1377-1384.
Montgomery et al., Nuclear localization of Dpc4 (Madh4, Smad4) in colorectal carcinomas and relation to mismatch repair/ transforming growth factor-beta receptor defects. Am J Pathol 158, 537 (2001).
N. Cancer Genome Atlas, Comprehensive molecular characterization of human colon and rectal cancer. Nature 487, 330 (Jul. 19, 2012).
N. J. Dibb, S. M. Dilworth, C. D. Mol, Switching on kinases: oncogenic activation of BRAF and the PDGFR family. Nat Rev Cancer 4, 718 (Sep. 2004).
N. Rampino et al., Somatic frameshift mutations in the BAX gene in colon cancers of the microsatellite mutator phenotype. Science 275, 967 (1997).
P. Stephens et al., Lung cancer: intragenic ERBB2 kinase mutations in tumours. Nature 431, 525 (Sep. 30, 2004).
R. Bose et al., Activating HER2 mutations in HER2 gene amplification negative breast cancer. Cancer discovely 3, 224 (Feb. 2013).
R. G. Amado et al., Wild-type KRAS is required for panitumumab efficacy in patients with metastatic colorectal cancer. J Clin Oncol 26, 1626 (Apr. 1, 2008).
R. J. Leary et al., Integrated analysis of homozygous deletions, focal amplifications, and sequence alterations in breast and colorectal cancers. Proc Natl Acad Sci US A 105, 16224 (Oct. 21, 2008).
R. K. Dearth, X. Cui, H.J. Kim, D. L. Hadsell, A. V. Lee, Oncogenic transformation by the signaling adaptor proteins insulin receptor substrate (IRS)-1 and IRS-2. Cell Cycle 6, 705 (Mar. 15, 2007).
R. M. Neve et al., A collection of breast cancer cell lines for the study of functionally distinct cancer subtypes. Cancer Cell 10, 515 (Dec. 2006).
Regales et al., J Clin. Invest, 2009, 119:3000-3010.
S. A. Hahn et al., Dpc4, a Candidate Tumor Suppressor Gene at Human Chromosome 18q21.1. Science 271, 350 (1996).

(56) References Cited

OTHER PUBLICATIONS

S. J. Baker, S. Markowitz, E. R. Fearon, J. K. Willson, B. Vogelstein, Suppression of human colorectal carcinoma cell growth by wild-type p53. Science 249, 912 (1990).

S. Jones et al., Core signaling pathways in human pancreatic cancers revealed by global genomic analyses. Science 321, 1801 (Sep. 26, 2008).

S. Misale et al., Blockade of EGFR and MEK intercepts heterogeneous mechanisms of acquired resistance to anti-EGFR therapies in colorectal cancer. Sci Transl A-fed 6, 224ra26 (Feb. 19, 2014).

S. Misale et al., Emergence of KRAS mutations and acquired resistance to anti-EGFR therapy in colorectal cancer. Nature 486, 532 (Jun. 28, 2012).

Sausen et al., "Integrated genomic analyses identify ARID1A and ARID1B alterations in the childhood cancer neuroblastoma," Nat Genet 45, 12 (Jan. 2013).

Sjoblom et al., The consensus coding sequences of human breast and colorectal cancers. Science 314, 268 (Oct. 13, 2006).

T. D. Barber, B. Vogelstein, K. W. Kinzler, V. E. Velculescu, Somatic mutations of EGFR in colorectal cancers and glioblastomas. N Engl J Nfed 351, 2883 (Dec. 30, 2004).

T. Fujioka et al., Further evidence for the involvement of insulin receptor substrates in epidermal growth factor-induced activation of phosphatidylinositol 3-kinase. European journal of biochemistry I FEBS 268, 4158 (Aug. 2001).

Thiagalingam et al., "Evaluation of Chromosome 18q in Colorectal Cancers," Nature Genetics 13, 343 (1996).

V. Guagnano et al., Discovery of 3-(2,6-dichloro-3,5-dirnethoxy-phenyl)-1-{6-[4-(4-ethyl-piperazin-1-yl)-phenylamin o]-pyrimidin-4-yl}-1-methyl-urea (NVP-BGJ398), a potent and selective inhibitor of the fibroblast growth factor receptor family of receptor tyrosine kinase, Journal of medicinal chemistry 54, 7066 (Oct. 27, 2011).

W. De Roock et al., Effects of KRAS, BRAF, NRAS, and PIK3CA mutations on the efficacy of cetuximab plus chemotherapy in chemotherapy-refractory metastatic colorectal cancer: a retrospective consortium analysis. Lancet Oneal 11, 753 (Aug. 2010).

Wood et al., The genomic landscapes of human breast and colorectal cancers. Science 318, 1108 (Nov. 16, 2007).

Y. Jiao et al., "Exome sequencing identifies frequent inactivating mutations in BAP1, ARID1A and PBRJ . . . 11 in intrahepatic cholangiocarcinomas," Nat Genet 45, 1470 (Dec. 2013).

Y. Samuels et al., High frequency of mutations of the PIK3CA gene in human cancers. Science 304, 554 (Apr. 23, 2004).

Z. Kan et al., Diverse somatic mutation patterns and pathway alterations in human cancers. Nature 466, 869 (Aug. 12, 2010).

Z. Wang et al., Mutational analysis of the tyrosine phosphatome in colorectal cancers. Science 304, 1164 (May 21, 2004).

* cited by examiner

Fig. 6A

Supplementary Table 5. Frequently Altered Genes in *KRAS* WT metastatic CRC

| Gene | Gene Name | Non-silent Point Mutations | Silent Point Mutations | Insertions or Deletions |
|---|---|---|---|---|
| TP53 | tumor protein p53 | 109 | 15 | 15 |
| APC | adenomatous polyposis coli | 99 | 13 | 57 |
| ZFP36L2 | zinc finger protein 36; C3H type-like 2 | 0 | 0 | 9 |
| SMAD4 | SMAD family member 4 | 13 | 0 | 3 |
| SYNE1 | spectrin repeat containing; nuclear envelope 1 | 34 | 19 | 3 |
| ABCA13 | ATP-binding cassette; sub-family A (ABC1); member 13 | 25 | 13 | 1 |
| LRP1B | low density lipoprotein receptor-related protein 1B | 26 | 4 | 3 |
| TTN | titin isoform N2-A | 94 | 22 | 2 |
| SOX9 | SRY (sex determining region Y)-box 9 | 3 | 1 | 6 |
| FBXW7 | F-box and WD repeat domain containing 7 | 9 | 1 | 3 |
| CDH9 | cadherin 9; type 2 (T1-cadherin) | 9 | 3 | 2 |
| LPHN3 | latrophilin-3 precursor | 14 | 4 | 0 |
| PAPPA2 | pappalysin 2 | 15 | 4 | 1 |
| TCF7L2 | transcription factor 7-like 2 (T-cell specific; HMG-box) | 10 | 2 | 2 |
| NALCN | sodium leak channel; non-selective | 16 | 3 | 1 |
| PIK3CA | phosphoinositide-3-kinase; catalytic; alpha polypeptide | 13 | 0 | 0 |
| COL11A1 | collagen; type XI; alpha 1 | 12 | 7 | 0 |
| MAGEC1 | melanoma antigen family C; 1 | 11 | 4 | 1 |
| CNTNAP4 | contactin-associated protein-like 4 isoform 2 | 11 | 6 | 0 |
| ZFPM2 | zinc finger protein; multitype 2 | 10 | 5 | 0 |
| RIMS2 | regulating synaptic membrane exocytosis 2 | 13 | 4 | 0 |
| NRAS | neuroblastoma RAS viral (v-ras) oncogene homolog | 7 | 0 | 0 |
| ZFHX4 | zinc finger homeobox protein 4 | 20 | 4 | 0 |
| KIF2B | kinesin family member 2B | 9 | 3 | 0 |
| FAT4 | FAT tumor suppressor homolog 4 (Drosophila) | 22 | 6 | 0 |

| | | | |
|---|---|---|---|
| SPTA1 | spectrin; alpha; erythrocytic 1 (elliptocytosis 2) | 15 | 4 | 0 |
| OR4K13 | olfactory receptor; family 4; subfamily K; member 13 | 2 | 1 | 3 |
| PCDH17 | protocadherin 17 | 12 | 5 | 0 |
| TXNDC3 | thioredoxin domain containing 3 (spermatozoa) | 7 | 3 | 0 |
| CYP7B1 | cytochrome P450; family 7; subfamily B; polypeptide 1 | 8 | 1 | 0 |
| SFMBT2 | Scm-like with four mbt domains 2 | 10 | 3 | 0 |
| SDK1 | sidekick homolog 1; cell adhesion molecule (chicken) | 12 | 11 | 0 |

*Includes genes that were somatically altered in 5 or more CRCs excluding high mutator samples or those with KRAS codon 12 or 13, and

Fig. 6B

| Samples Affected by Non-silent Point Mutations | Fisher's Combined p-value (uncorrected) | Bonferroni-corrected Combined P-value | BHi-corrected Combined P-value |
|---|---|---|---|
| 122 | 1.73E-253 | 1.74E-249 | 1.74E-249 |
| 119 | 3.43E-230 | 3.45E-226 | 1.73E-226 |
| 9 | 1.70E-16 | 1.72E-12 | 5.72E-13 |
| 15 | 7.94E-16 | 7.99E-12 | 2.00E-12 |
| 32 | 2.82E-13 | 2.84E-09 | 5.69E-10 |
| 24 | 4.62E-13 | 4.66E-09 | 7.76E-10 |
| 25 | 7.14E-12 | 7.19E-08 | 1.03E-08 |
| 62 | 2.12E-11 | 2.14E-07 | 2.67E-08 |
| 9 | 5.81E-11 | 5.85E-07 | 6.50E-08 |
| 10 | 2.27E-09 | 2.29E-05 | 2.29E-06 |
| 9 | 4.41E-09 | 4.44E-05 | 4.04E-06 |
| 14 | 9.71E-09 | 9.77E-05 | 7.87E-06 |
| 15 | 1.04E-08 | 0.0001049 | 7.87E-06 |
| 12 | 1.09E-08 | 0.00011024 | 7.87E-06 |
| 16 | 2.08E-08 | 0.00020927 | 1.40E-05 |
| 13 | 3.13E-08 | 0.00031514 | 1.97E-05 |
| 12 | 9.23E-08 | 0.0009294 | 5.47E-05 |
| 11 | 1.24E-07 | 0.00124607 | 6.92E-05 |
| 11 | 1.50E-07 | 0.00151174 | 7.96E-05 |
| 8 | 3.68E-07 | 0.0037003 | 0.00018501 |
| 12 | 4.91E-07 | 0.00494155 | 0.00023066 |
| 7 | 5.04E-07 | 0.00507459 | 0.00023066 |
| 18 | 7.18E-07 | 0.00722702 | 0.00031422 |
| 9 | 9.01E-07 | 0.00907353 | 0.00037806 |
| 19 | 2.03E-06 | 0.02039235 | 0.00081569 |

Fig. 6C

| | | |
|---|---|---|
| 12 | 2.36E-06 | 0.02376777 | 0.00091052 |
| 5 | 2.44E-06 | 0.02458415 | 0.00091052 |
| 11 | 3.01E-06 | 0.03026079 | 0.00108074 |
| 7 | 6.06E-06 | 0.06105914 | 0.00198006 |
| 8 | 6.10E-06 | 0.06138195 | 0.00198006 |
| 10 | 6.40E-06 | 0.06444364 | 0.00201386 |
| 12 | 7.15E-06 | 0.07195386 | 0.00218042 | d had Bonferroni corrected p values <0.10.

Supplementary Table 6. Integration of Somatic Alterations with Response to anti-EGFR Blockade

| Cetuximab Response (growth change compared to volume at treatment initiation) | 666% | 590% | 525% | 428% | 326% | 315% | 311% | 287% | 274% | 256% | 240% |
|---|---|---|---|---|---|---|---|---|---|---|---|
| Gene / Sample | 186 | 197 | 152 | 166 | 151 | 488 | 62 | 118 | 343 | 61 | 358 |
| TP53 | M | M | M | M | M | M | M | . | . | M | M |
| APC | M | M | M | M | M | M | M | M | M | M | M |
| KRAS (excluding codon 12 or 13) | . | . | . | . | . | . | . | . | . | . | . |
| NRAS | . | . | M | . | . | . | M | . | . | M | . |
| BRAF (V600E) | . | . | . | . | . | . | . | . | . | . | . |
| MET | . | . | . | . | . | . | . | . | . | . | . |
| TTN | M | M | M | M | . | . | M | . | M | . | M |
| SYNE1 | M | M | . | . | . | . | M | . | M | . | . |
| ABCA13 | . | . | . | M | . | . | . | . | . | . | . |
| LRP1B | . | . | . | . | . | . | . | M | . | . | M |
| JPH2 | . | . | . | . | . | . | . | M | M | . | M |
| MUC16 | . | . | M | M | M | . | . | M | . | M | A |
| ZFHX4 | . | . | . | M | . | . | . | . | . | . | . |
| OBSCN | . | . | . | M | . | . | . | . | . | . | M |
| SMAD4 | . | . | . | . | . | . | . | . | . | . | . |
| RTEL1 | . | . | . | . | . | . | . | . | . | . | . |
| FAT4 | . | . | M | . | . | . | . | . | M | . | M |
| HMCN1 | M | . | M | . | . | . | . | M | . | . | . |
| LAMA5 | . | . | . | . | . | . | . | M | . | . | . |
| C20orf117 | . | . | . | . | . | M | . | . | . | . | . |
| NALCN | . | M | . | . | . | . | . | . | . | . | M/A |
| PAPPA2 | . | . | . | . | . | . | . | . | . | M | A |
| CSMD3 | . | . | . | . | . | . | . | M | M | M | . |
| RYR3 | . | . | . | . | . | . | . | M | . | . | . |

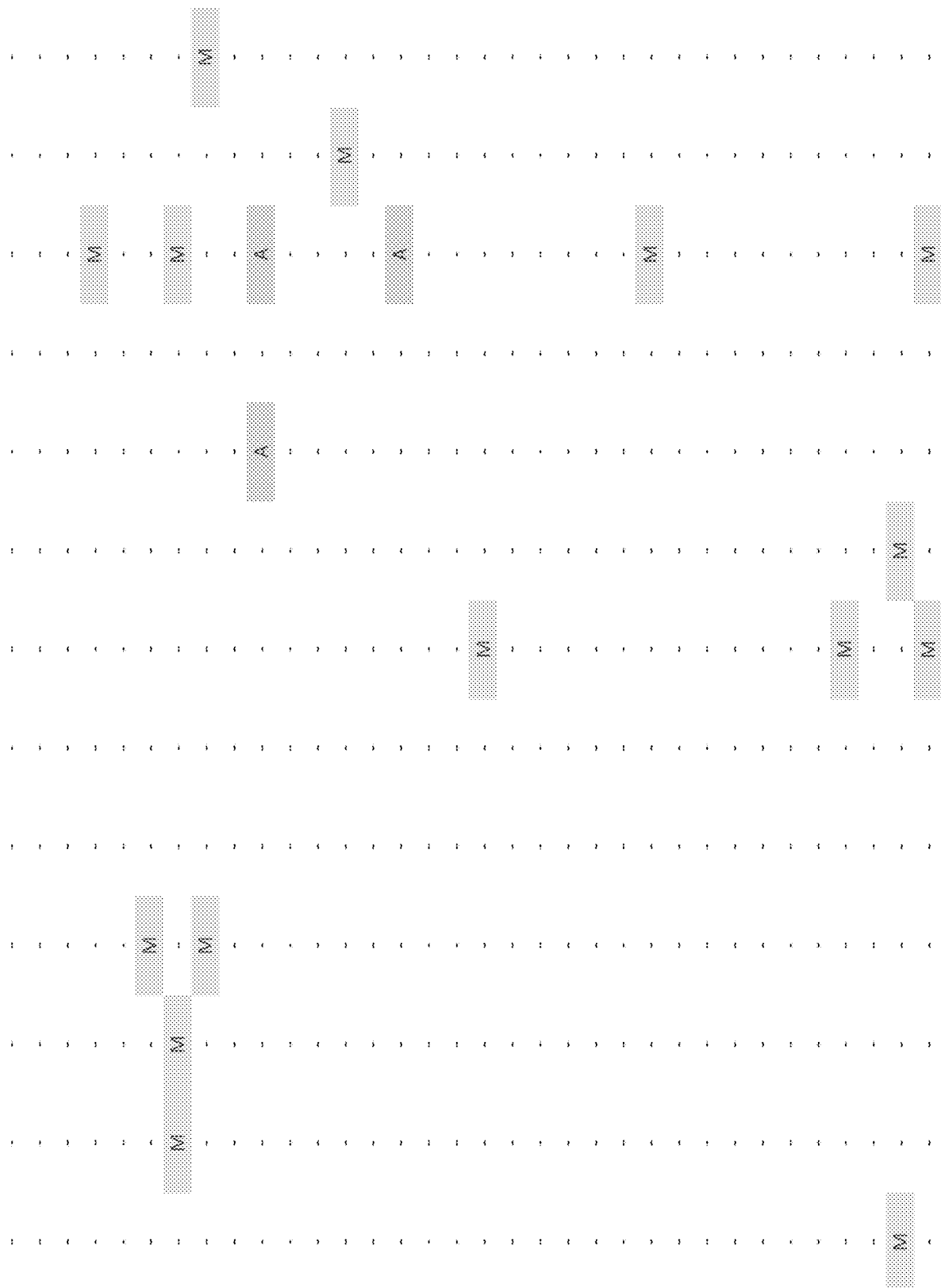
Fig. 7AAA

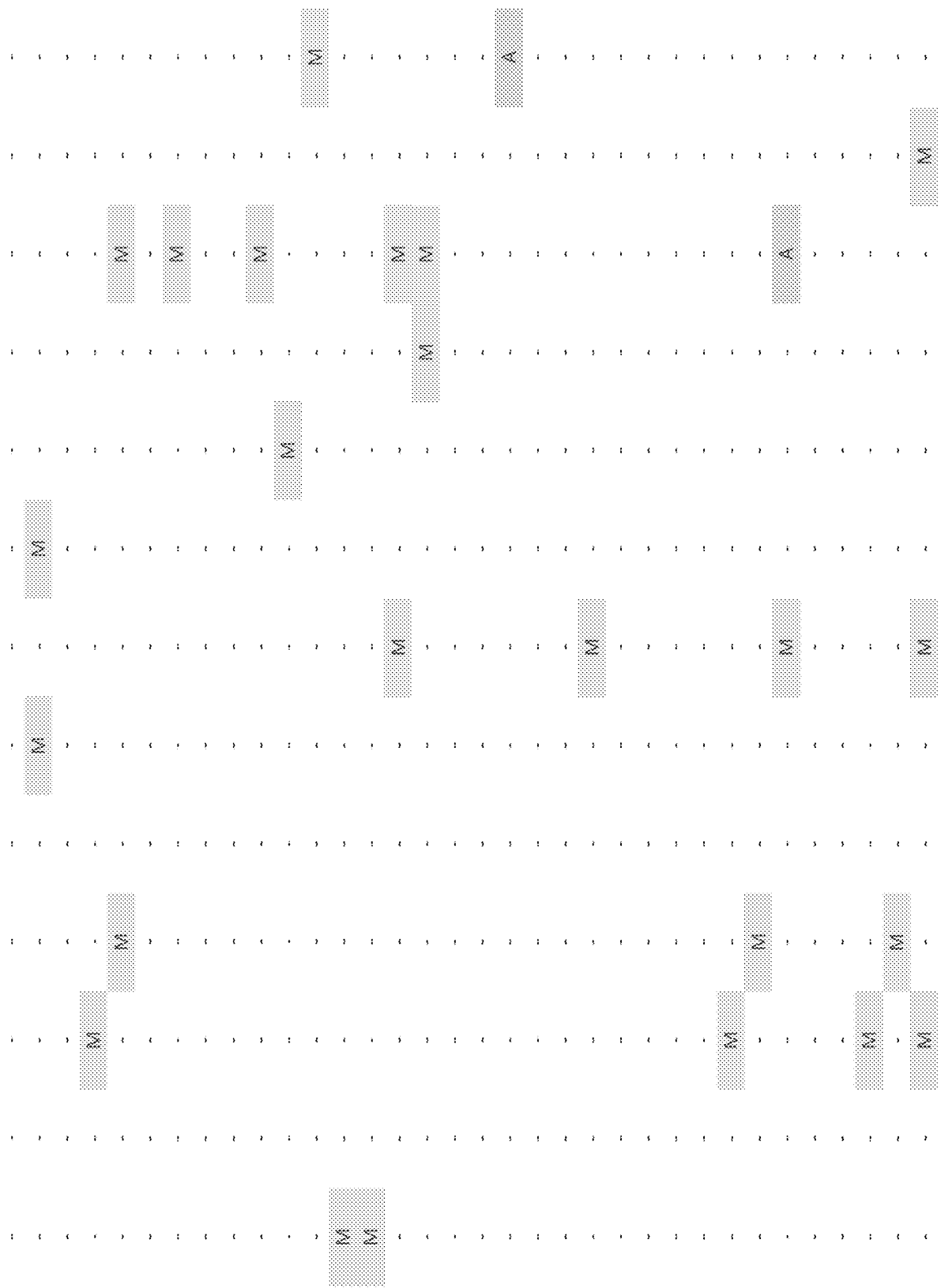
Fig. 7BBB

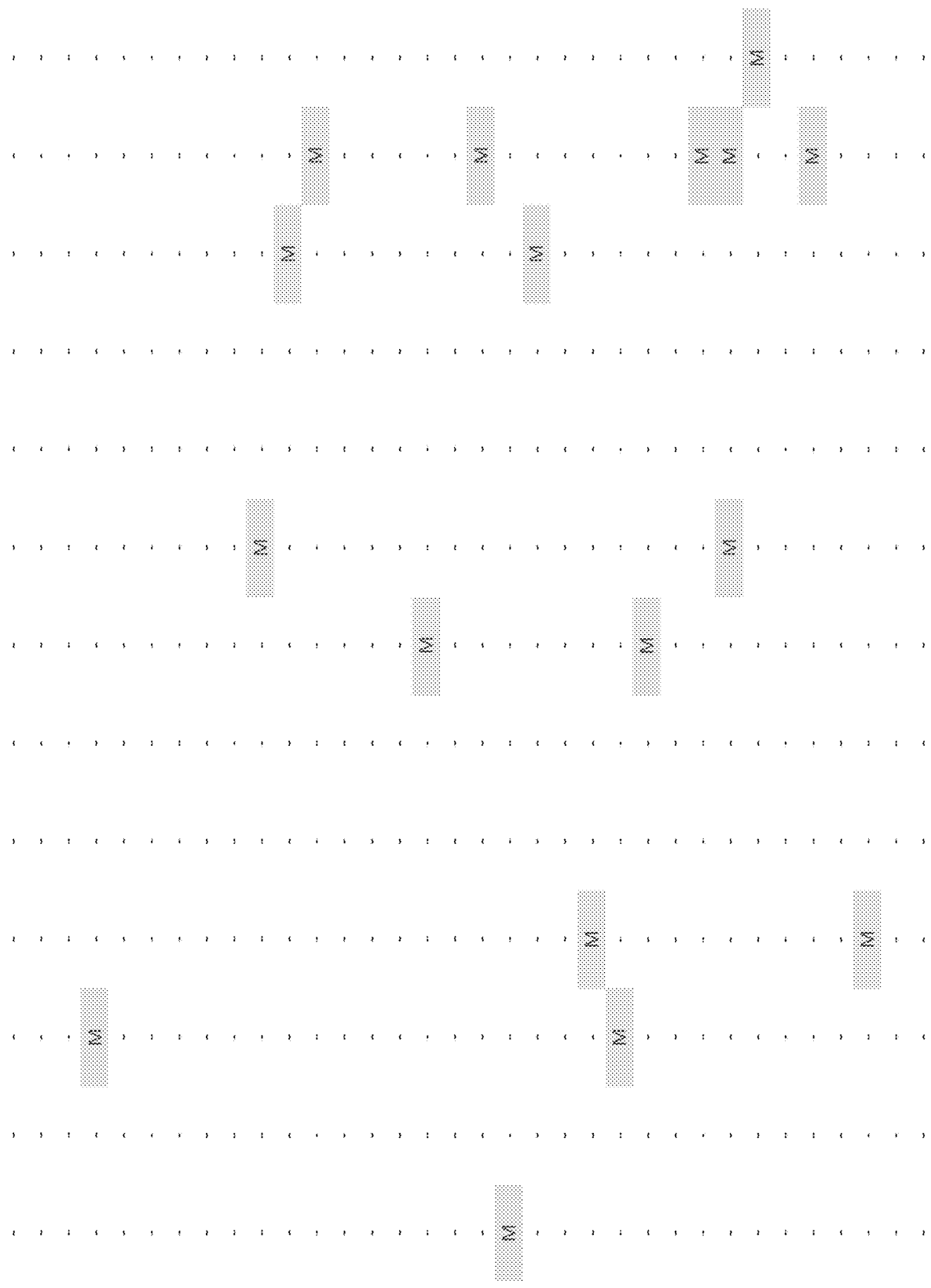
Fig. 7CCC

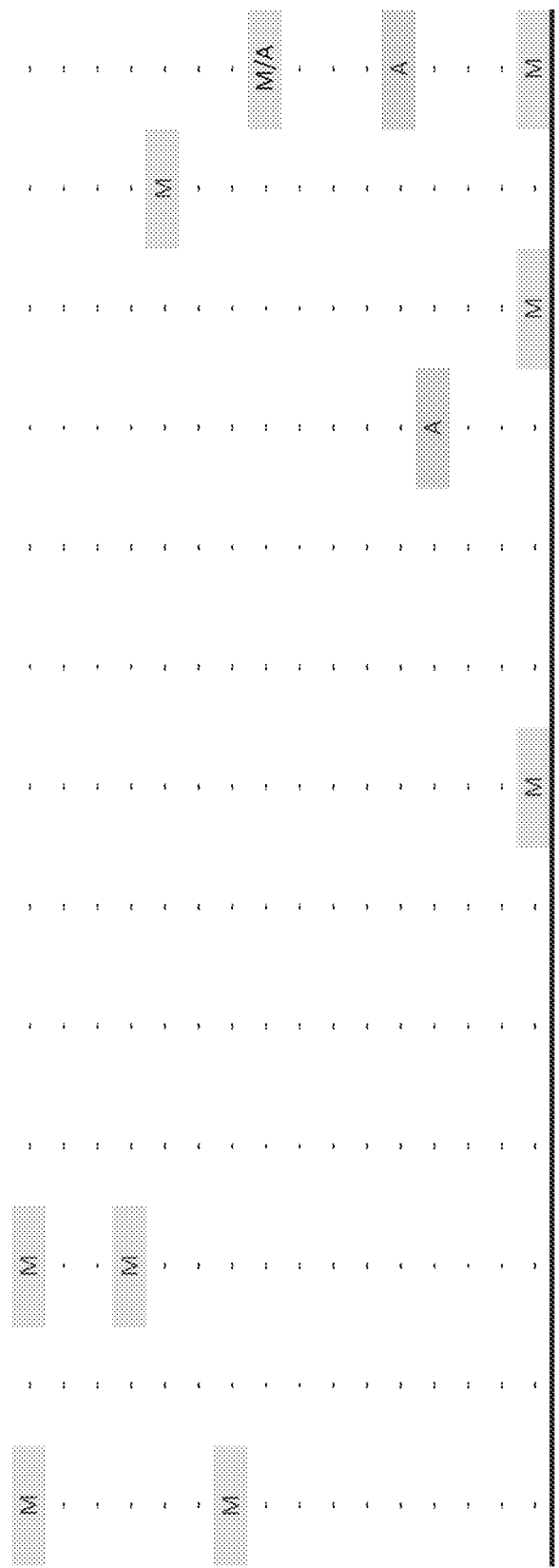
Fig. 7DDD

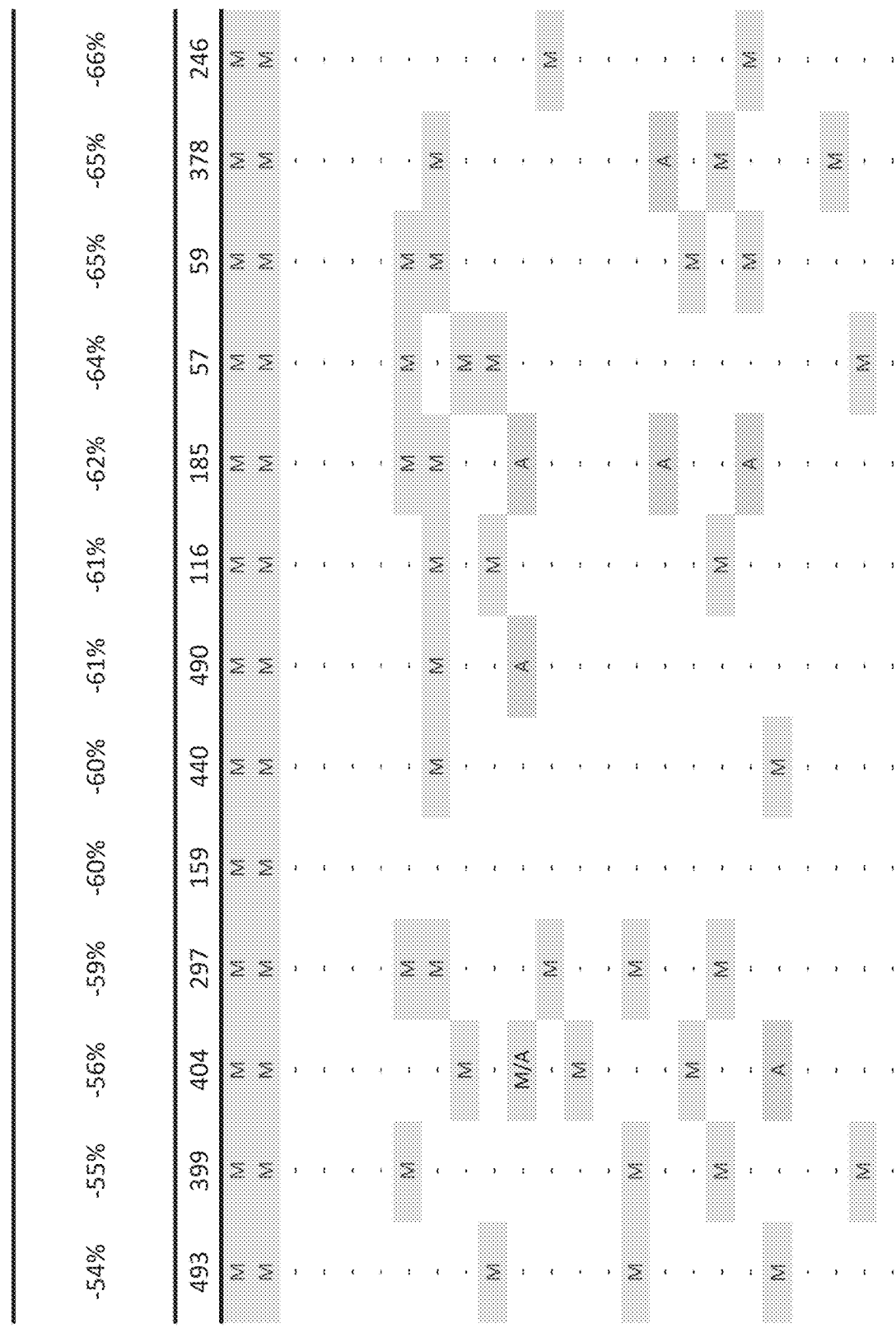
Fig. 7EEE

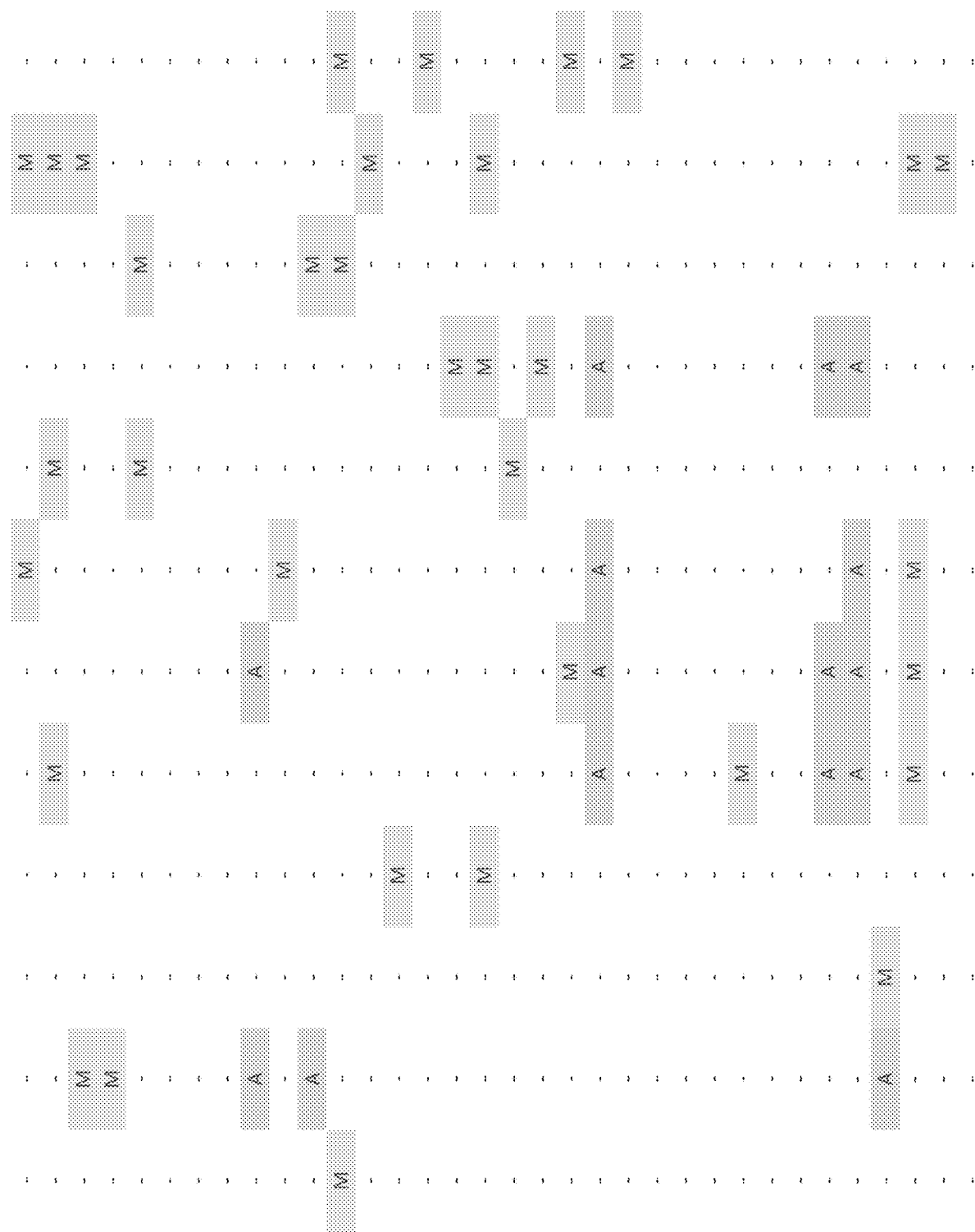
Fig. 7FFF

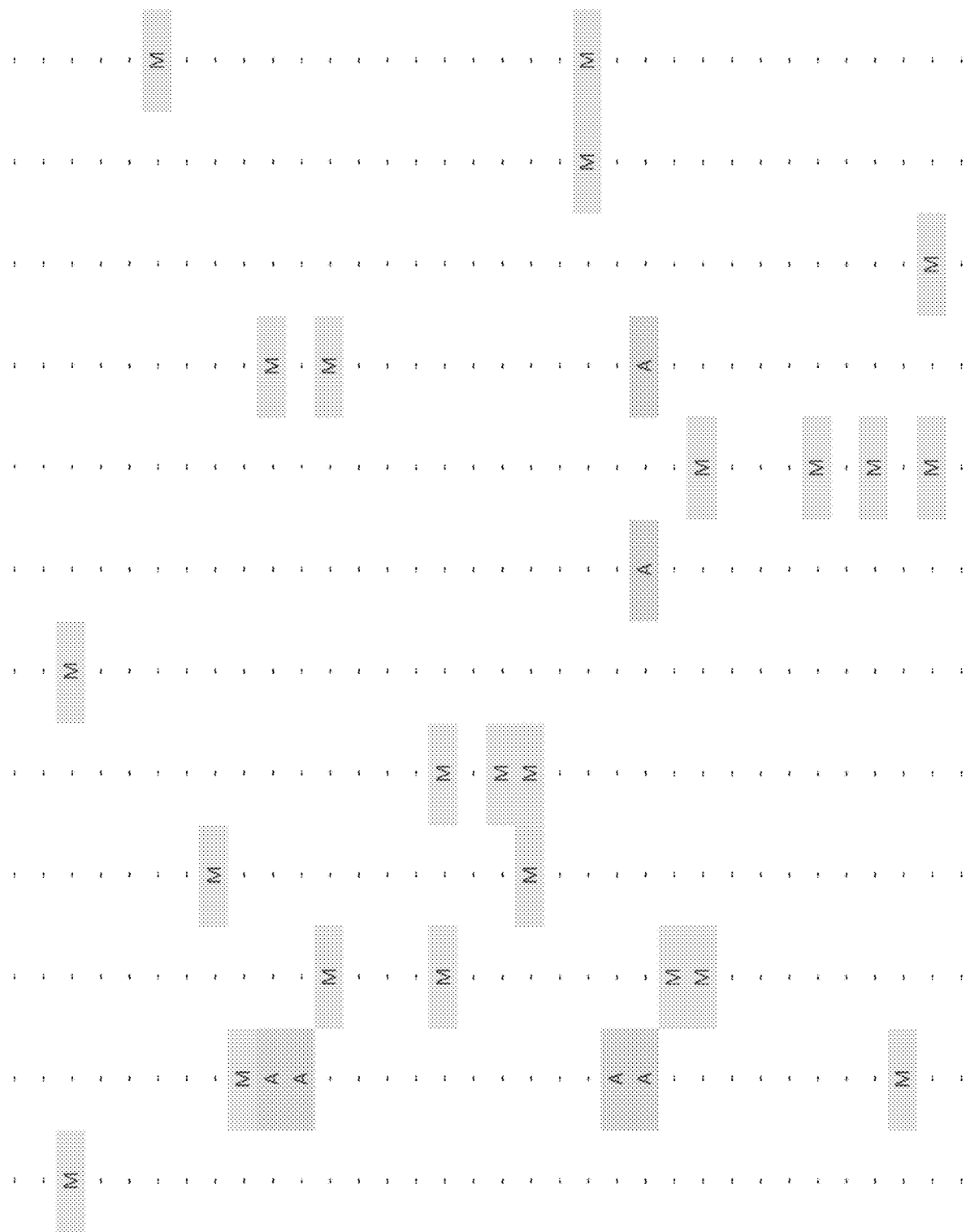
Fig. 7GGG

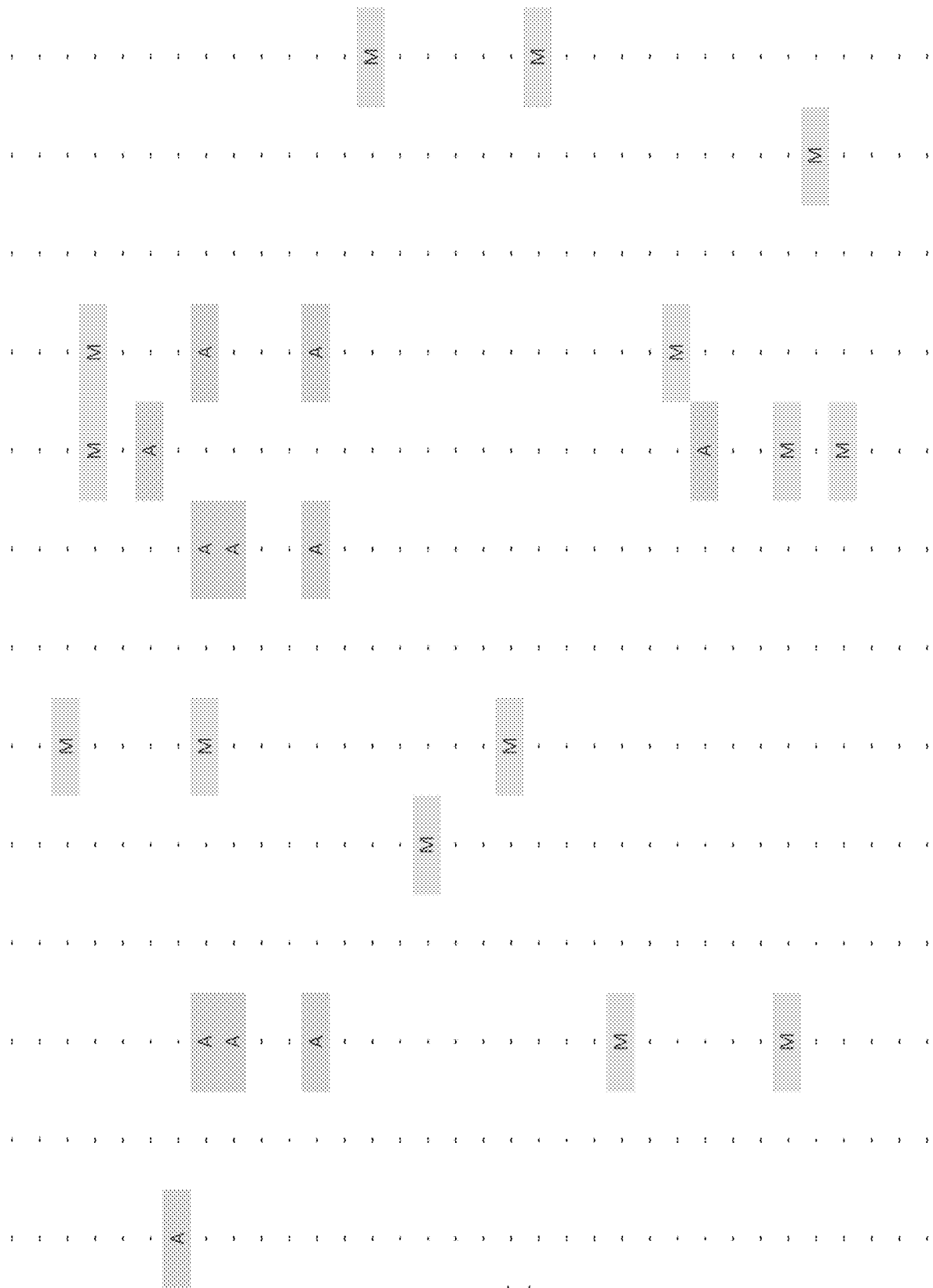
Fig. 7HHH

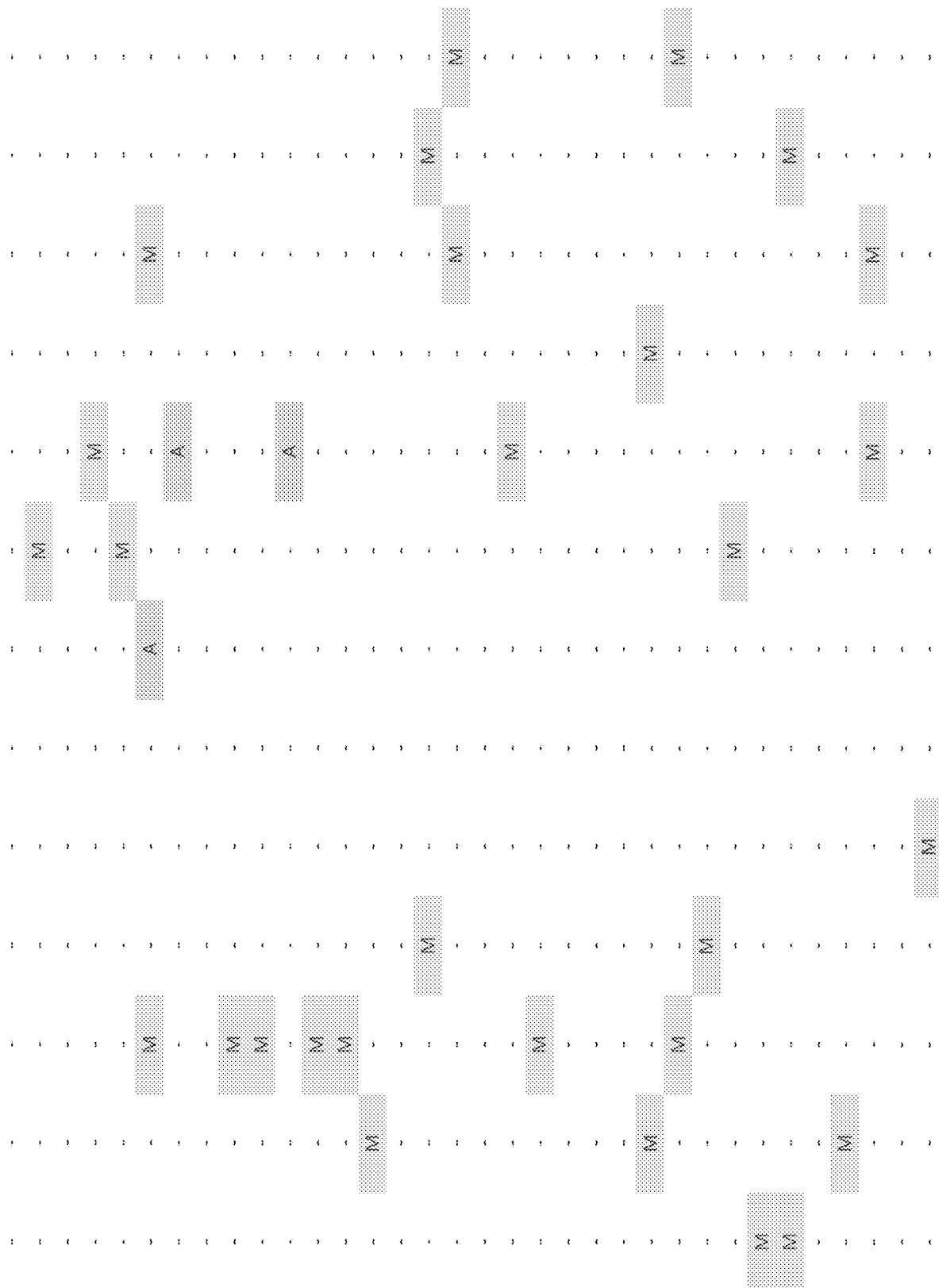
Fig. 7III

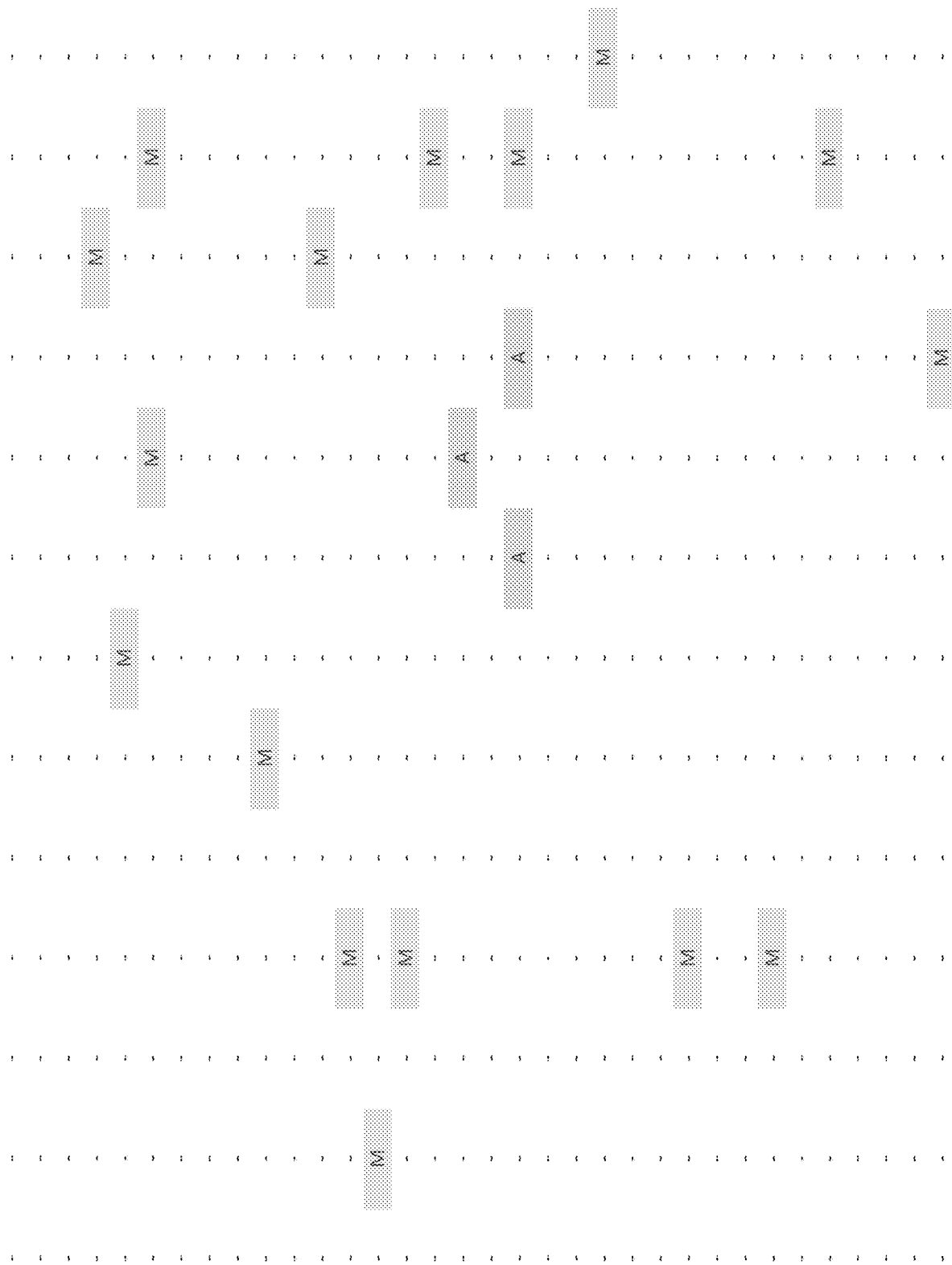
Fig. 7JJJ

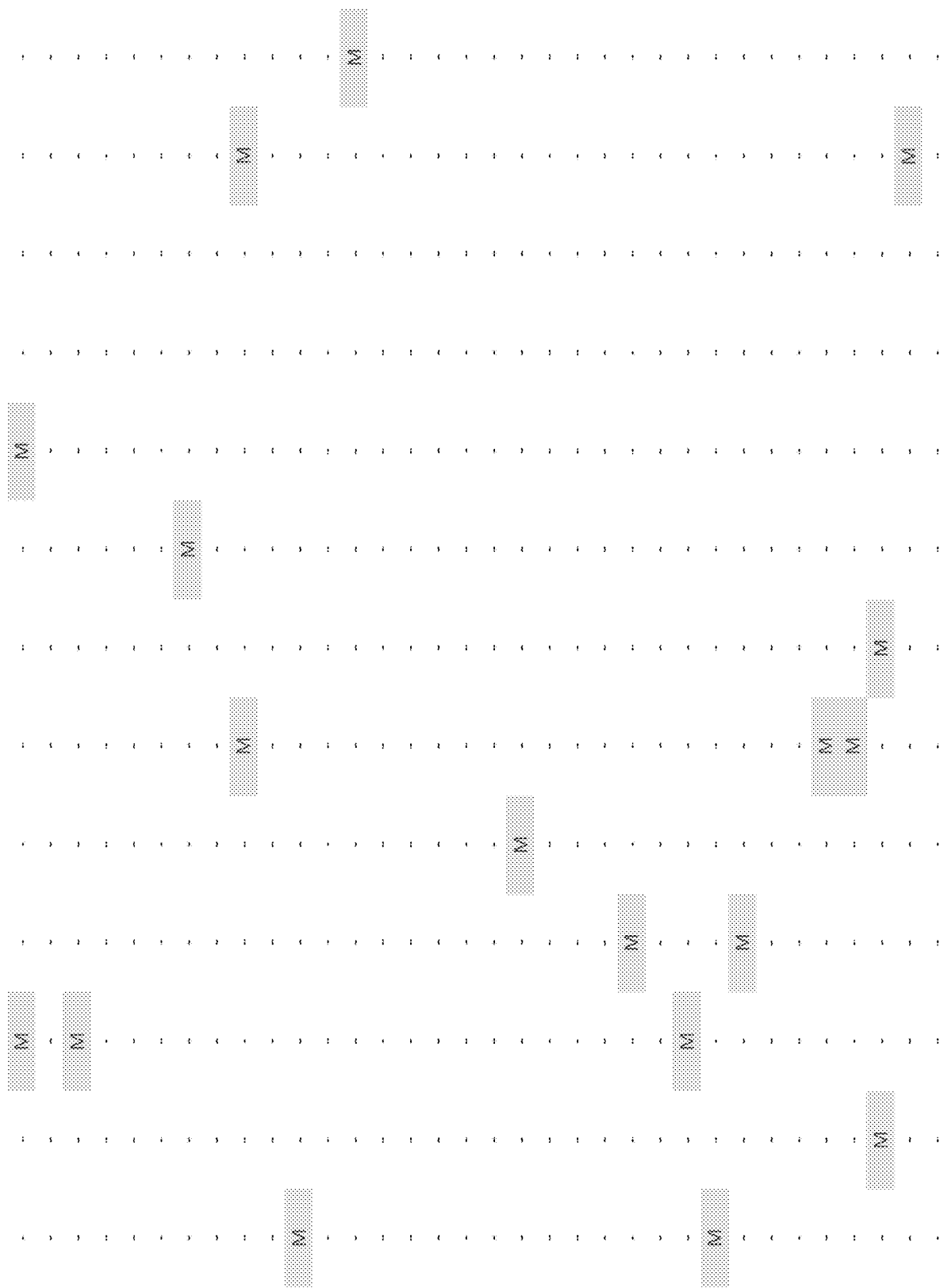
Fig. 7KKK

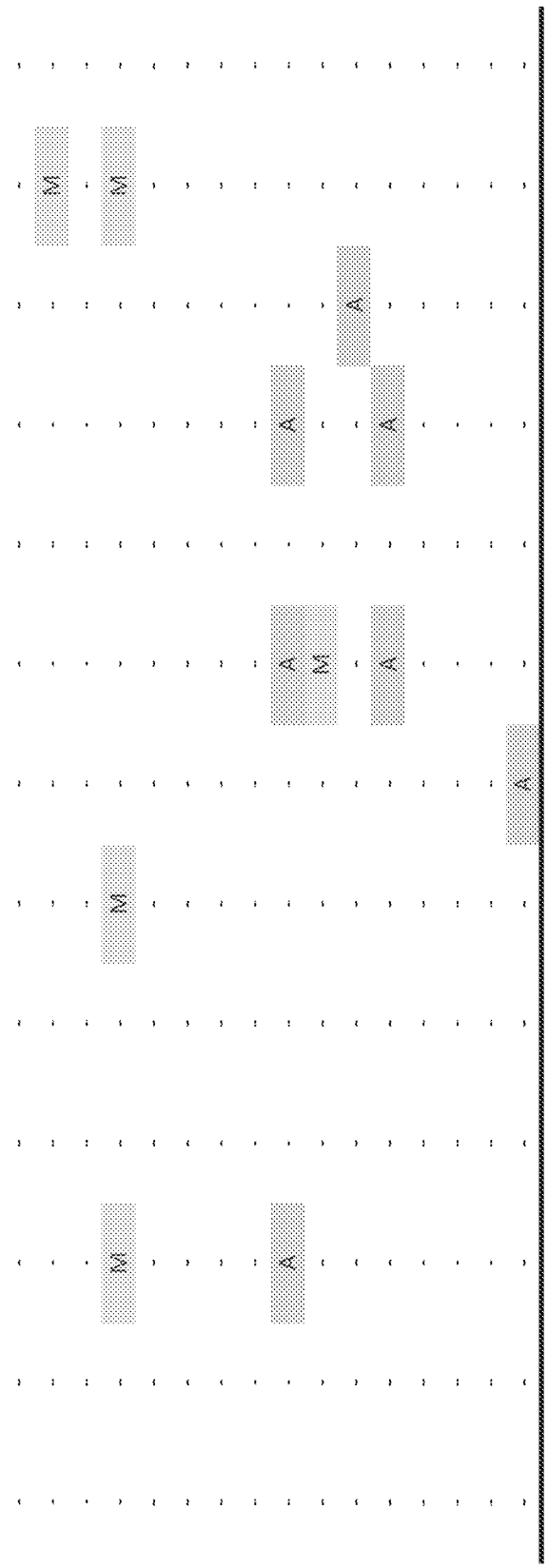
Fig. 7LLL

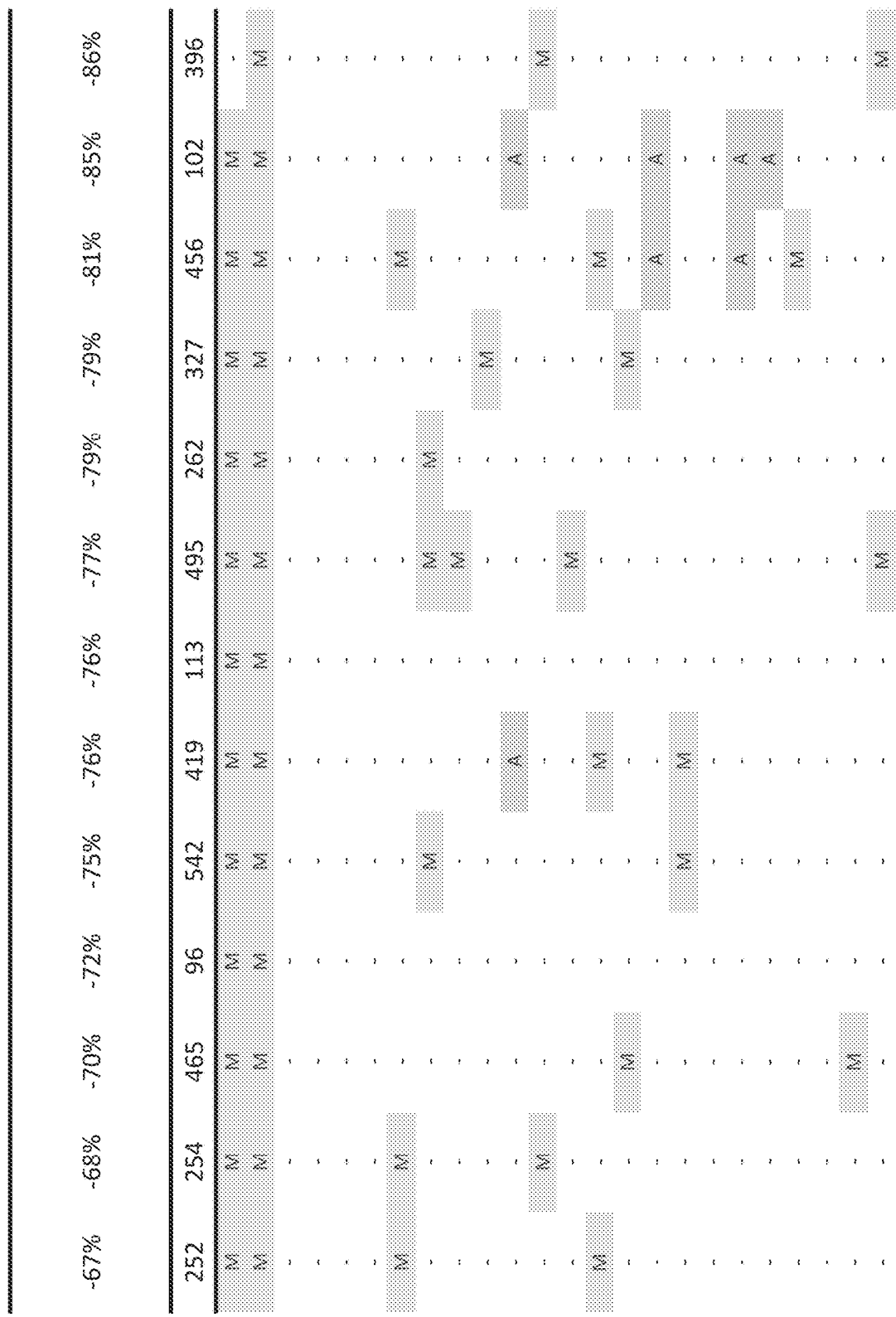
Fig. 7MMM

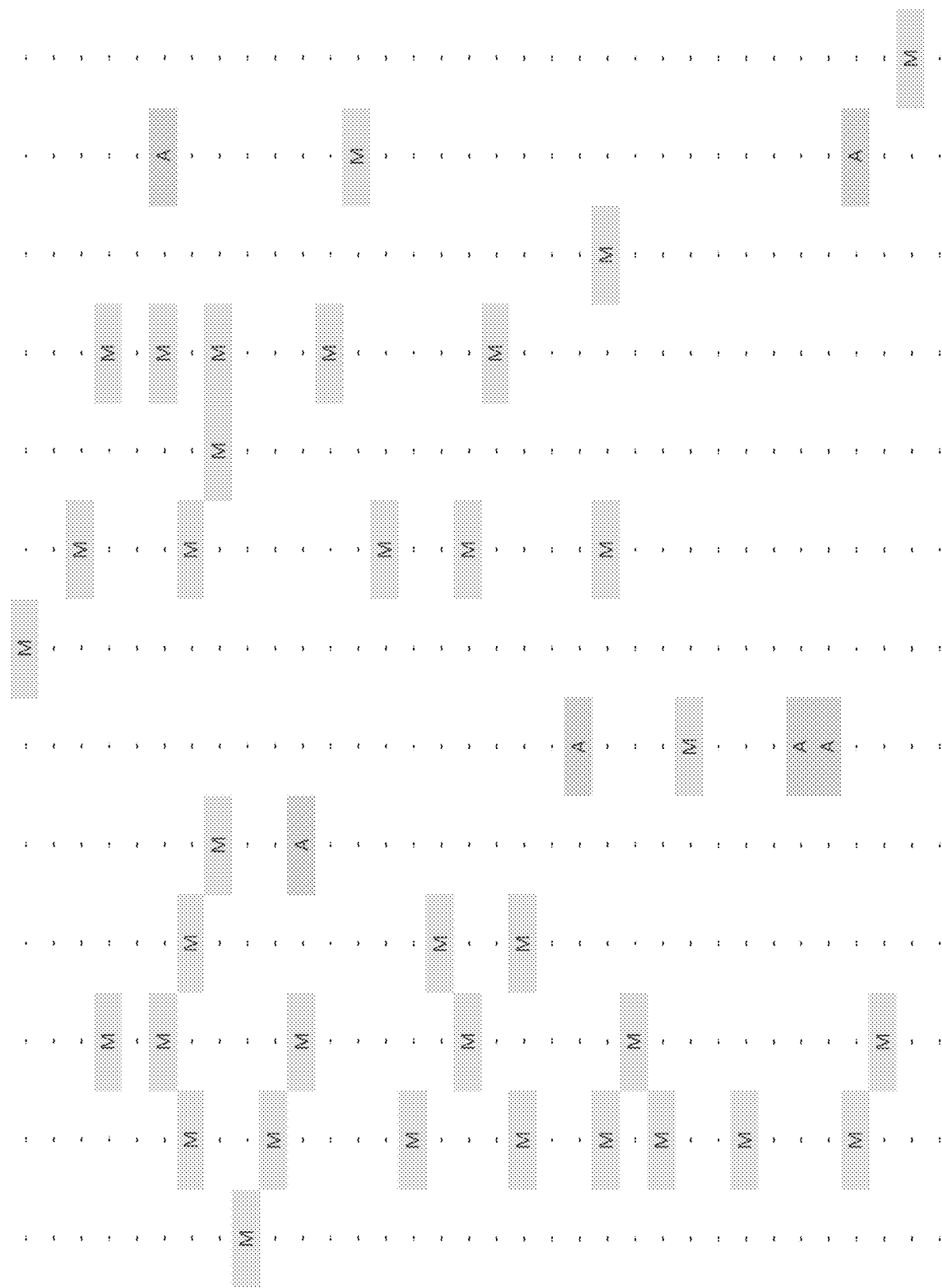
Fig. 7NNN

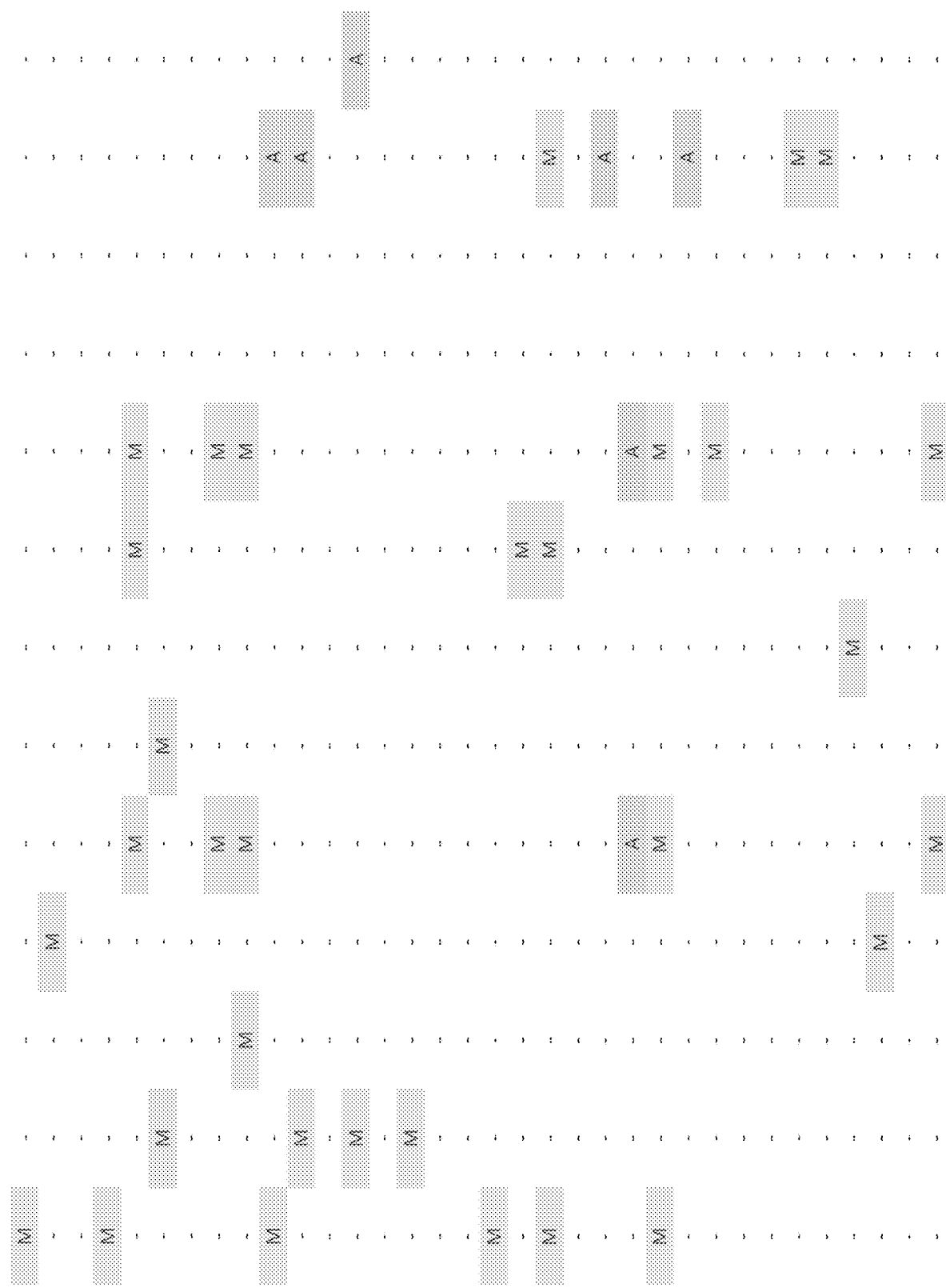
Fig. 7000

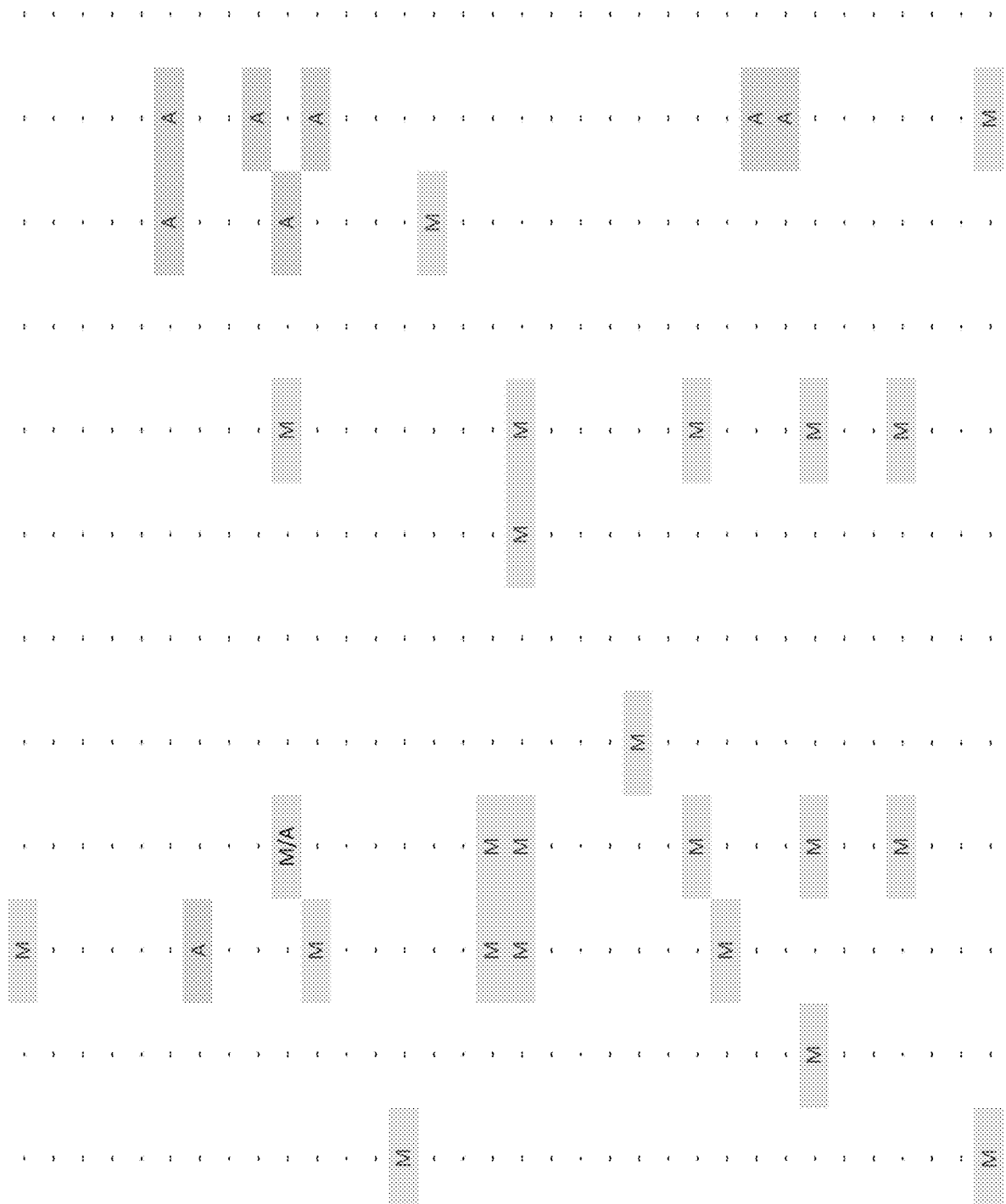
Fig. 7PPP

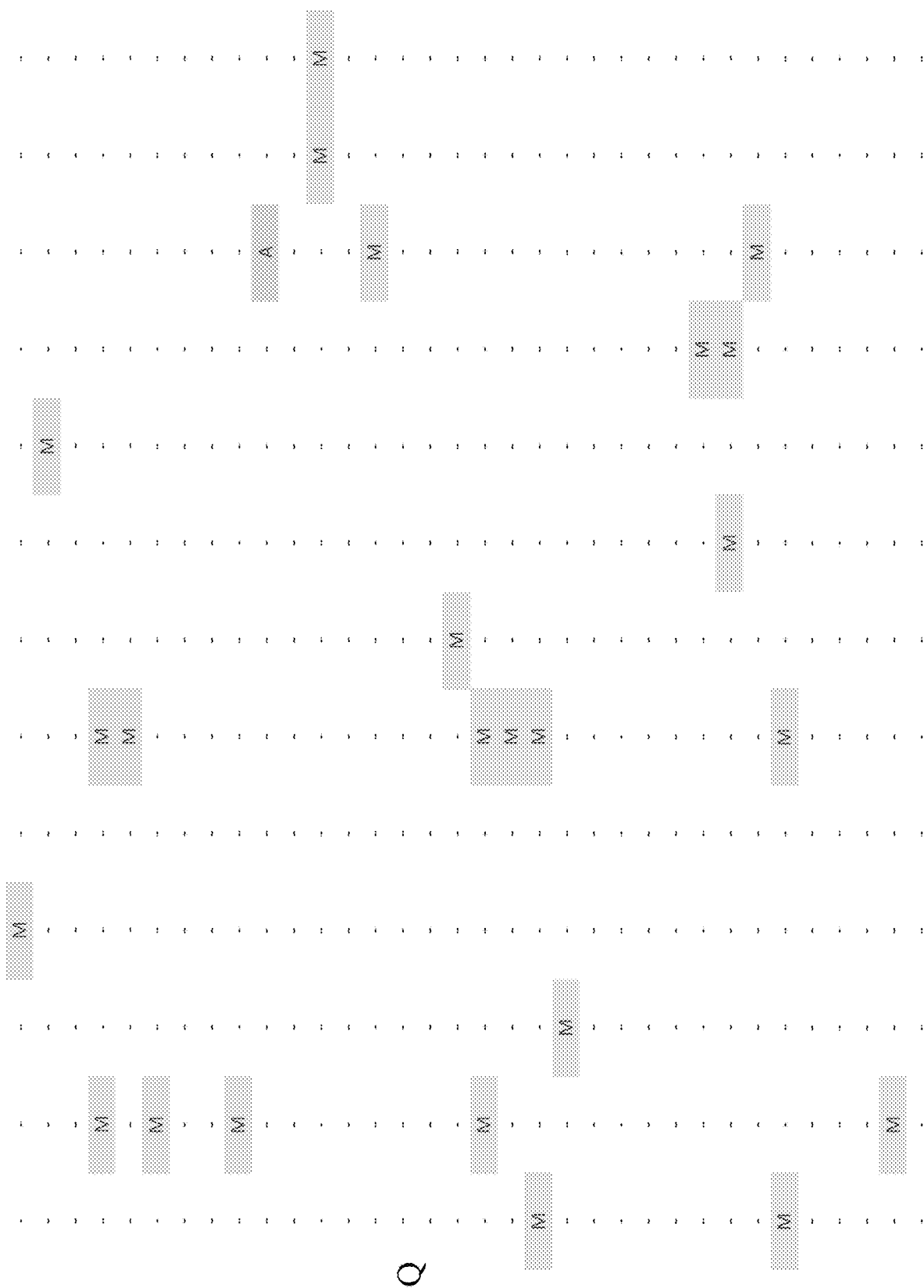
Fig. 7QQQ

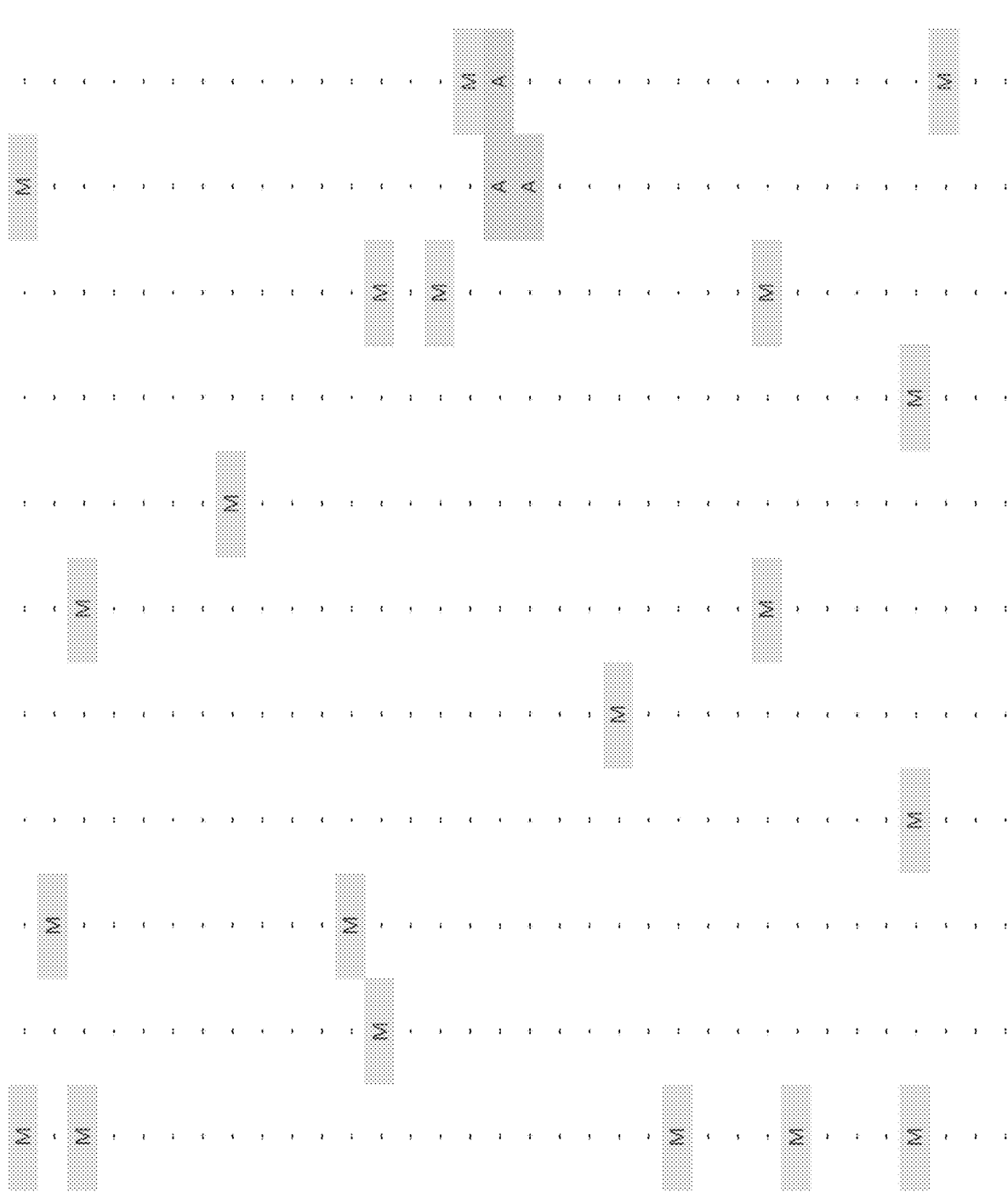
Fig. 7RRR

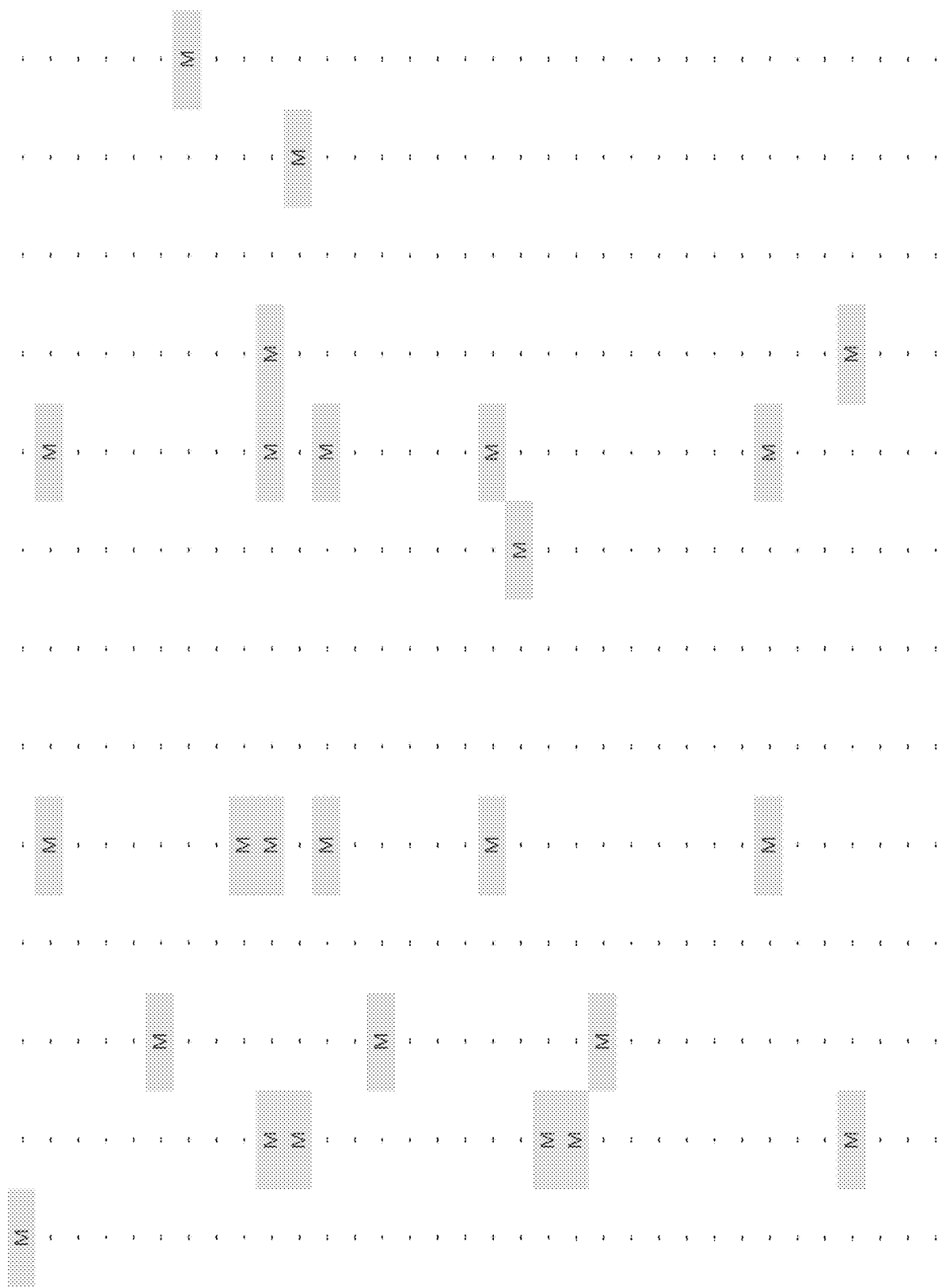
Fig. 7SSS

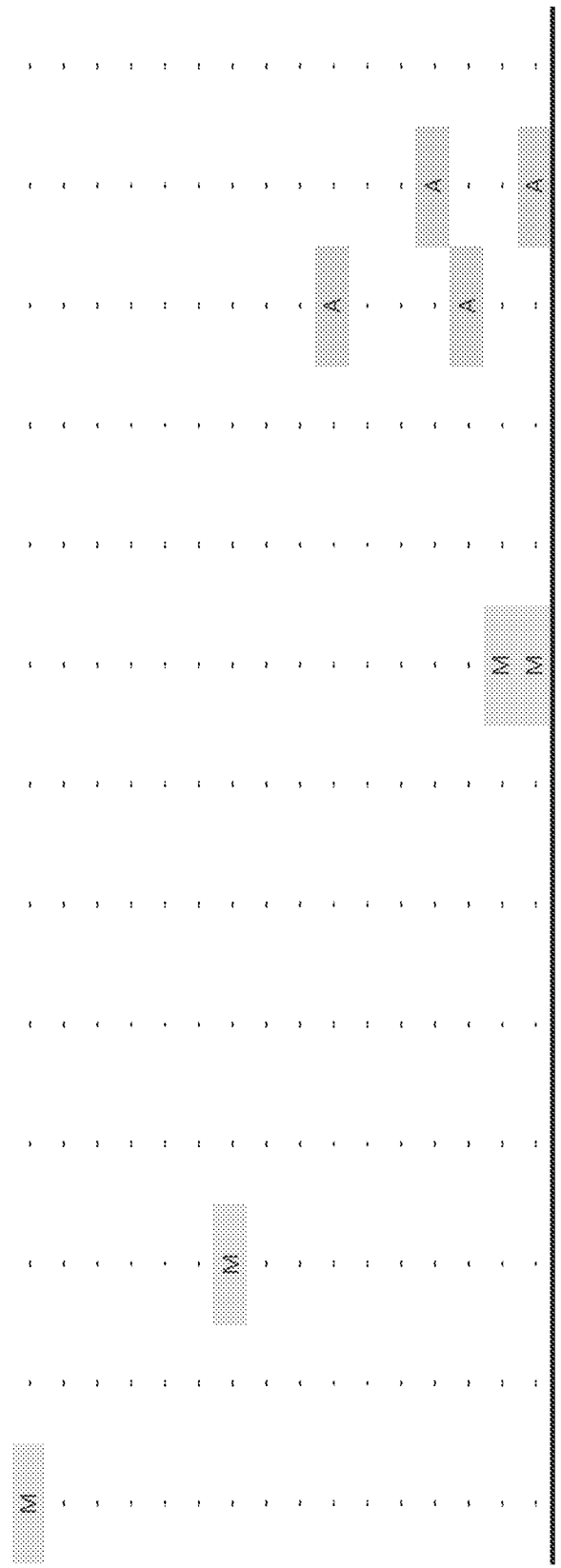
Fig. 7TTT

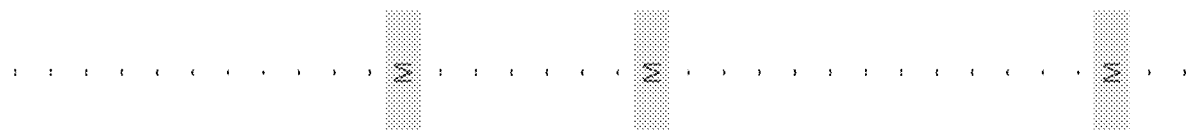
Fig. 7VVV

Fig. 7WWW

Fig. 7XXXX

Fig. 7YYY

Fig. 7ZZZ

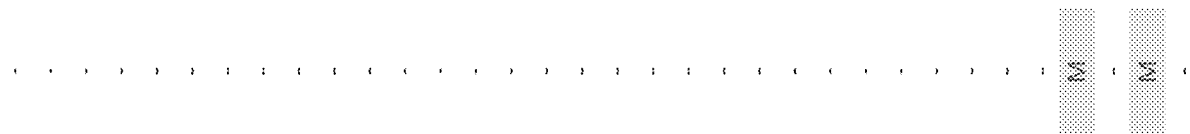
Fig. 7AAAA

Fig. 7BBBB

| Fig. 7A | Fig. 7I | Fig. 7Q | Fig. 7Y | Fig. 7GG | Fig. 7OO | Fig. 7WW | Fig. 7EEE | Fig. 7MMM | Fig. 7UUU |
| --- | --- | --- | --- | --- | --- | --- | --- | --- | --- |
| Fig. 7B | Fig. 7J | Fig. 7R | Fig. 7Z | Fig. 7HH | Fig. 7PP | Fig. 7XX | Fig. 7FFF | Fig. 7NNN | Fig. 7VVV |
| Fig. 7C | Fig. 7K | Fig. 7S | Fig. 7AA | Fig. 7II | Fig. 7QQ | Fig. 7YY | Fig. 7GGG | Fig. 7OOO | Fig. 7WWW |
| Fig. 7D | Fig. 7L | Fig. 7T | Fig. 7BB | Fig. 7JJ | Fig. 7RR | Fig. 7ZZ | Fig. 7HHH | Fig. 7PPP | Fig. 7XXX |
| Fig. 7E | Fig. 7M | Fig. 7U | Fig. 7CC | Fig. 7KK | Fig. 7SS | Fig. 7AAA | Fig. 7III | Fig. 7QQQ | Fig. 7YYY |
| Fig. 7F | Fig. 7N | Fig. 7V | Fig. 7DD | Fig. 7LL | Fig. 7TT | Fig. 7BBB | Fig. 7JJJ | Fig. 7RRR | Fig. 7ZZZ |
| Fig. 7G | Fig. 7O | Fig. 7W | Fig. 7EE | Fig. 7MM | Fig. 7UU | Fig. 7CCC | Fig. 7KKK | Fig. 7SSS | Fig. 7AAAA |
| Fig. 7H | Fig. 7P | Fig. 7X | Fig. 7FF | Fig. 7NN | Fig. 7VV | Fig. 7DDD | Fig. 7LLL | Fig. 7TTT | Fig. 7BBBB |

*Legend for Figs. 7A to 7BBBB. Orientation of Portions of Large Table.*

Fig. 7CCCC

RESPONSE TO EGFR BLOCKADE

CROSS-REFERENCE TO RELATED APPLICATIONS

This application is a divisional application of and claims priority to U.S. application Ser. No. 15/541,521, filed on Jul. 5, 2017, which is a National Stage application under 35 U.S.C. § 371 of International Application No. PCT/US2016/012268 having an International Filing Date of Jan. 6, 2016, which claims benefit of priority from U.S. Provisional Application Ser. No. 62/100,110, filed on Jan. 6, 2015.

STATEMENT OF FEDERALLY SPONSORED RESEARCH

This invention was made with government support under grant CA121113 awarded by the National Institutes of Health. The government has certain rights in the invention.

TECHNICAL FIELD OF THE INVENTION

This invention is related to the area of cancer therapy. In particular, it relates to primary and acquired resistance to cancer therapy agents, as well as determinants of increased sensitivity.

BACKGROUND OF THE INVENTION

Colorectal cancer (CRC) is the third most common cancer world-wide with 1.2 million patients diagnosed yearly, and over 600,000 dying of the disease. In CRCs, tumor progression is accompanied by a series of genetic changes that affect several oncogenes and tumor suppressor genes and their cellular pathways. These include dysregulation of the APC/WNT pathway (1-3), mutations of KRAS or BRAF oncogenes in early stage disease (4-6), activation of the PI3K pathway through alterations in PIK3CA or PTEN (7, 8), and alterations in the p53 and TGF beta pathways in later stages of disease progression (9-14). Additional genetic abnormalities have been observed in key signaling genes (15-17) and through large scale genomic analyses of CRCs (18-20).

In late stage CRC, the most commonly used targeted therapies are monoclonal antibodies cetuximab and panitumumab which inactivate EGFR (21). Recent studies of CRC resistance to anti-EGFR antibody therapy have identified alterations in KRAS (22-24), NRAS (25), BRAF (25-27), PIK3CA (25, 28), along with amplification of MET (29) and ERBB2 (30, 31) as likely mechanisms of primary resistance to this therapy. Alterations in many of these genes as well as mutations in EGFR have been shown to provide acquired (secondary) resistance to EGFR inhibition (29, 32-34).

Despite these efforts, additional mechanisms of resistance to EGFR blockade are thought to be present in CRC (35) and little is known about determinants of sensitivity to this therapy. There is a continuing need in the art for a systematic genome-wide study in CRC to identify genetic changes associated with responsiveness to any targeted therapy.

SUMMARY OF THE INVENTION

According to one aspect of the invention a method is provided for treating a tumor in a human. A sample from the tumor is tested and amplification or an activating mutation in tyrosine kinase receptor adaptor gene IRS2 is determined. The human is treated with or prescribed an inhibitor of a receptor selected from the group consisting of: MET, ERBB2, EGFR, FGFR, and PDGFR.

According to another aspect of the invention a method is provided for treating a tumor resistant to EGFR blockade in a human. An inhibitor of FGFR1 and an inhibitor of EGFR are administered to the human.

According to yet another aspect of the invention another method of treating a tumor in a human is provided. The tumor is resistant to EGFR blockade. An EGFR kinase inhibitor and an anti-EGFR antibody are administered to the human.

According to still another aspect of the invention an additional method is provided for treating a tumor resistant to EGFR blockade in a human. An inhibitor of MEK1 and an inhibitor of ERK are administered to the human.

According to another aspect of the invention a method is provided for treating a tumor in a human. The tumor is resistant to EGFR blockade. A monoclonal antibody to EGFR that binds to an epitope distinct from the epitopes bound by cetuximab and panitimumab is administered to the human.

According to yet one more aspect of the invention a method is provided for treating a human with a tumor. A sample from the tumor is tested and a mutation in a gene selected from the group consisting of: FGFR, PDGFRa, MAP2K1, and ERBB2 is determined. The human is then treated with an antibody to EGFR.

According to an additional aspect of the invention a method is provided for treating a human with a tumor. The tumor is treated with a first antibody to EGFR. Then a sample from the tumor is tested and a mutation in EGFR's ectodomain is determined. The treatment is then modified to include an EGFR kinase inhibitor or an anti-EGFR antibody to a distinct epitope from the epitope bound by the first antibody.

These and other embodiments which will be apparent to those of skill in the art upon reading the specification provide the art with methods to overcome primary and secondary resistance in tumors to EGFR blockade.

PIK3CA exon 20 mutations; EGFR ecto- and kinase domain mutations and amplifications. Tumor growth values are thresholded at 200%.

Figure 3:
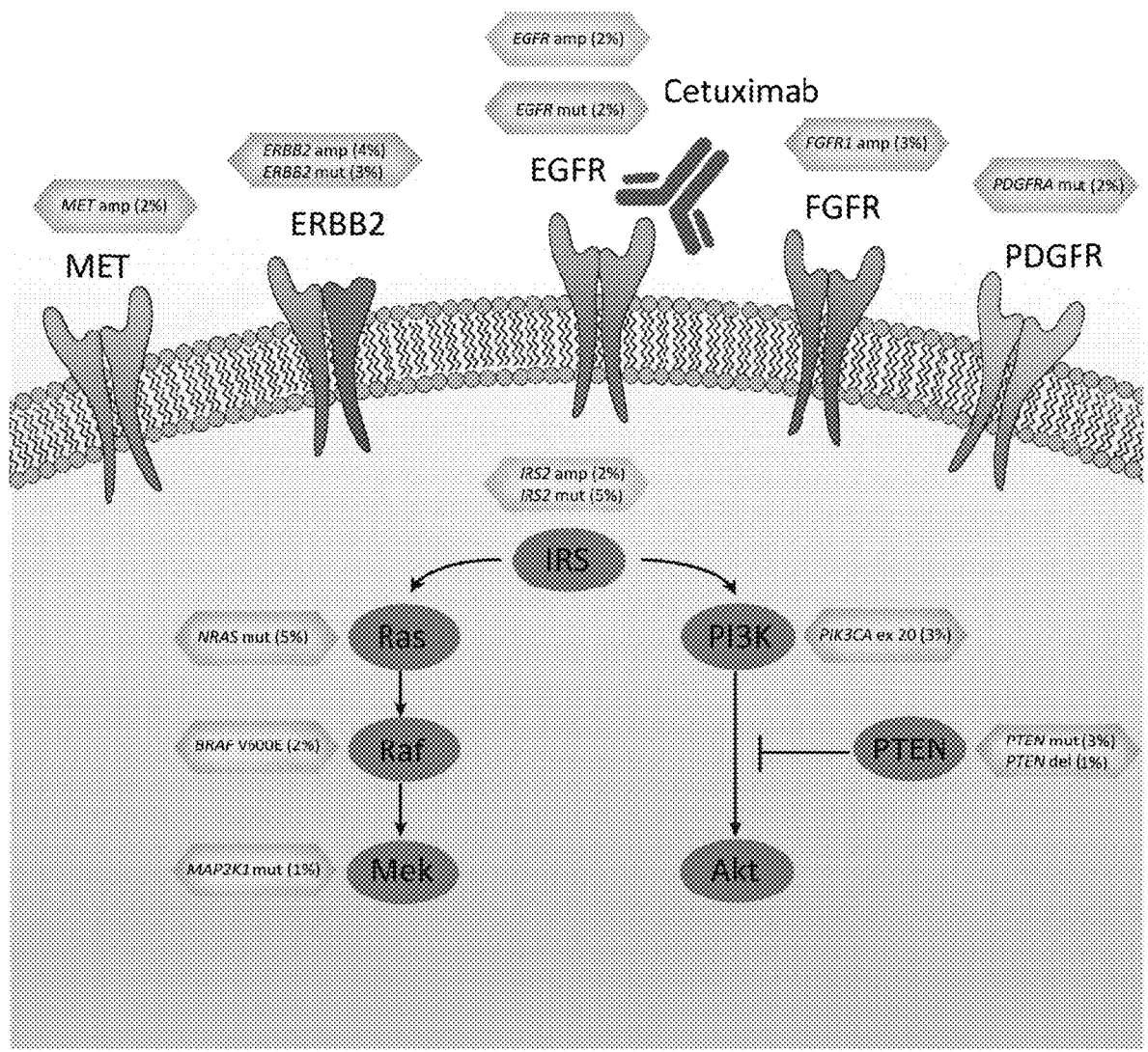

FIG. 3. EGFR signaling pathway genes involved in cetuximab resistance or sensitivity. Altered cell surface receptors or members of RAS or PI3K pathways identified in this study are indicated. Somatic alterations related to resistance or sensitivity are highlighted in red or green boxes, respectively. The percentages indicate the fraction of KRAS WT tumors containing the somatic alterations in the specified genes. For the following genes a subset of alterations are indicated: PDGFRA kinase domain mutations; EGFR ecto- and kinase domain mutations and amplifications.

Figure 4A:
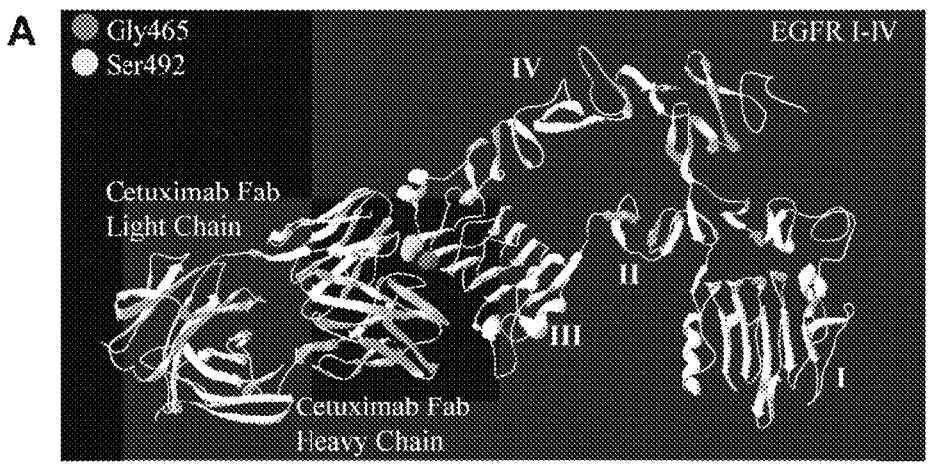
Figure 4B:
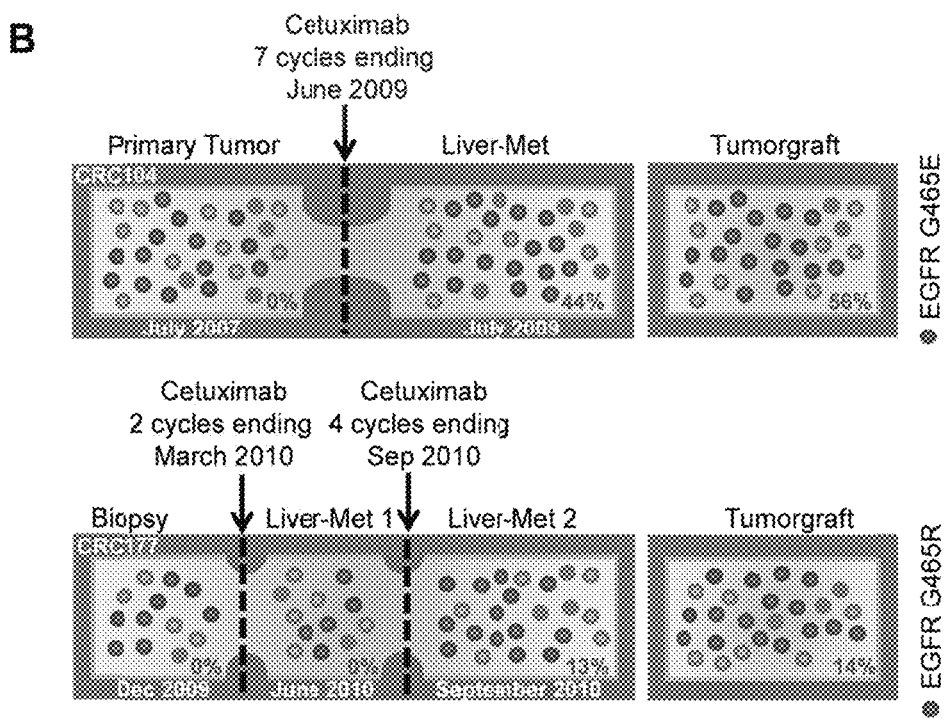
Figure 4C:
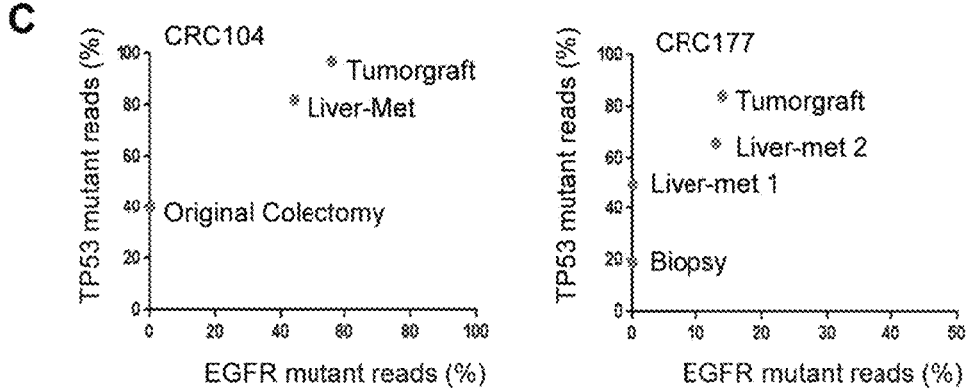

FIG. 4A-4C. Genetic alterations involved in secondary resistance to anti EGFR therapy. FIG. 4A. The location of the secondary resistance mutations detected in EGFR are analyzed through structural models of the soluble extracellular region of EGFR (domains I-IV) and the antigen binding fragment (Fab) of cetuximab. The G465 residue altered in CRC104 and CRC177 are shown in red while the S492 residue that has been described to confer cetuximab resistance (32) is shown in yellow. FIG. 4B. Schematic of evolution of EGPR secondary resistance in the two analyzed CRCs with acquired resistance. Cetuximab-naïve samples were sequenced to investigate whether somatic mutations affecting EGFR amino acid 465 (indicated by red circles) were detectable prior to treatment. The fraction of mutant tags detected for each sample is indicated. FIG. 4C. Analysis of the fraction of TP53 mutant reads (vertical axis) compared to the fraction of reads with EGFR ectodomain mutations (horizontal axis) show the level of EGFR alterations in different lesions when controlled for tumor cellularity.

FIG. 5A-5D. Therapeutic intervention in preclinical trials to overcome resistance to anti-EGFR antibody blockade. Tumor growth curves in tumorgraft cohorts (n=6 for each treatment arm) derived from individual patients with (FIG. 5A) FGFR1 amplification (CRC477). (FIG. 5B) EGFR kinase mutation (CRC334), (FIG. 5C) MAP2K1 K57N mutation (CRC343), and (FIG. 5D) EGFR ectodomain mutations (CRC104 left and CRC177 right) treated with placebo or targeted treatments.

Figure 7B:
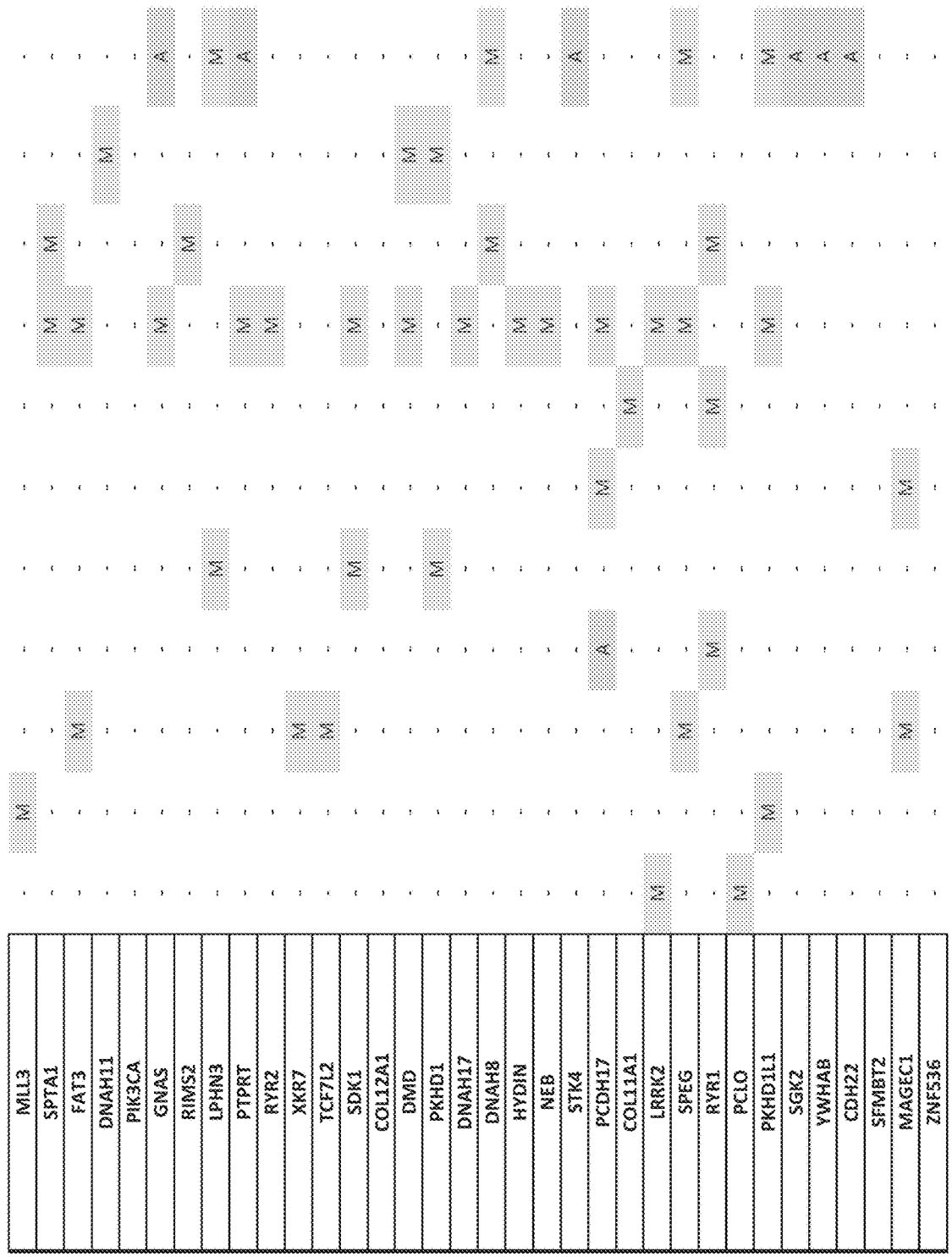
Figure 7C:
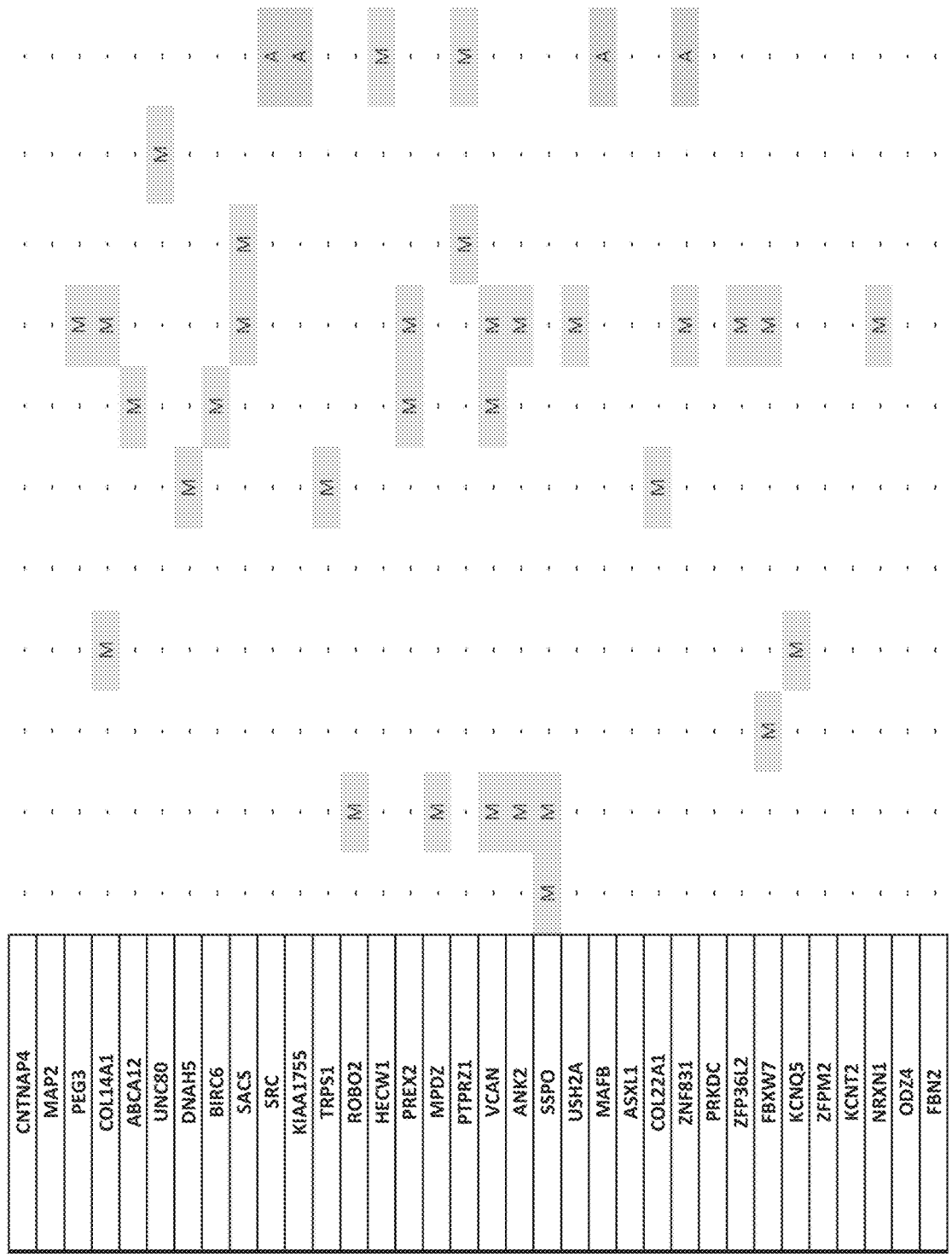
Figure 7D:
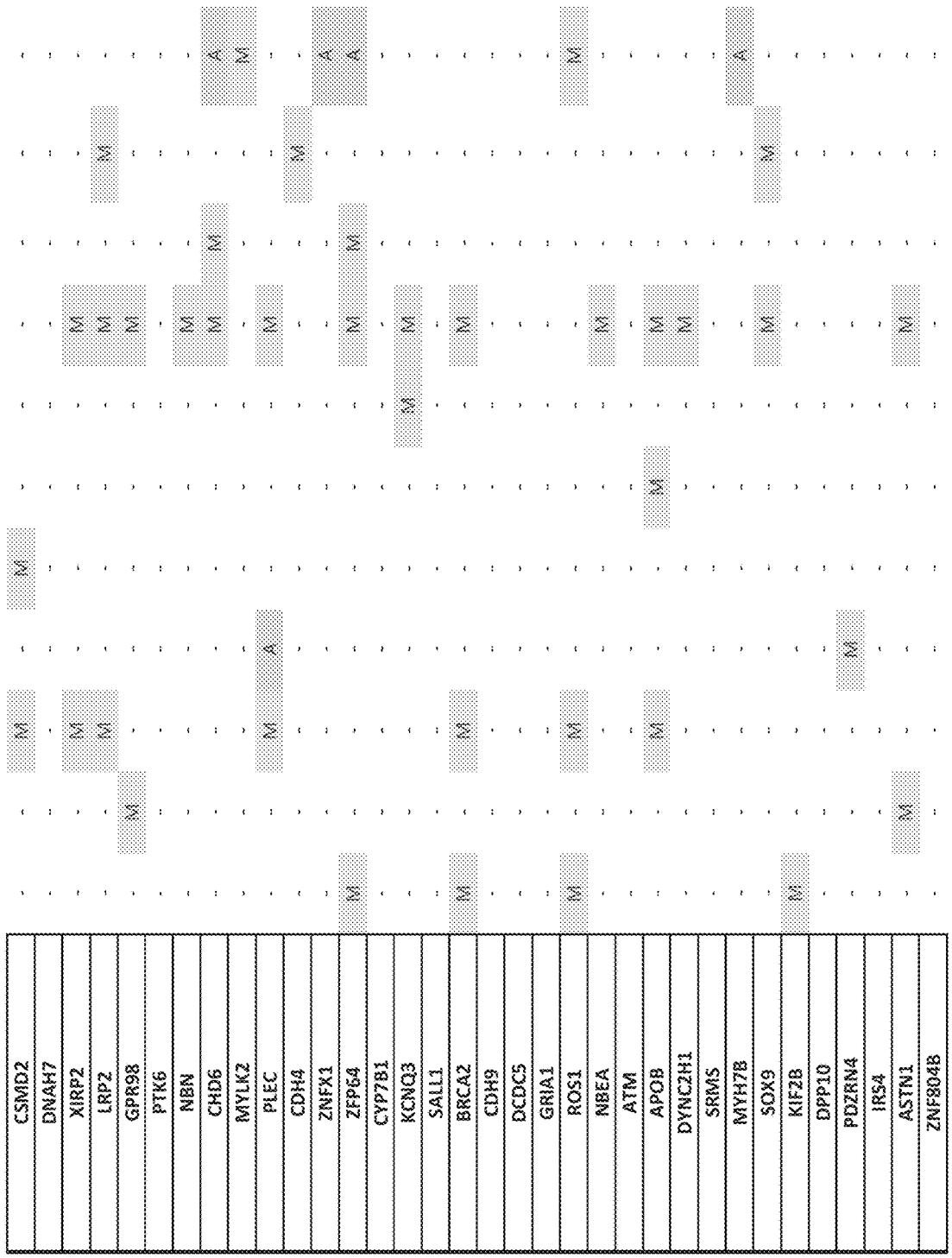
Figure 7E:
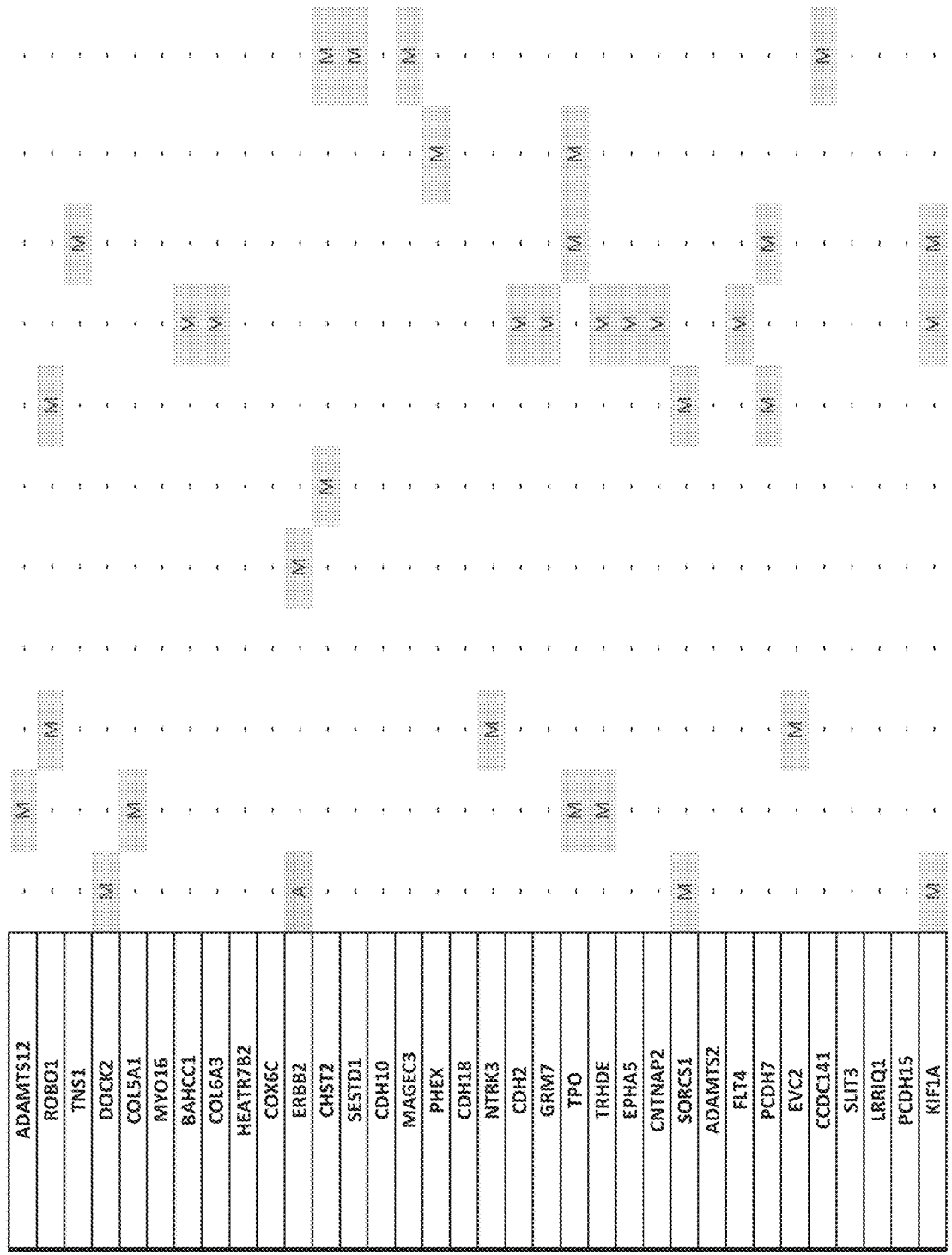
Figure 7F:
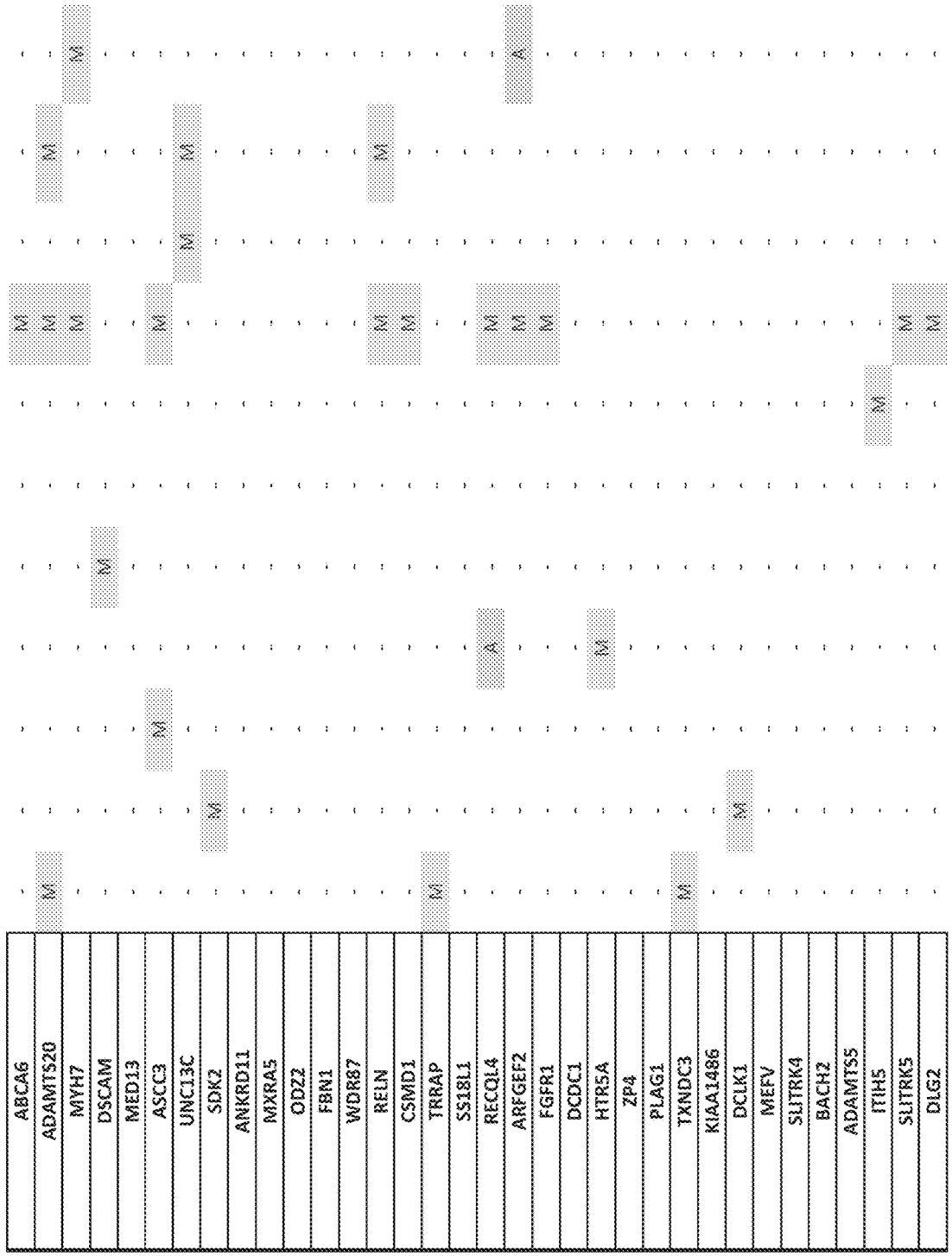
Figure 7G:
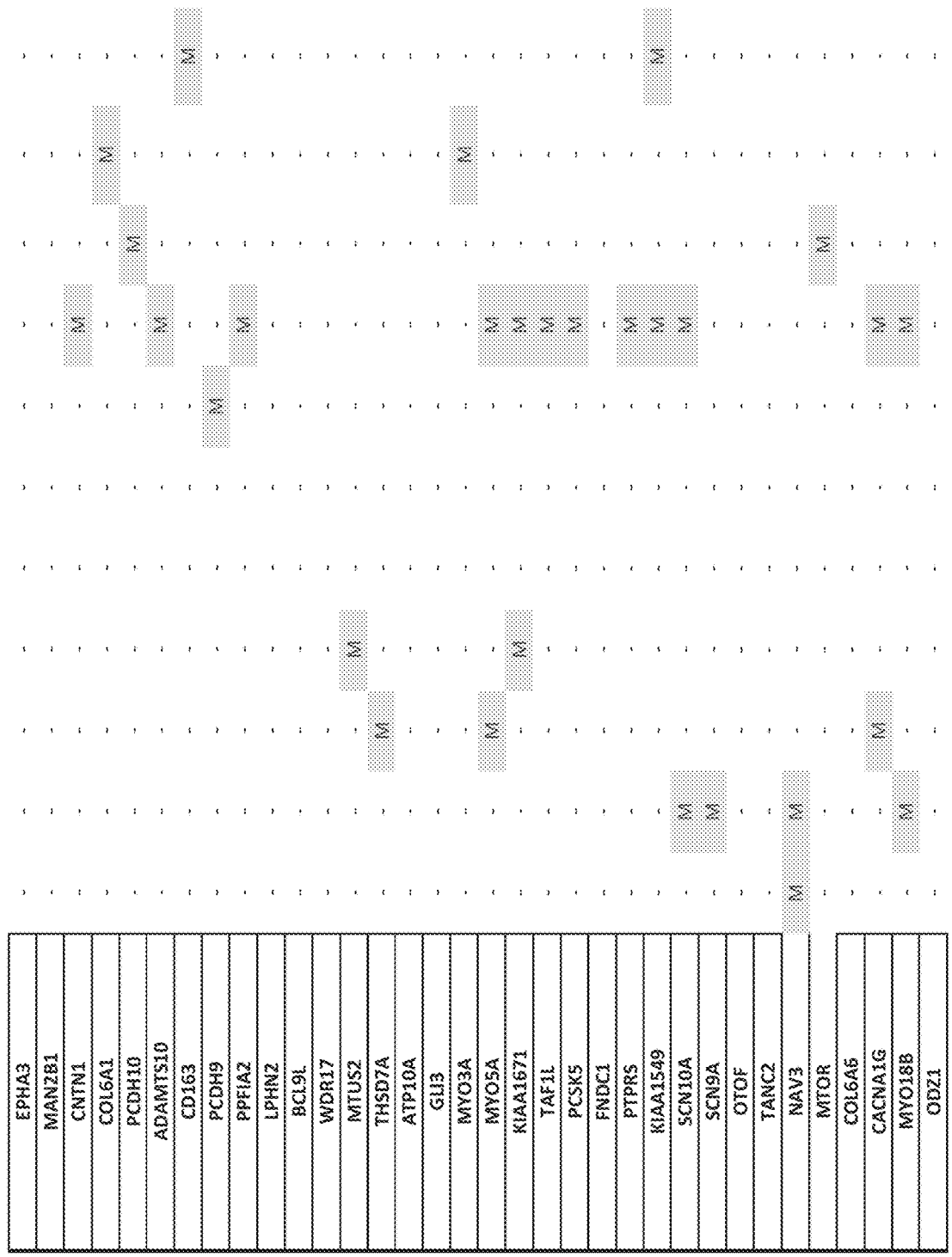
Figure 7H:
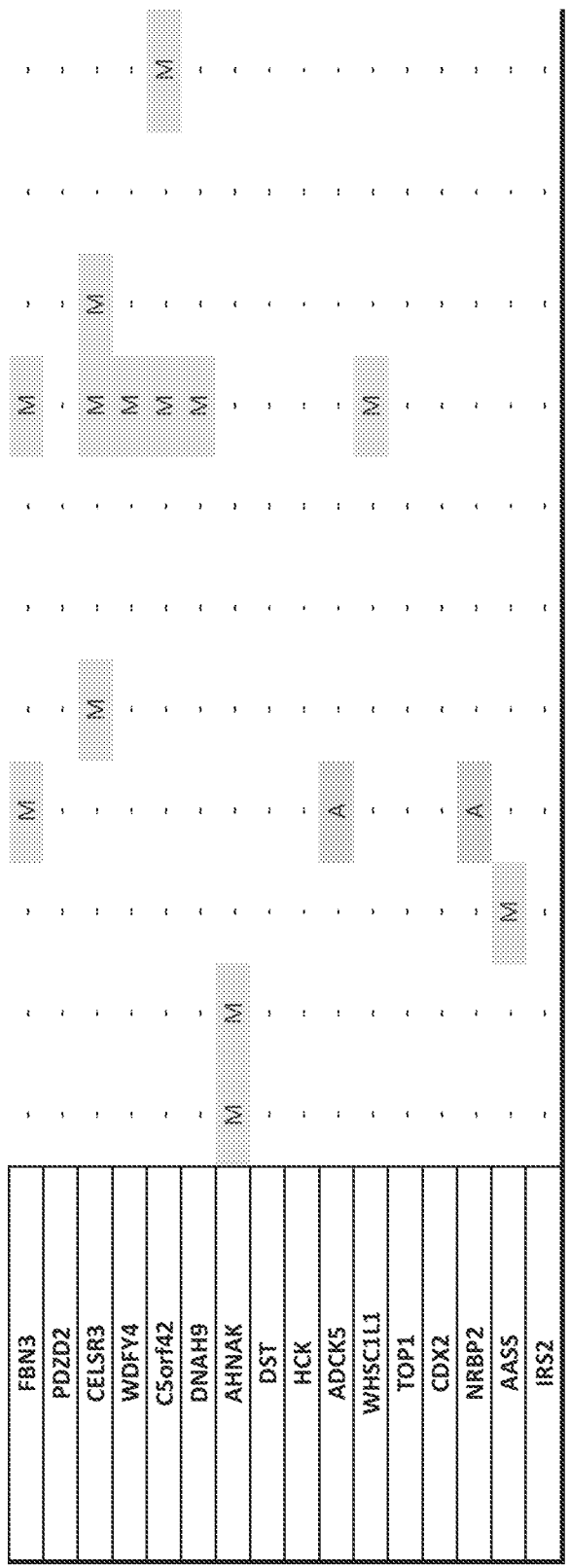
Figure 7I:
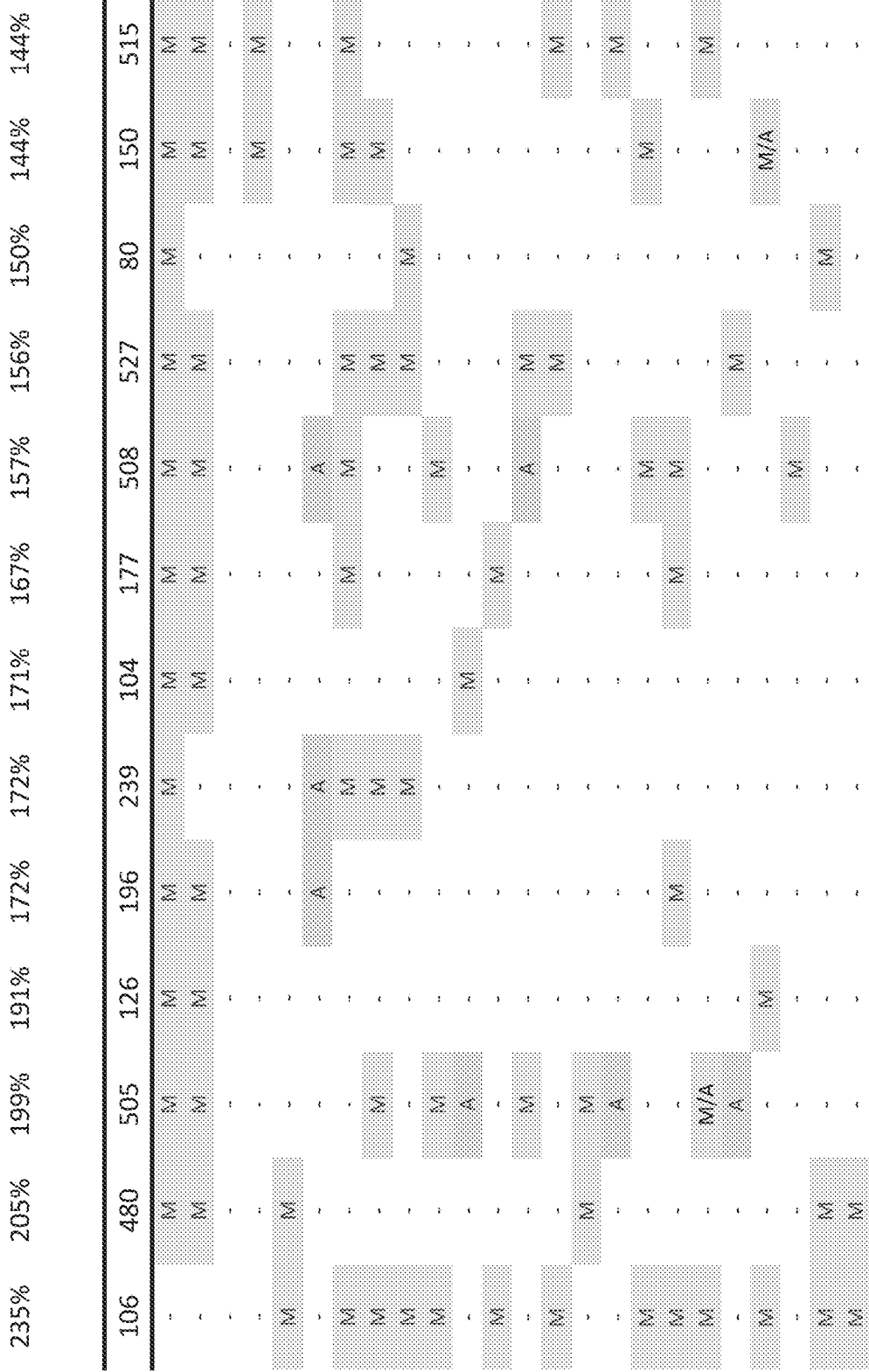
Figure 7J:
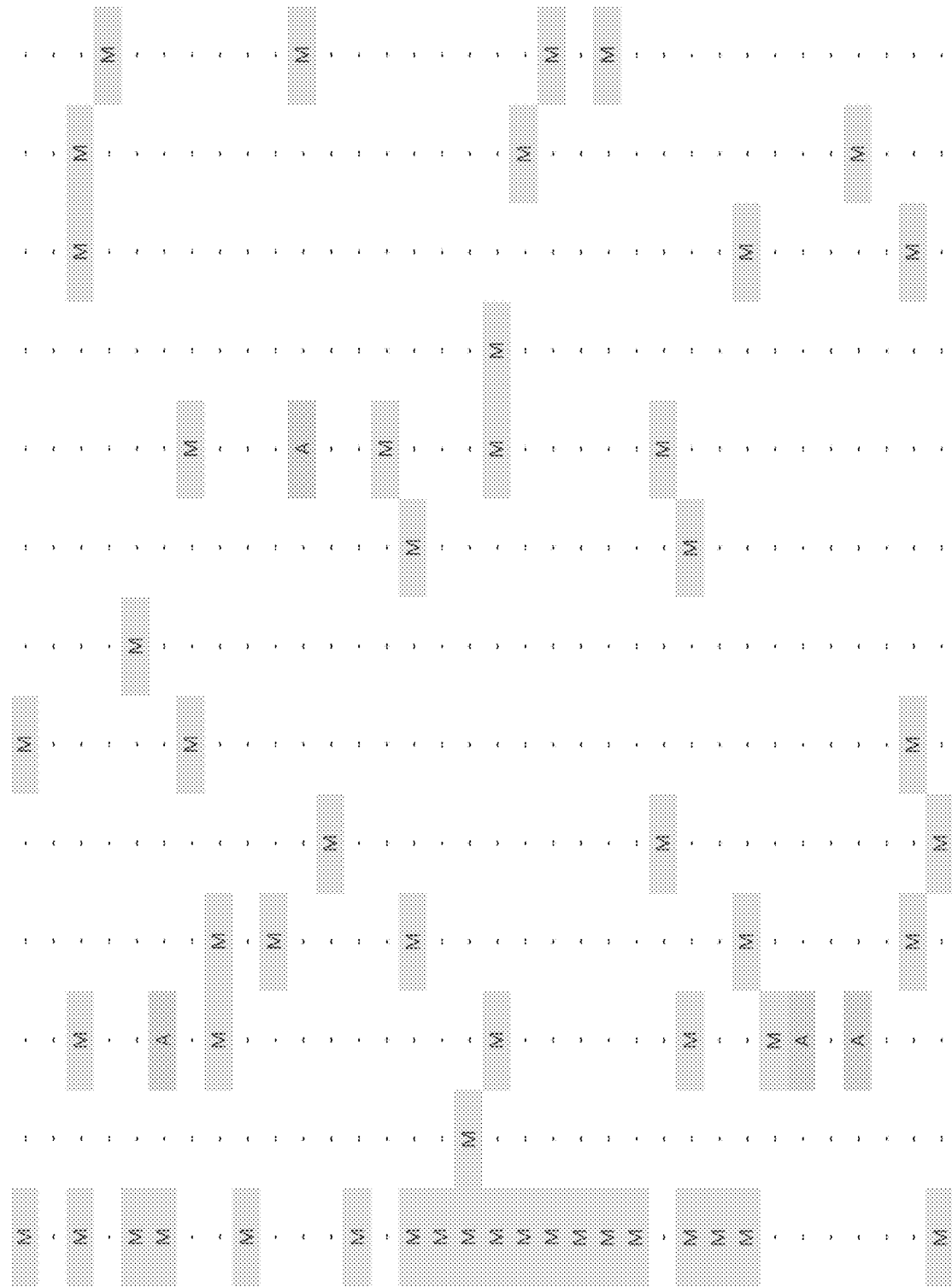
Figure 7K:
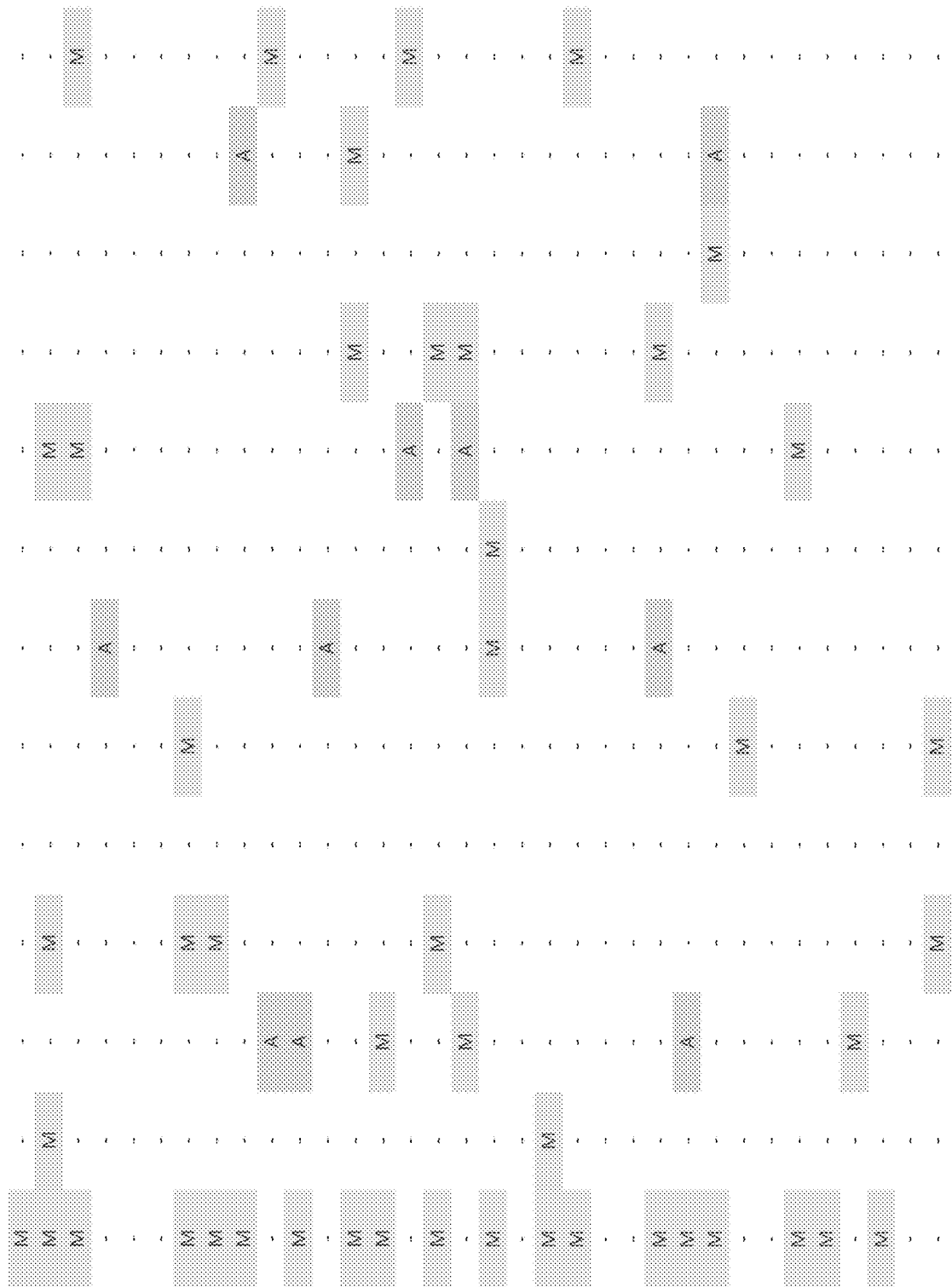
Figure 7L:
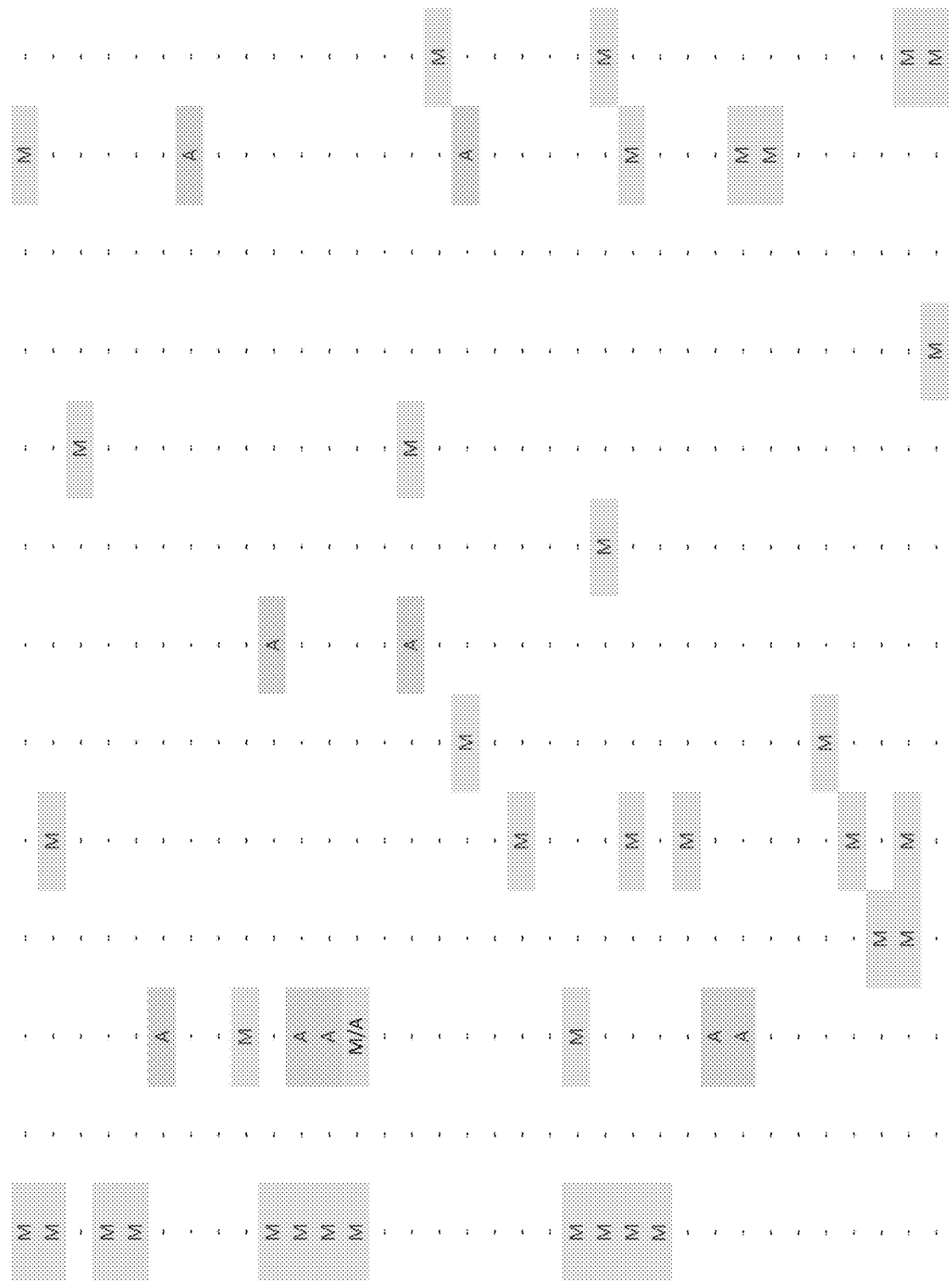
Figure 7M:
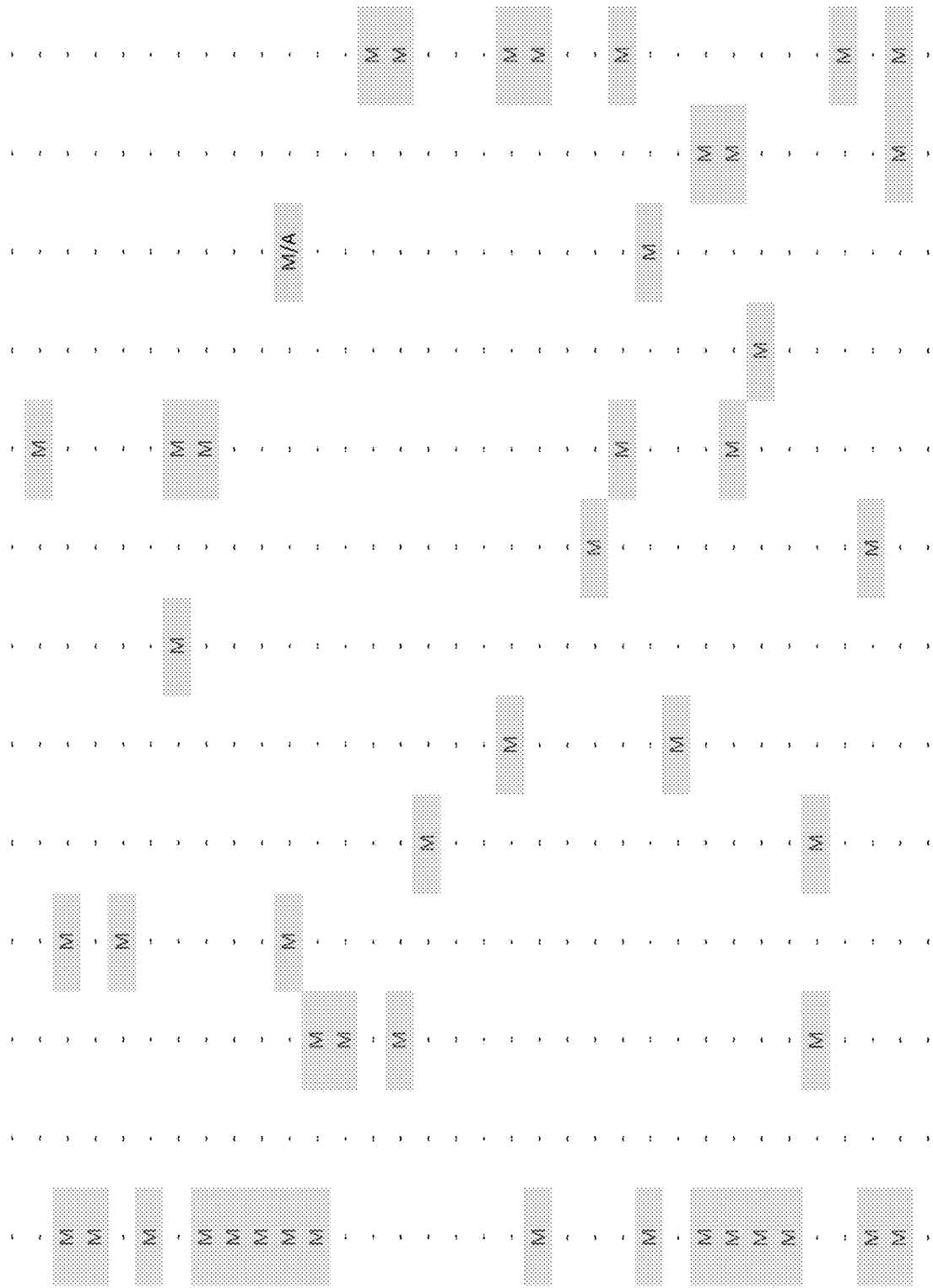
Figure 7N:
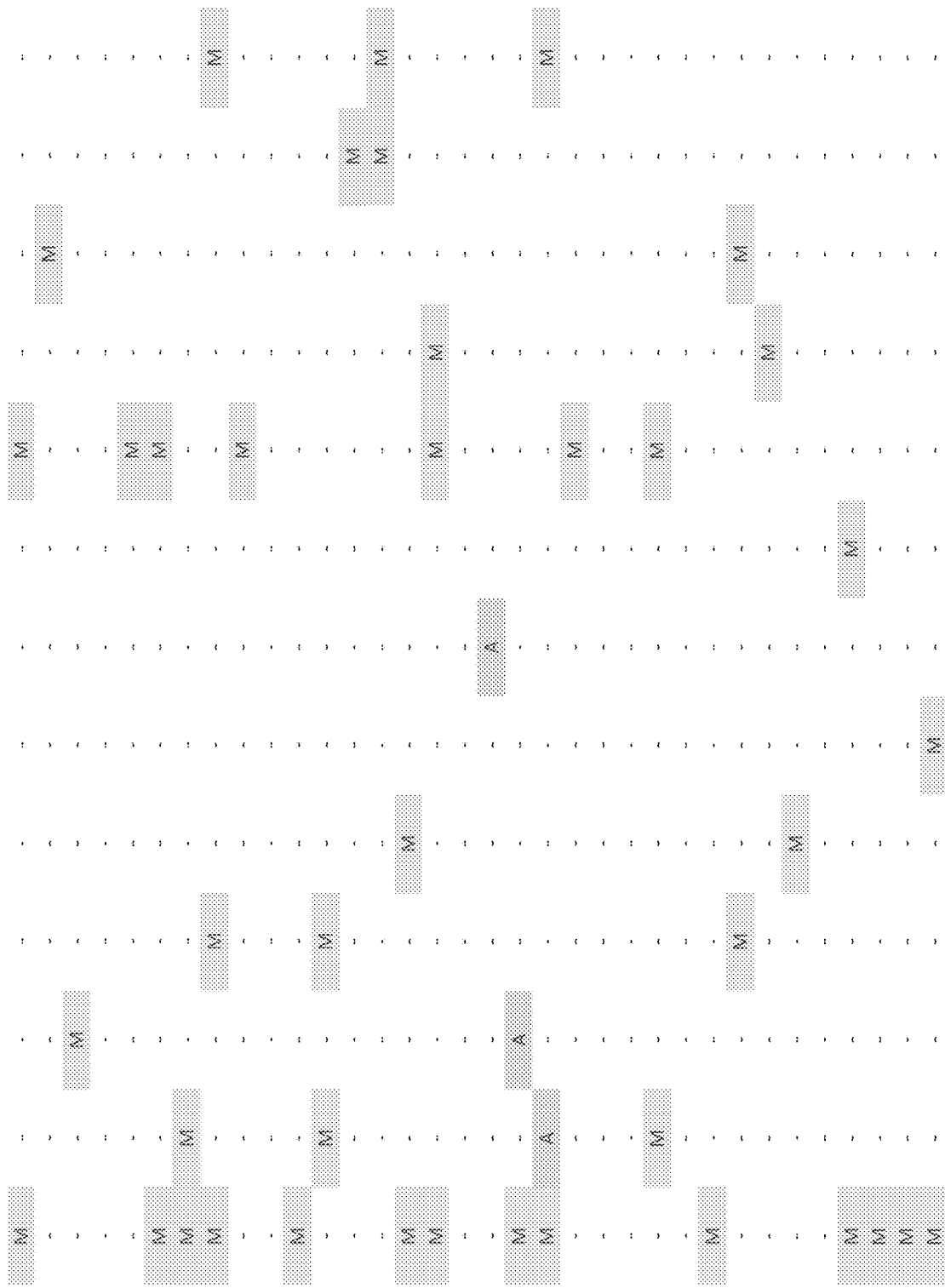
Figure 70:
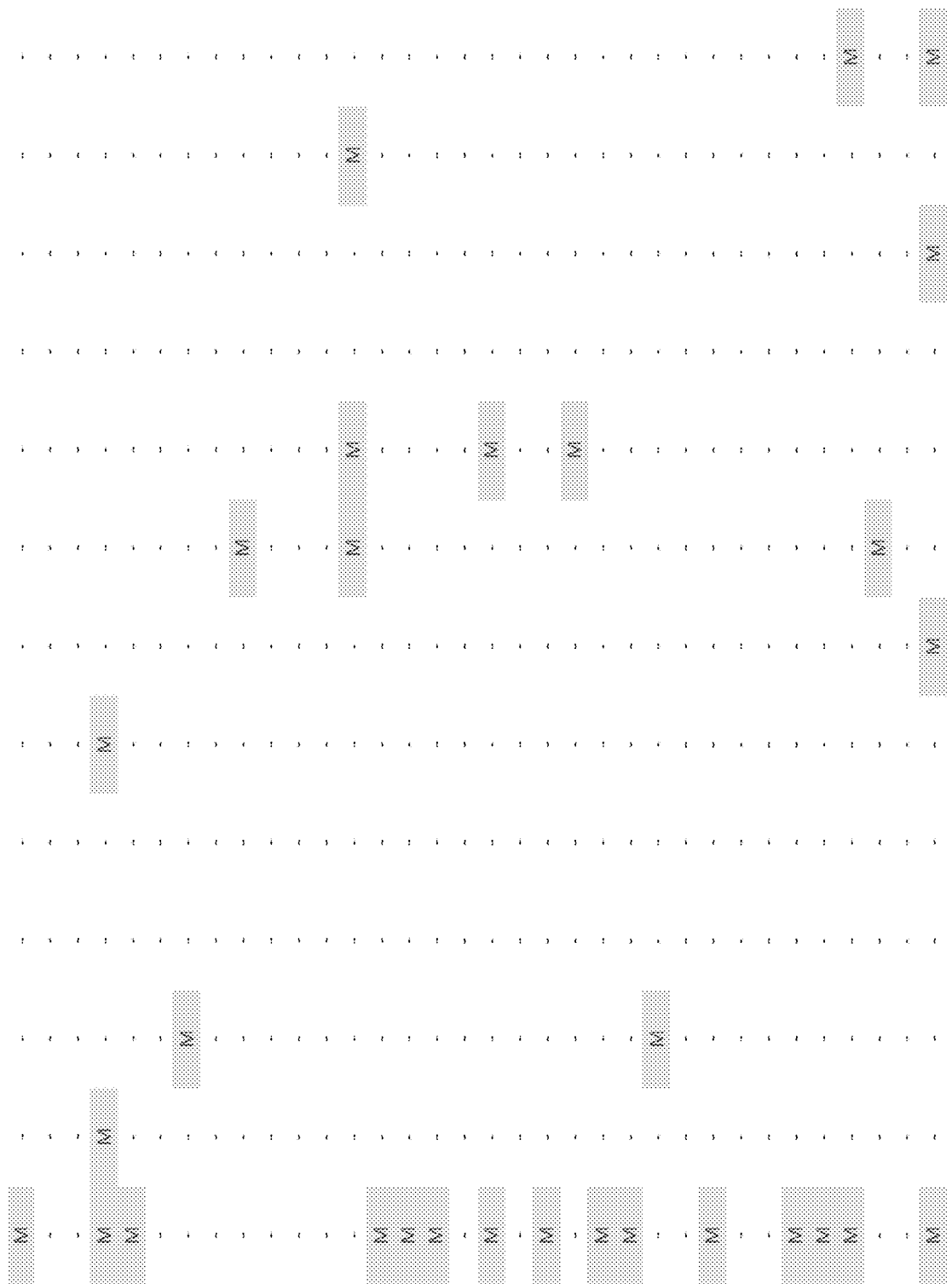
Figure 7P:
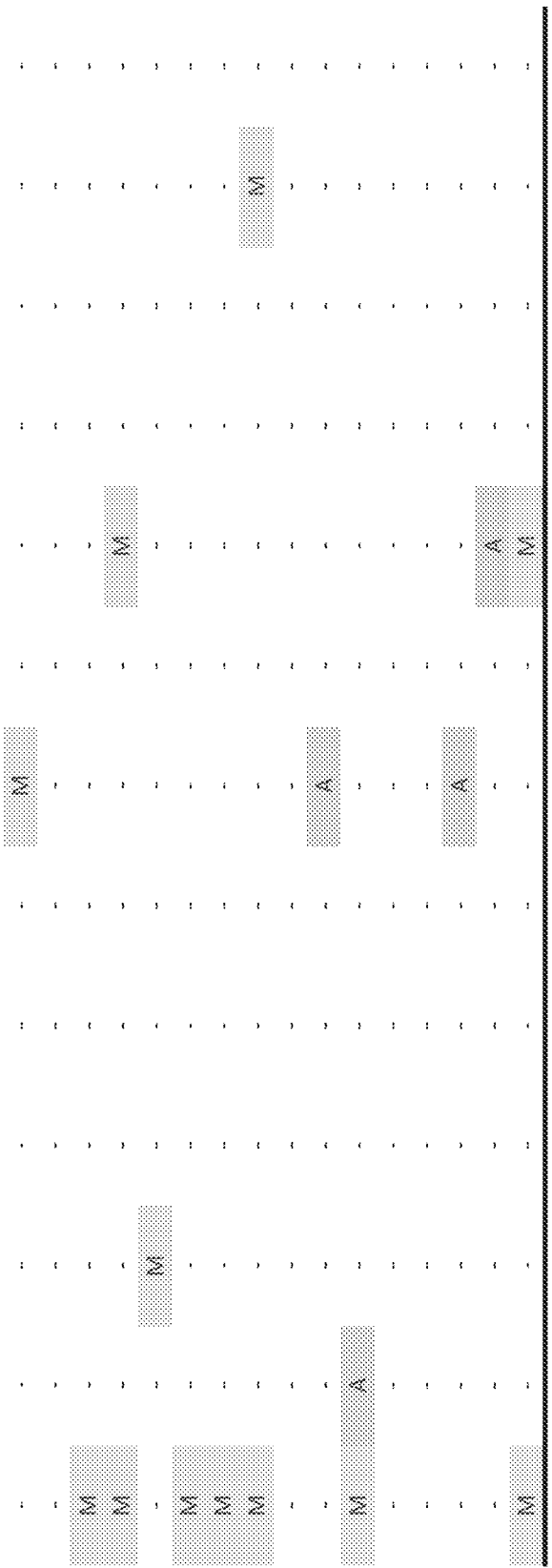
Figure 7Q:
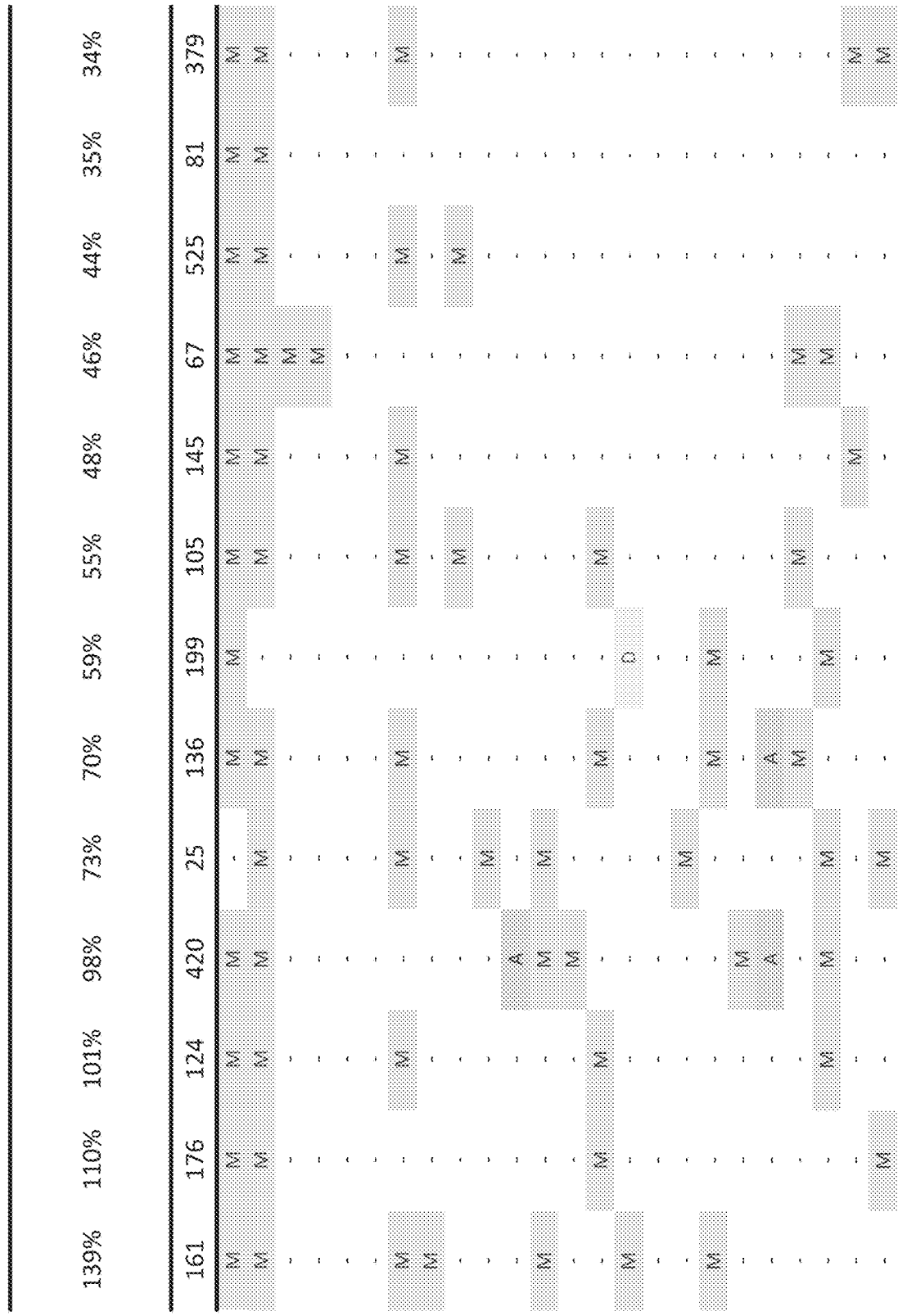
Figure 7R:
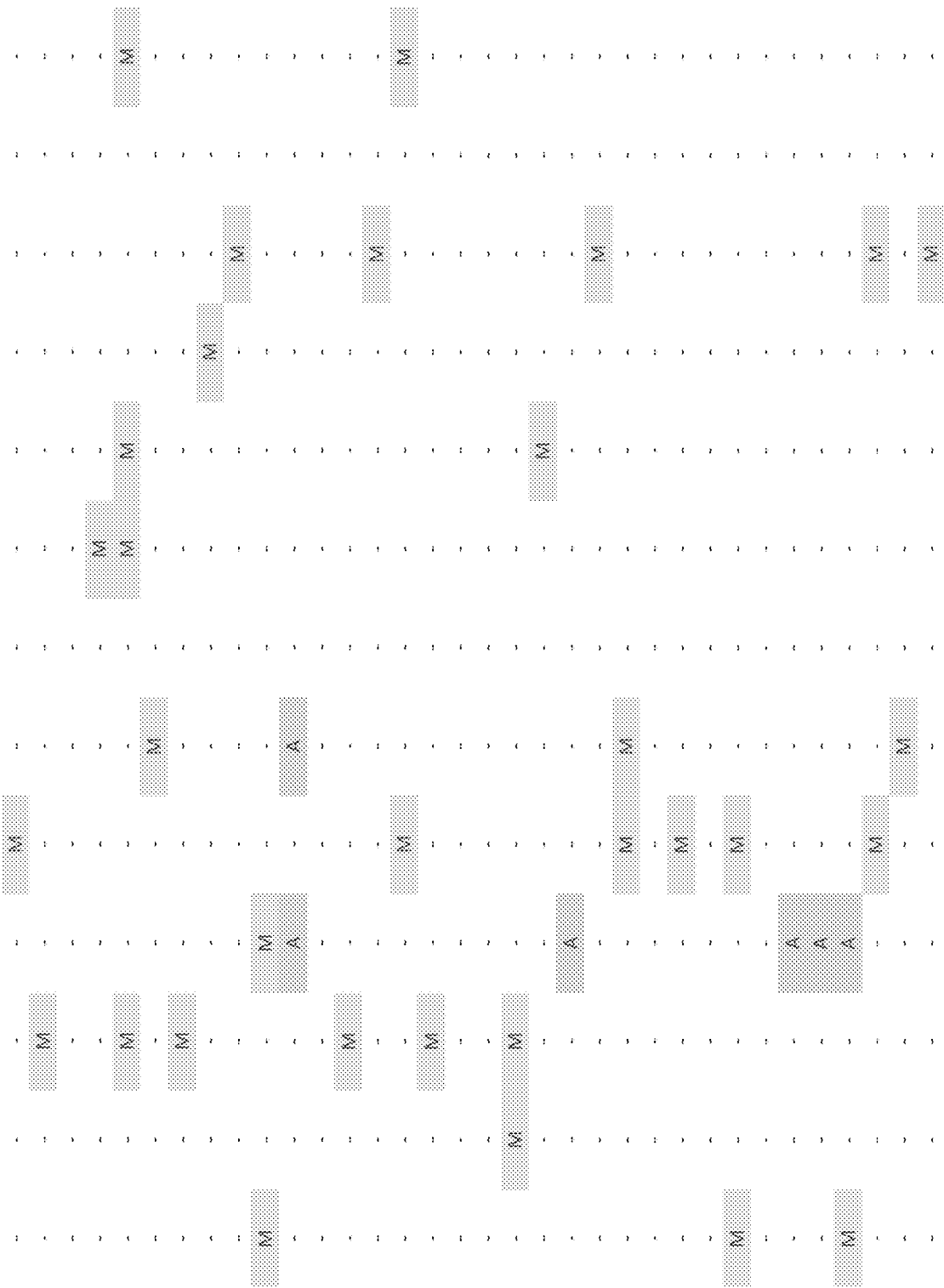
Figure 7S:
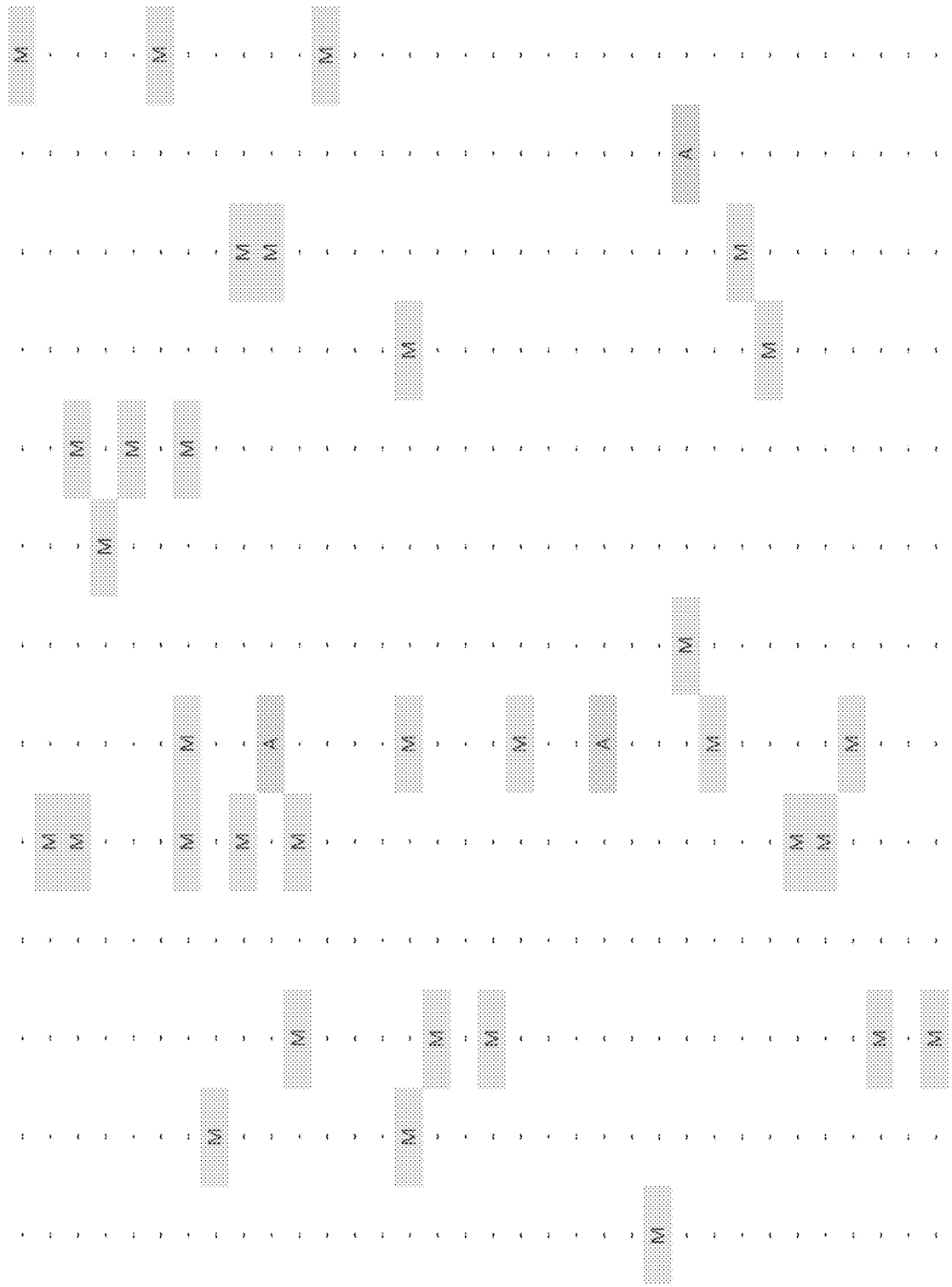
Figure 7T:
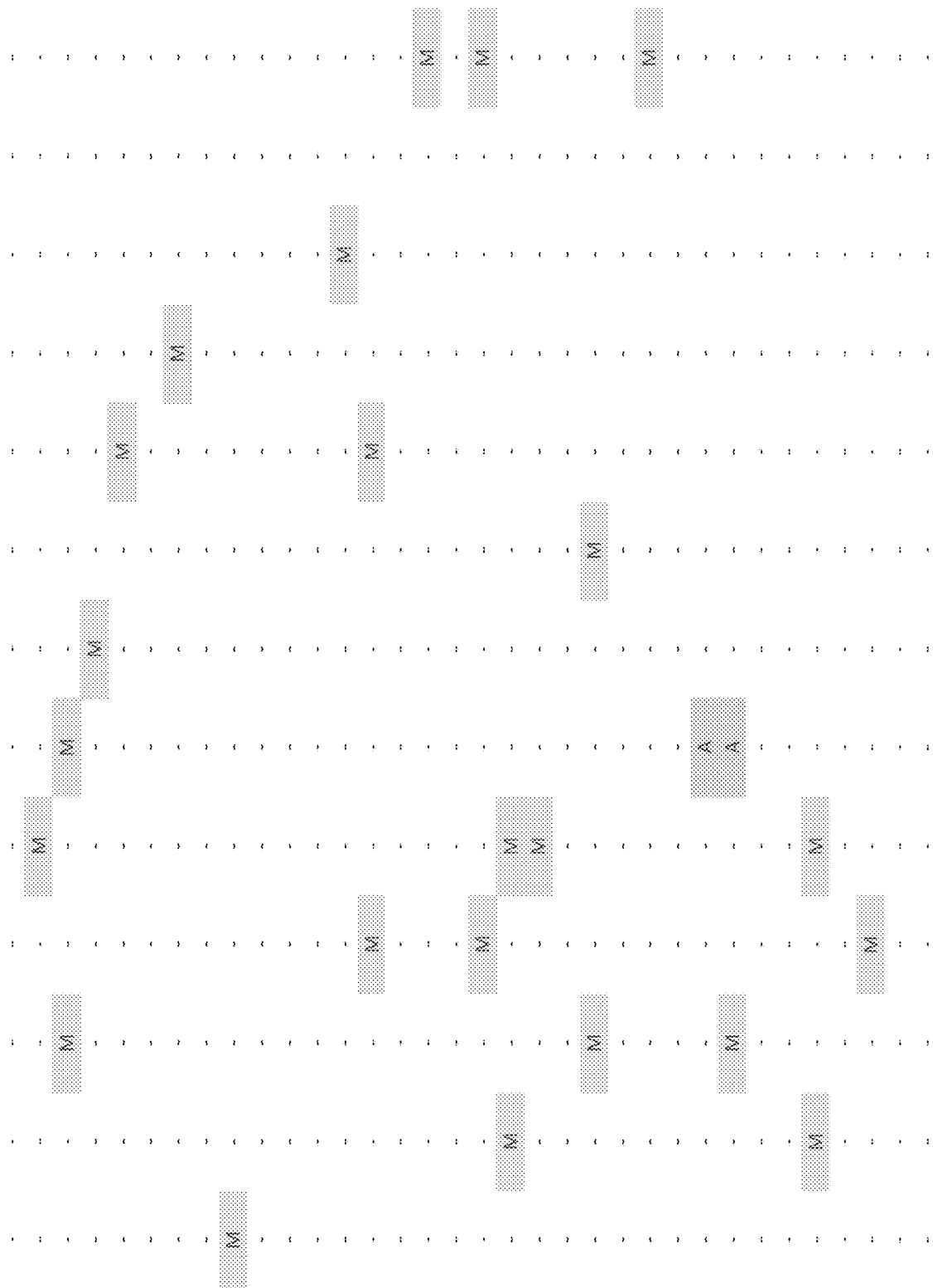
Figure 7U:
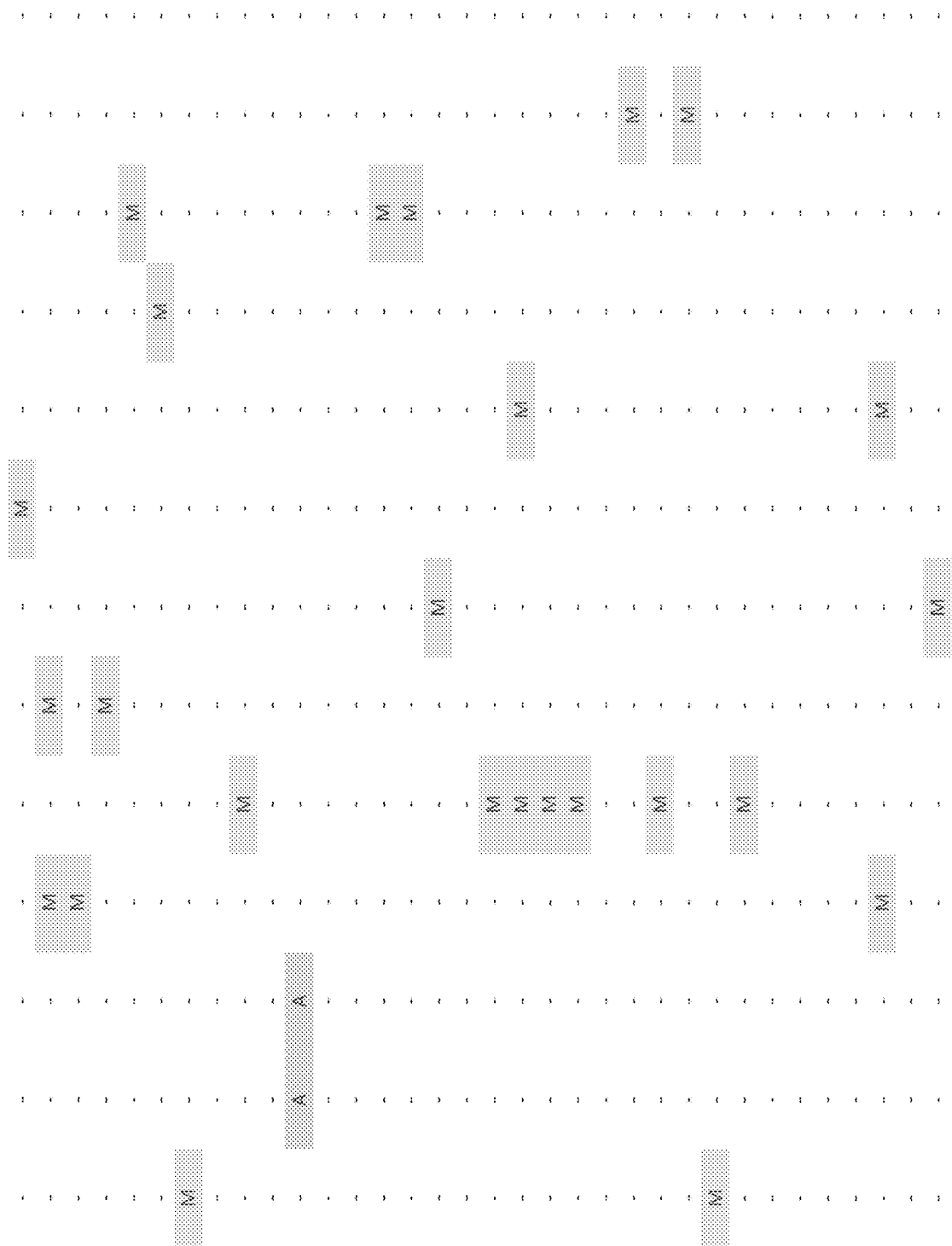
Figure 7V:
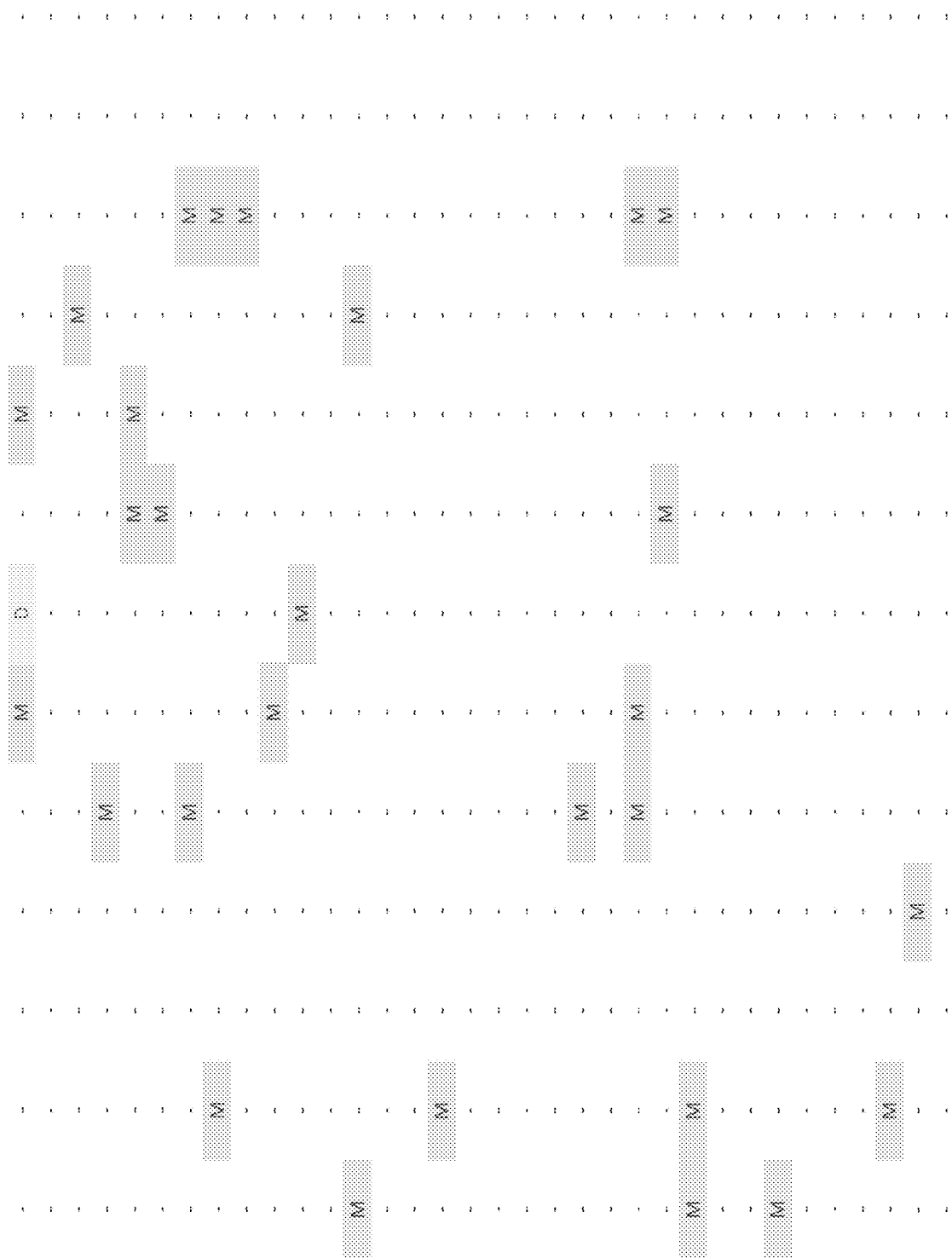
Figure 7W:
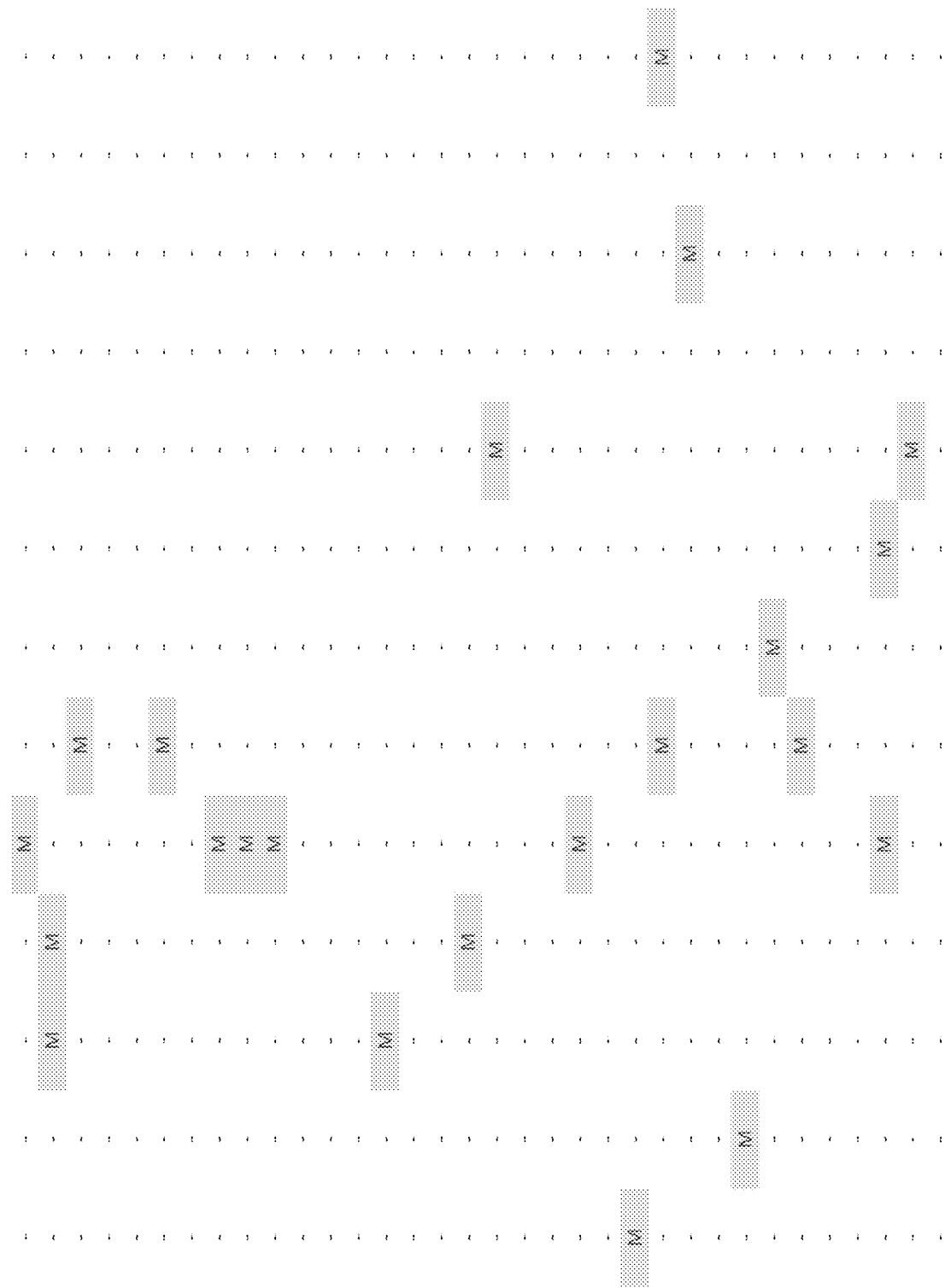
Figure 7X:
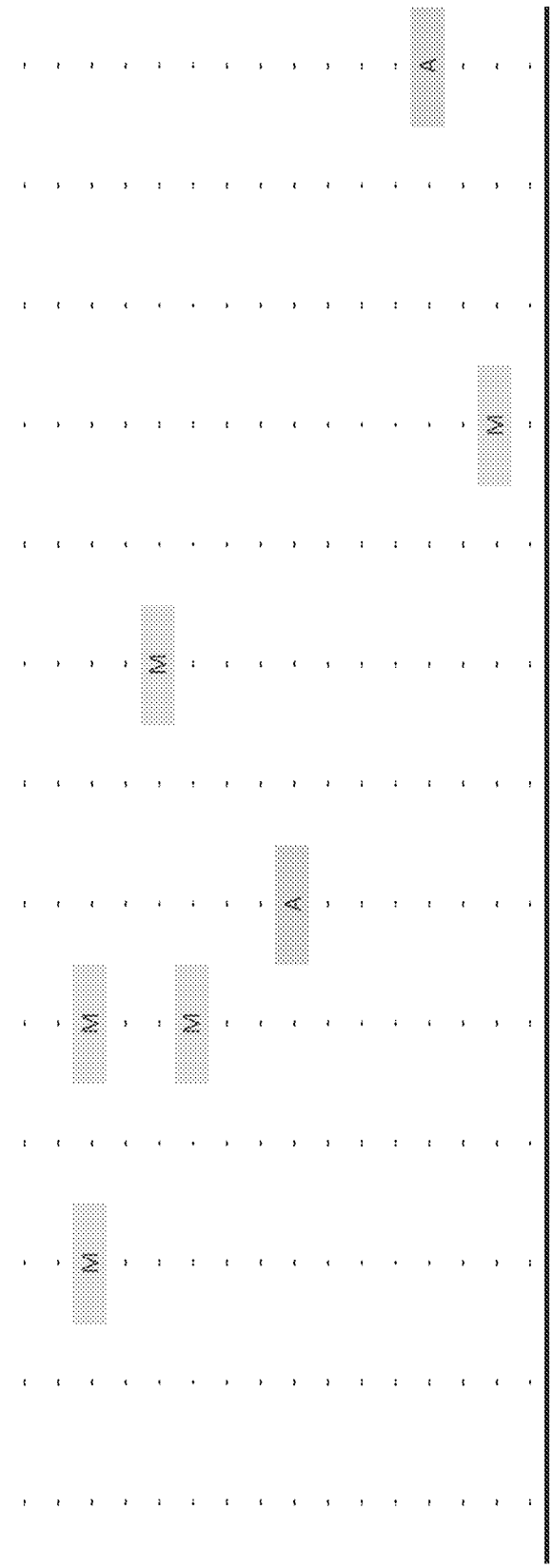
Figure 7Y:
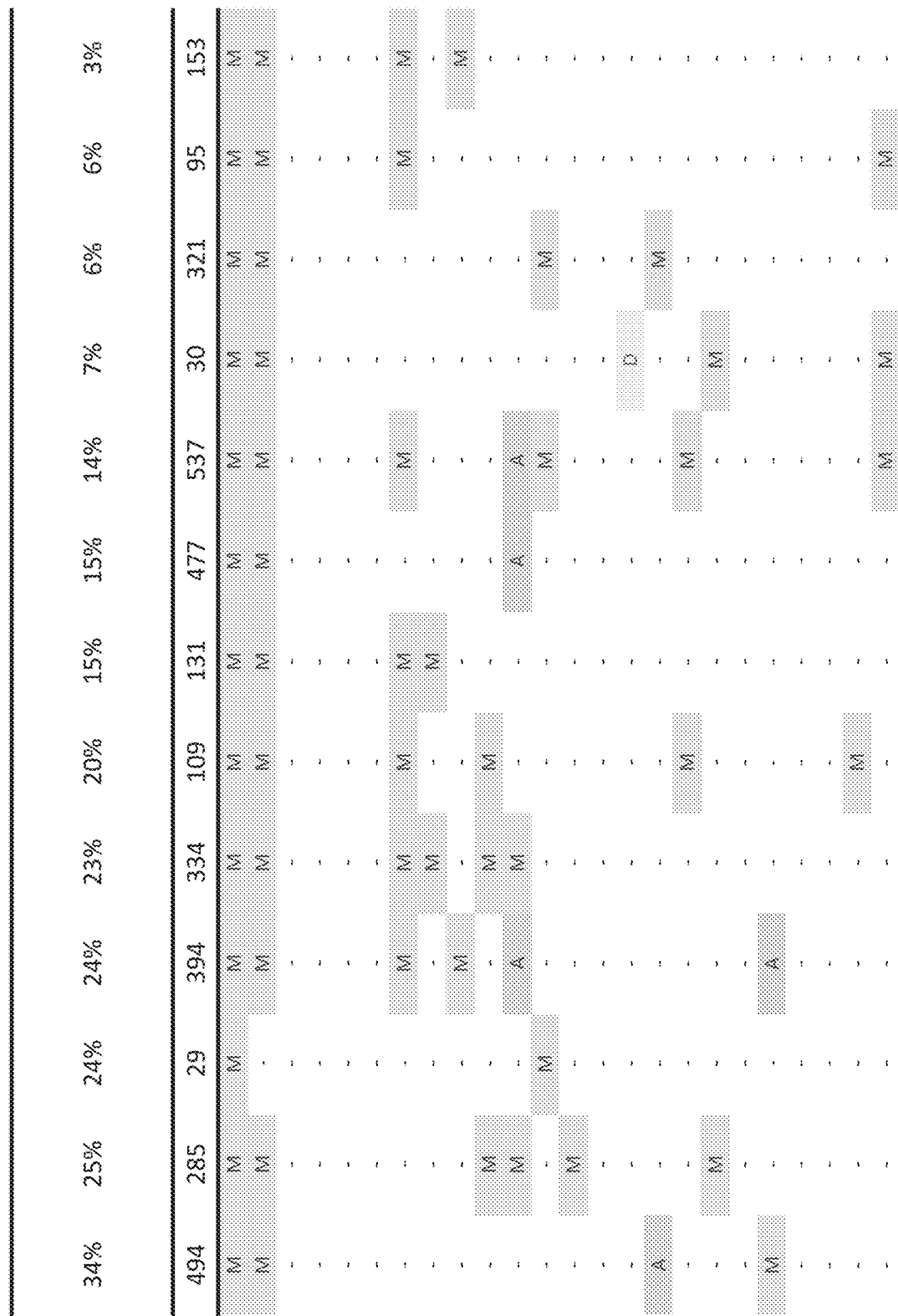
Figure 7Z:
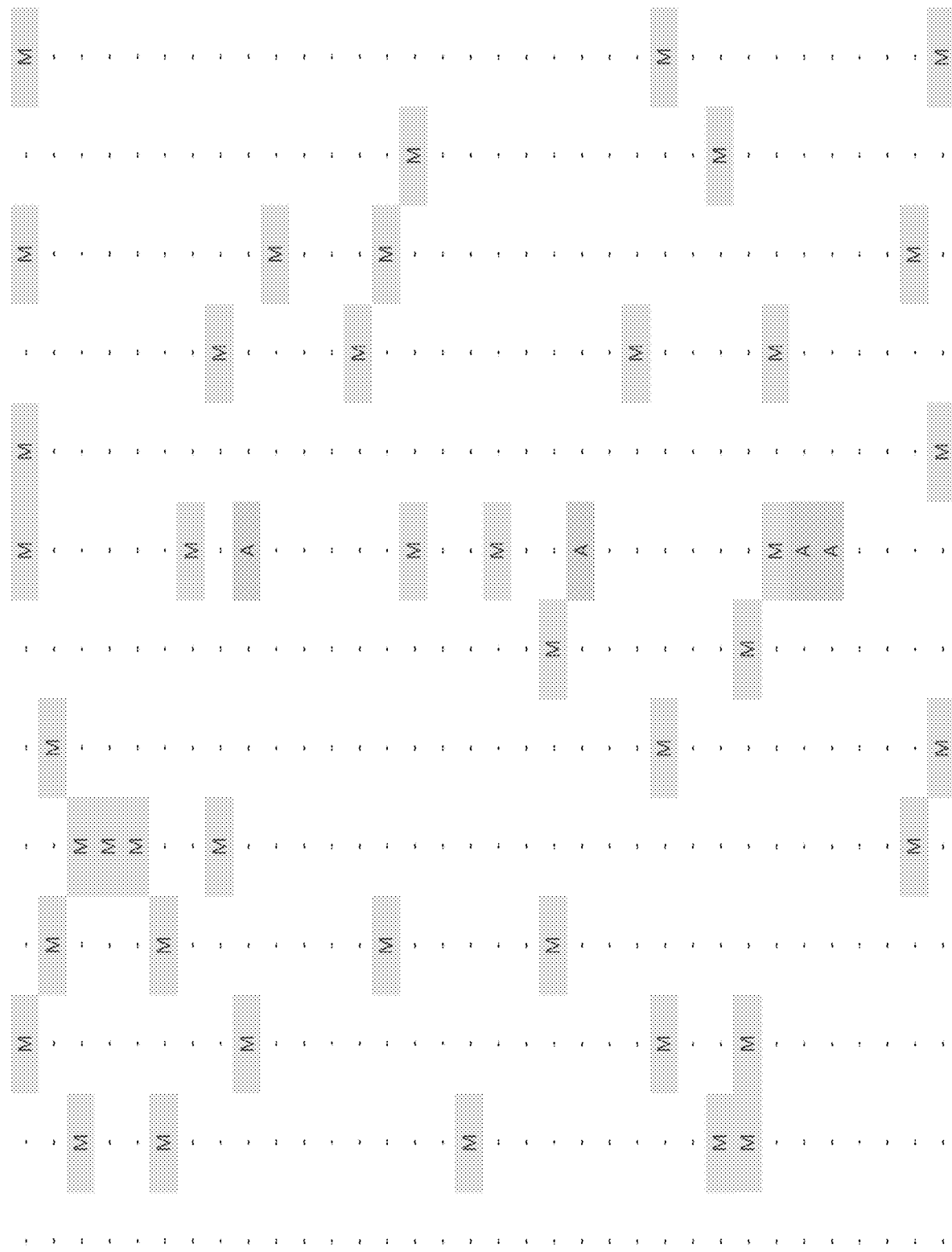
Figure 7A:
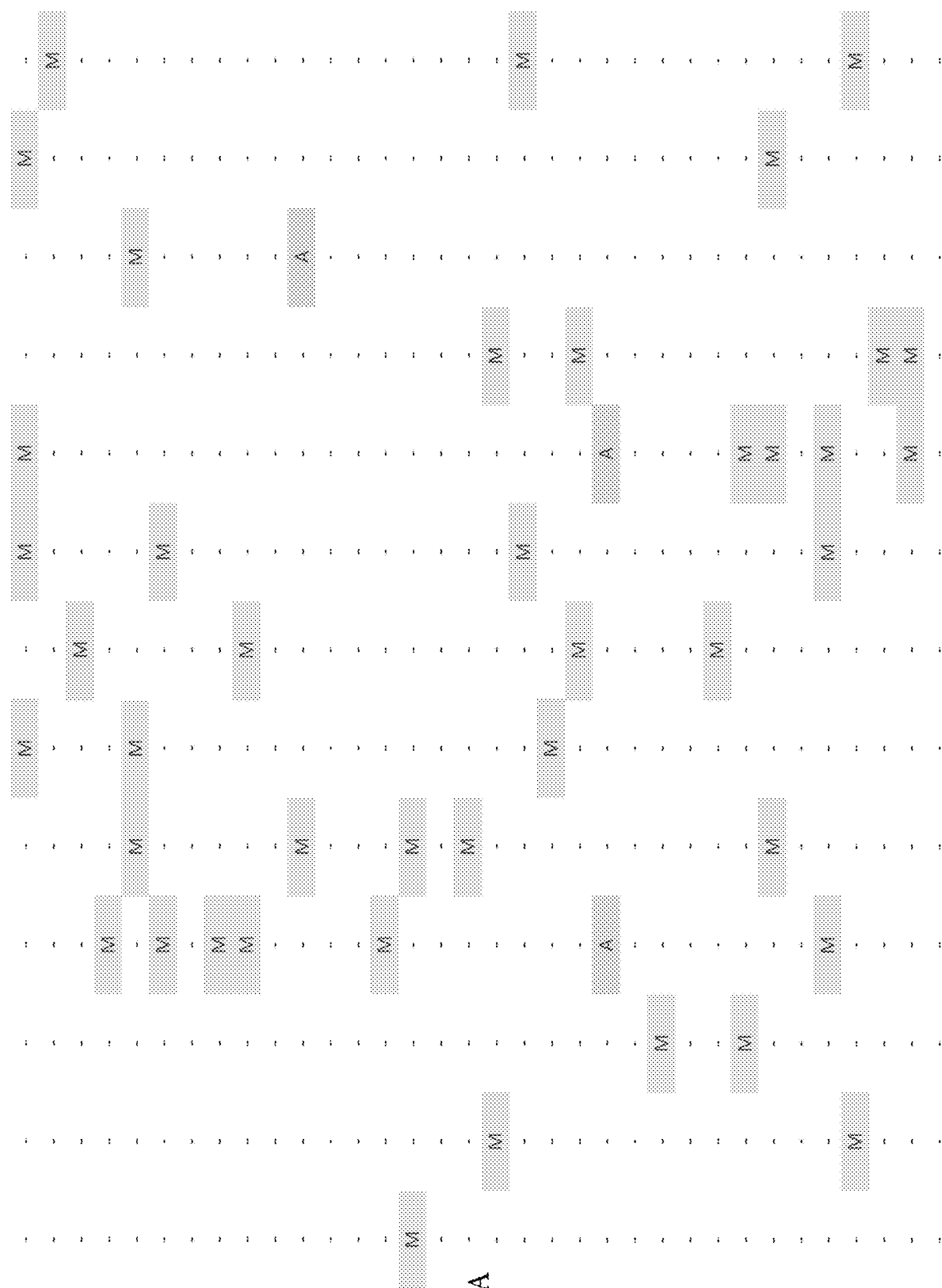
Figure 7B:
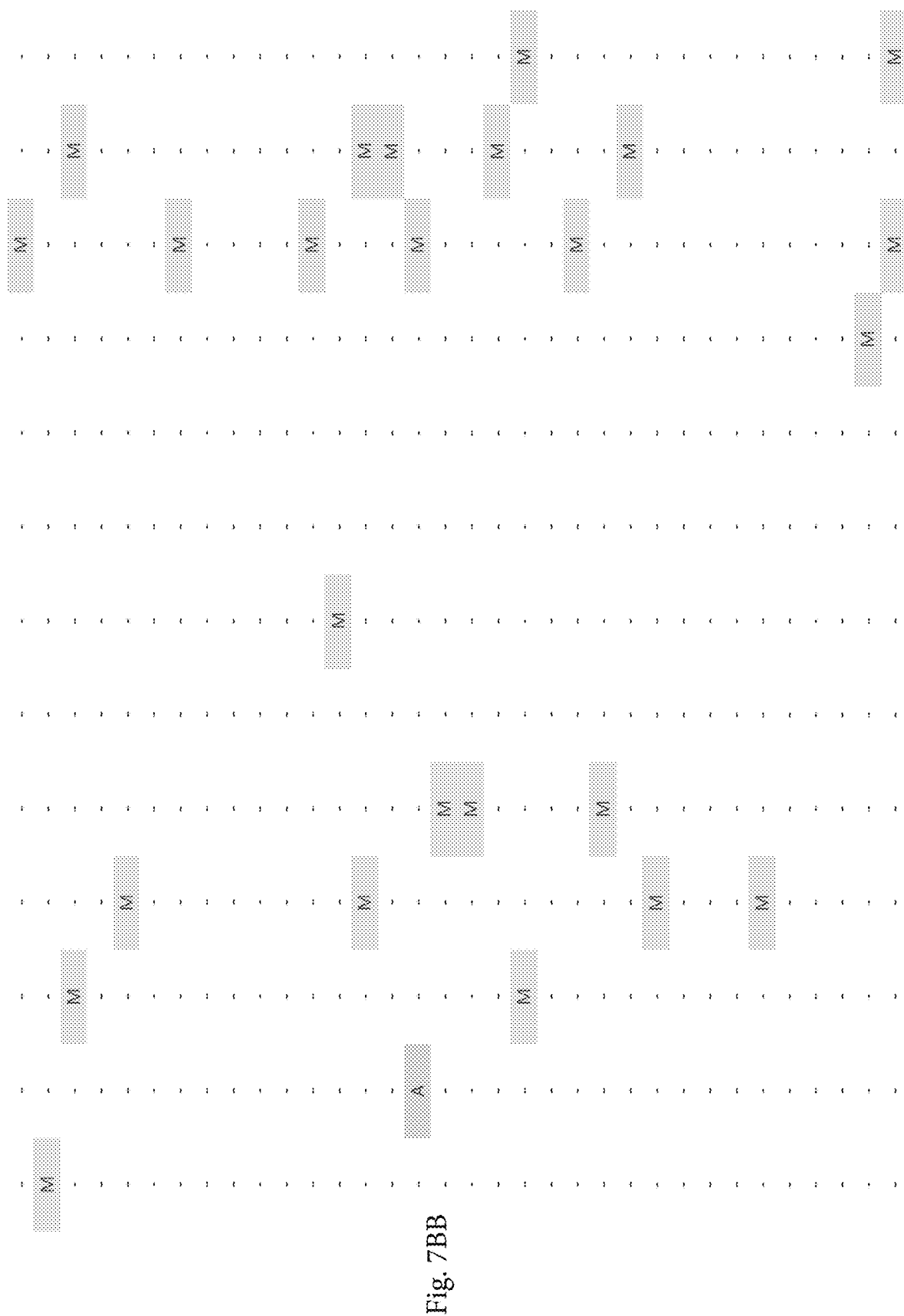
Figure 7C:
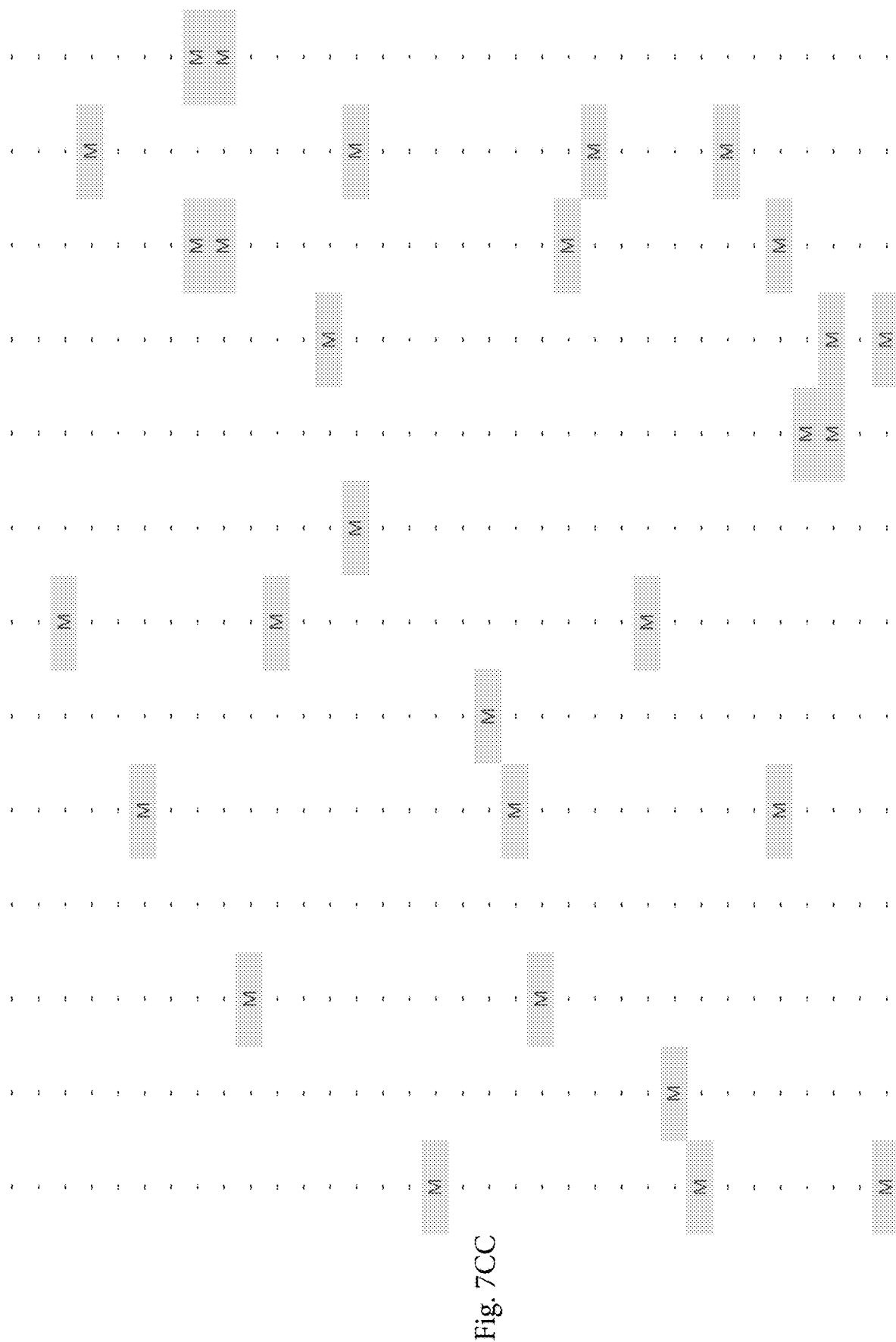
Figure 7D:
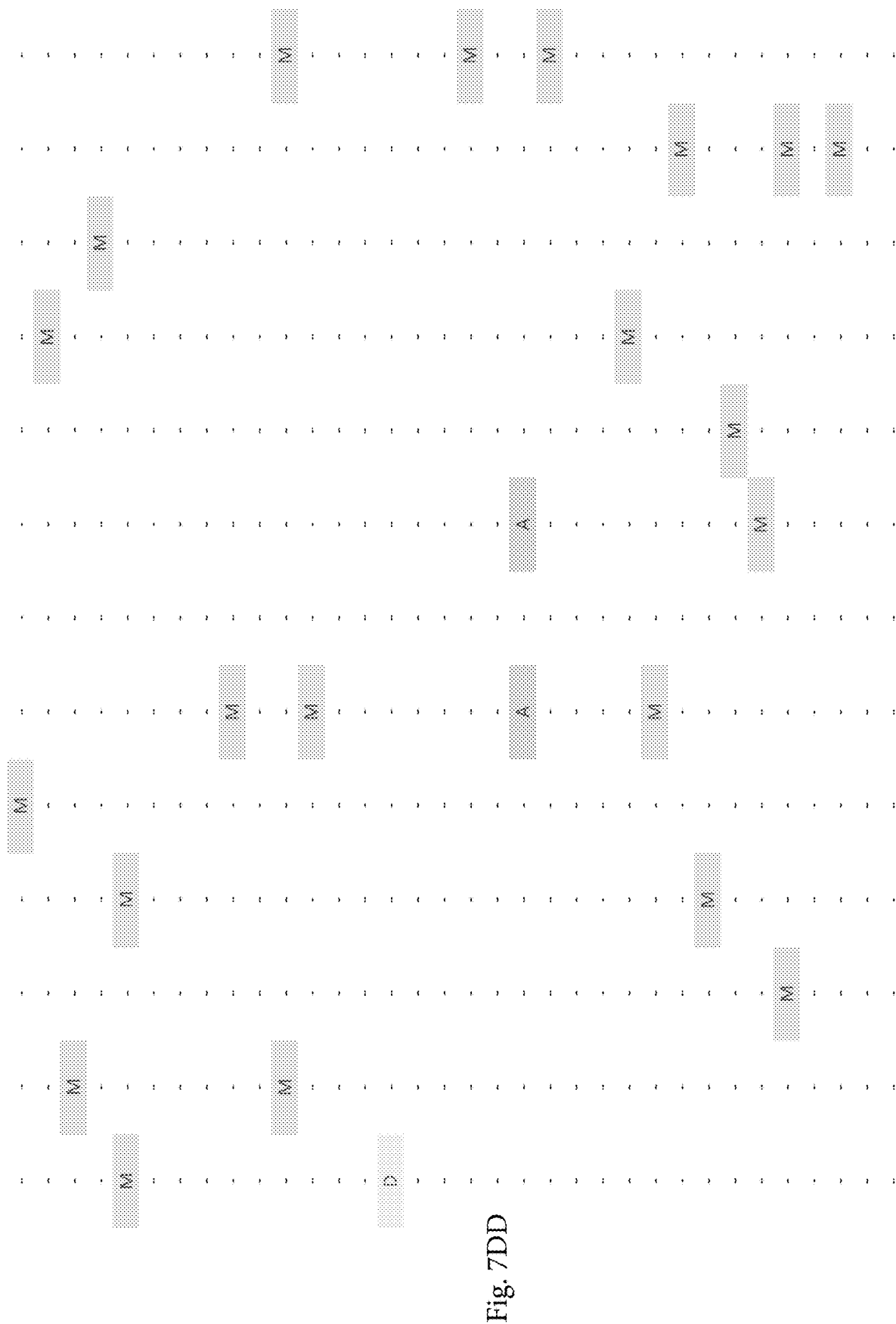
Figure 7E:
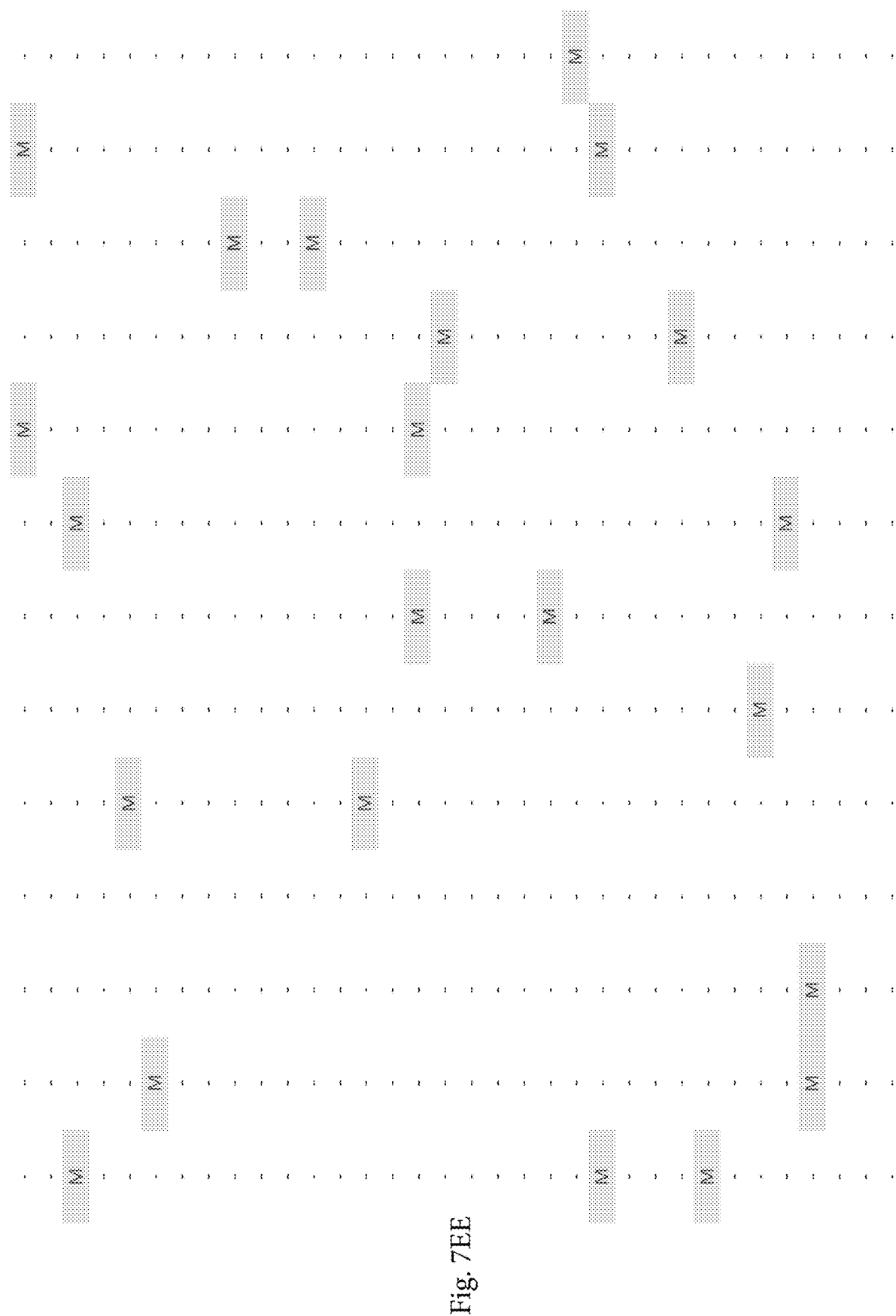
Figure 7F:
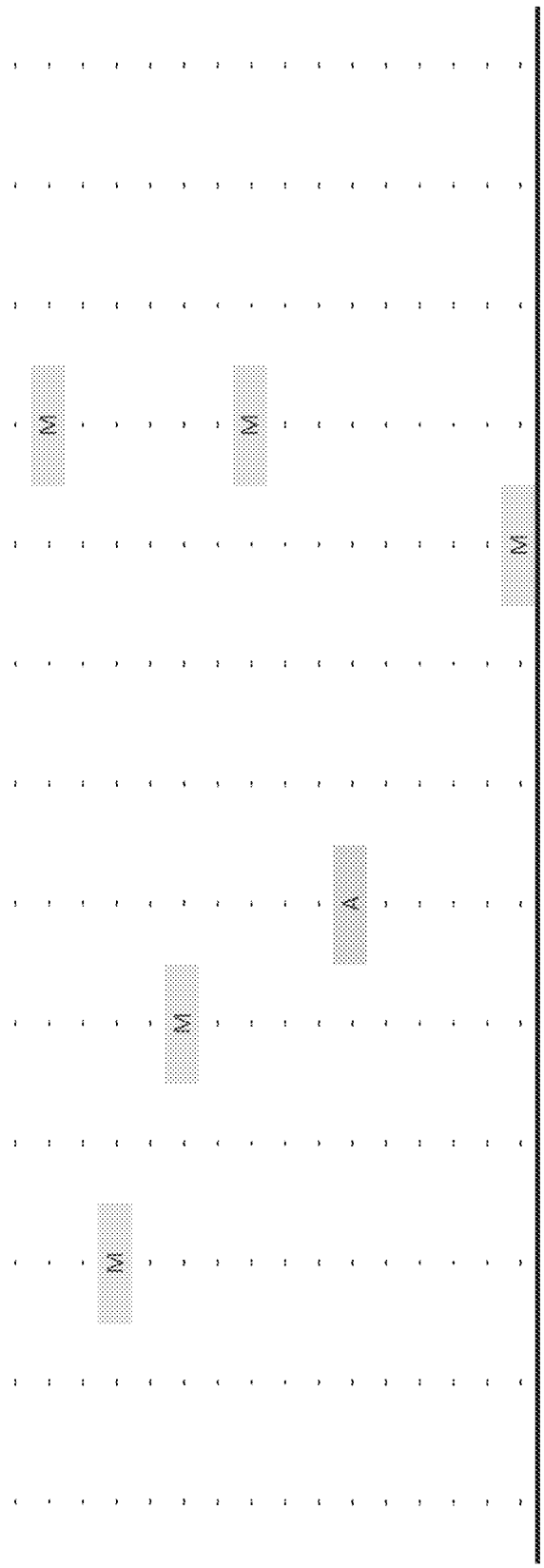
Figure 7G:
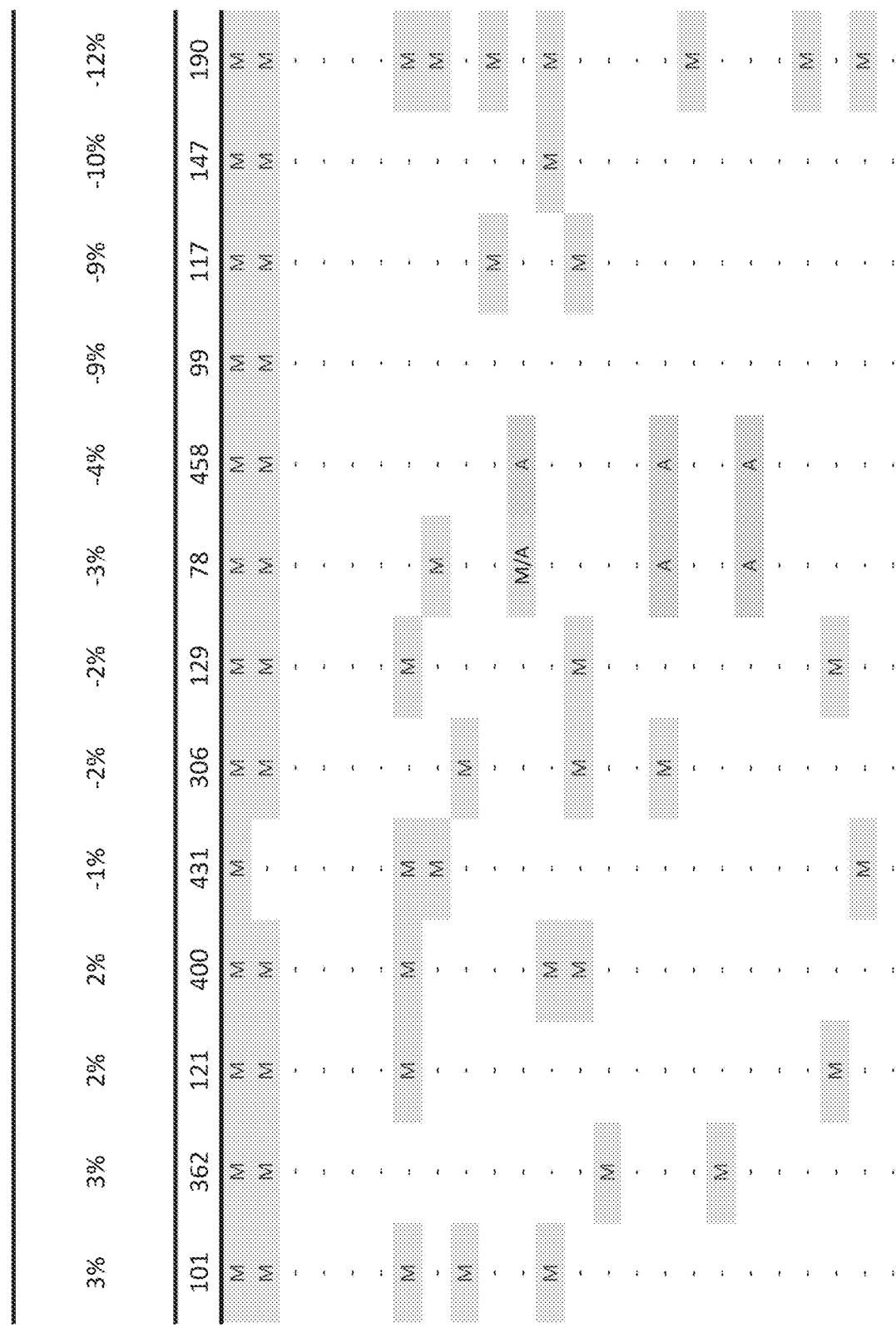
Figure 7H:
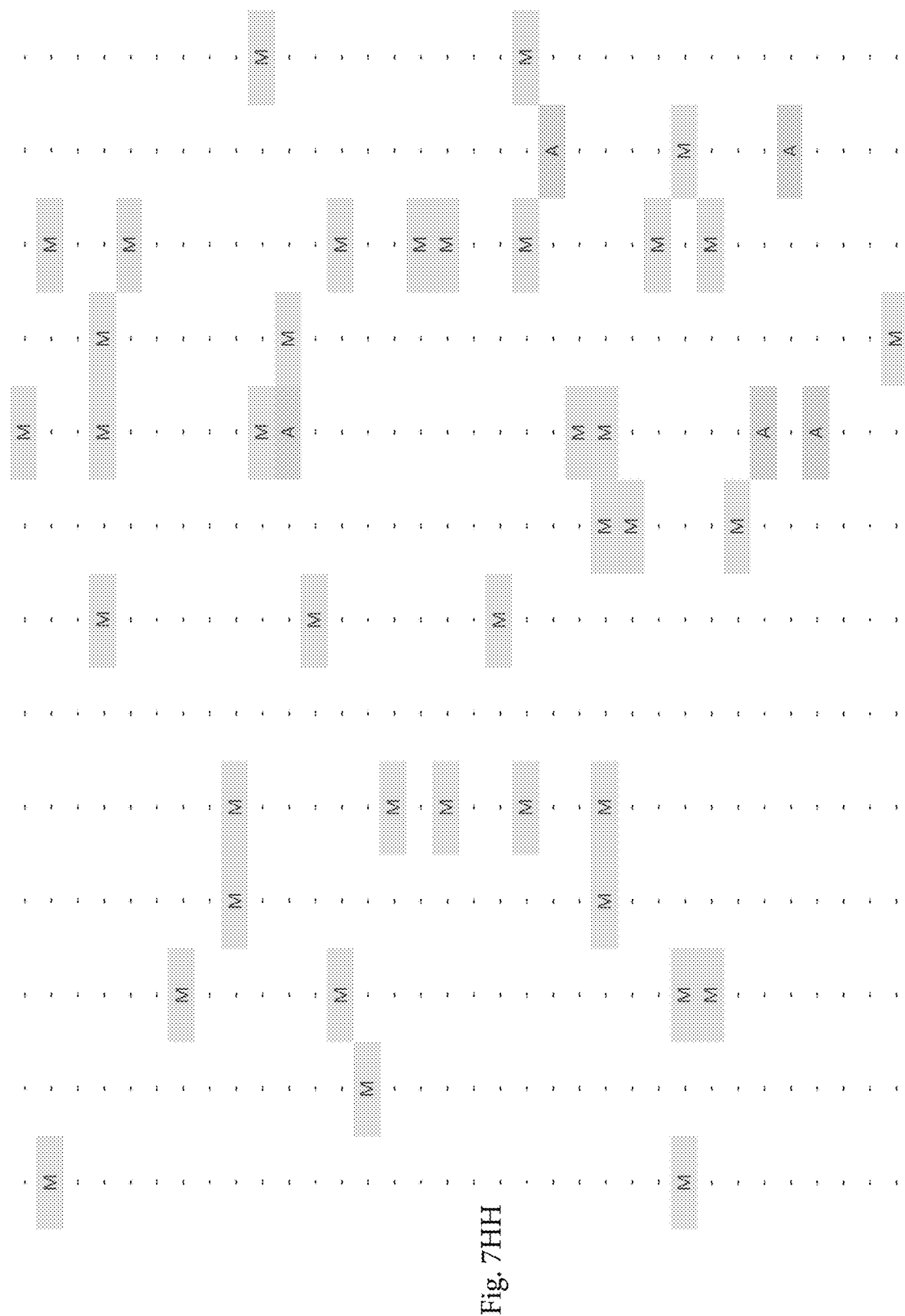
Figure 7I:
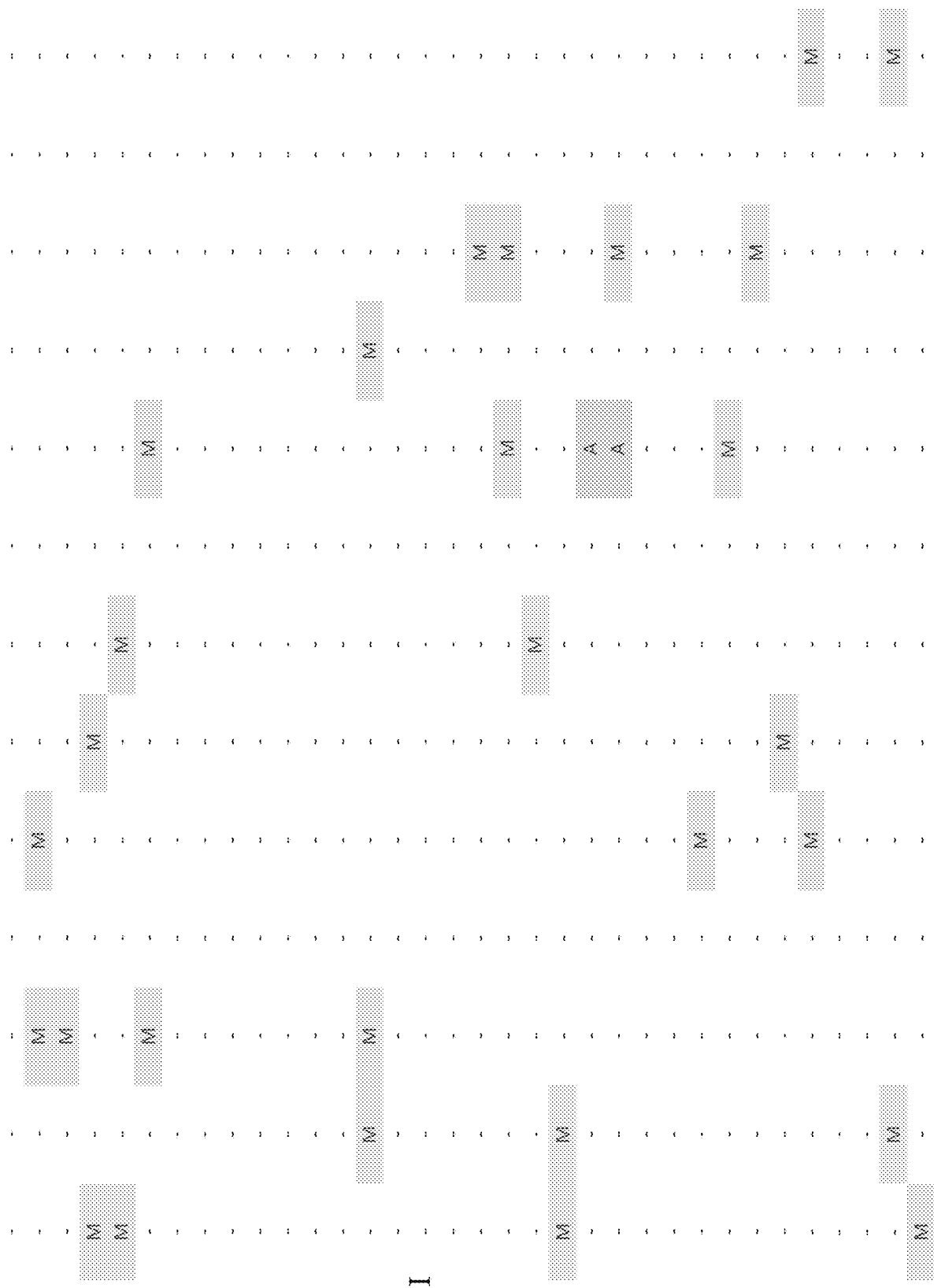
Figure 7J:
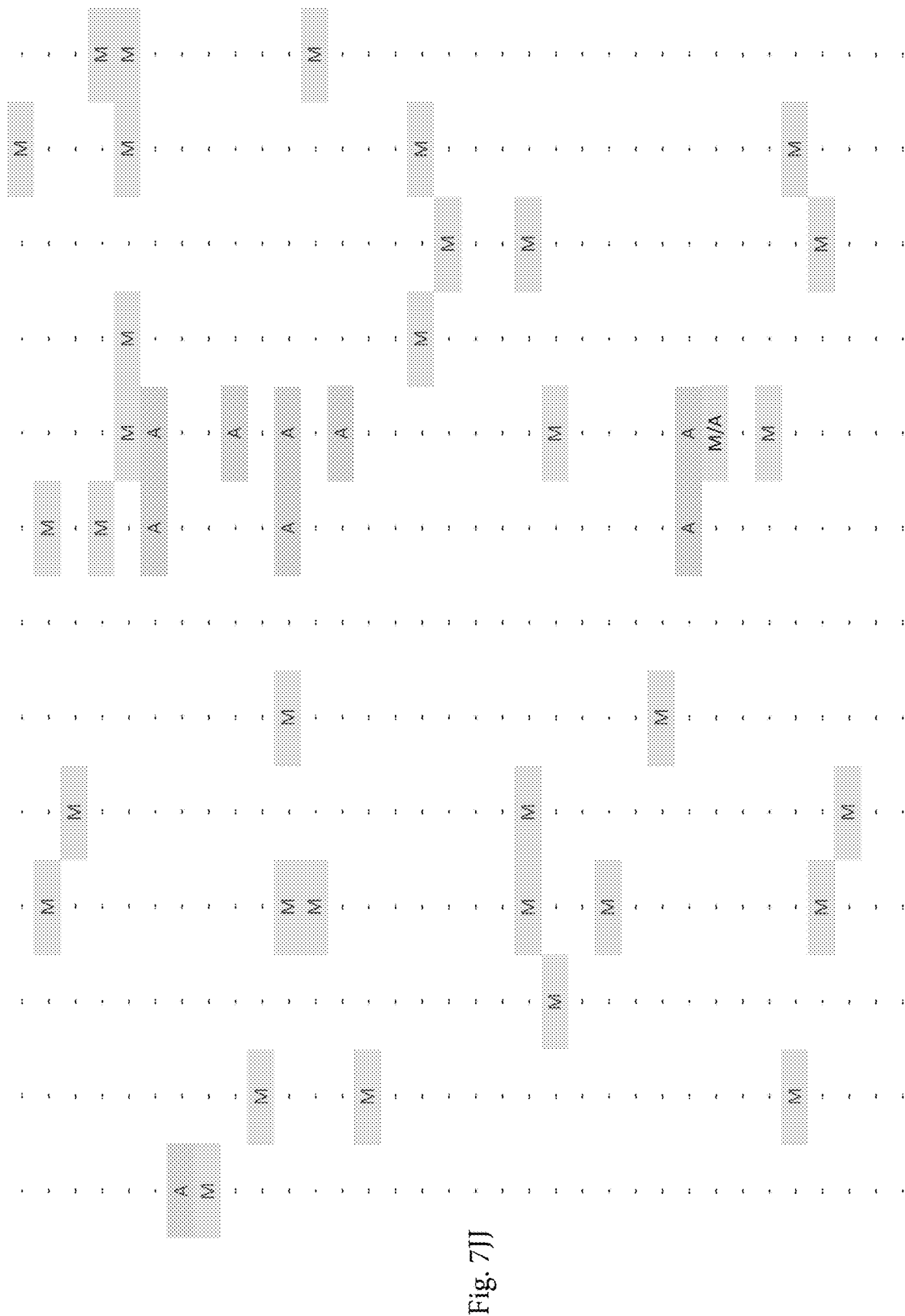
Figure 7K:
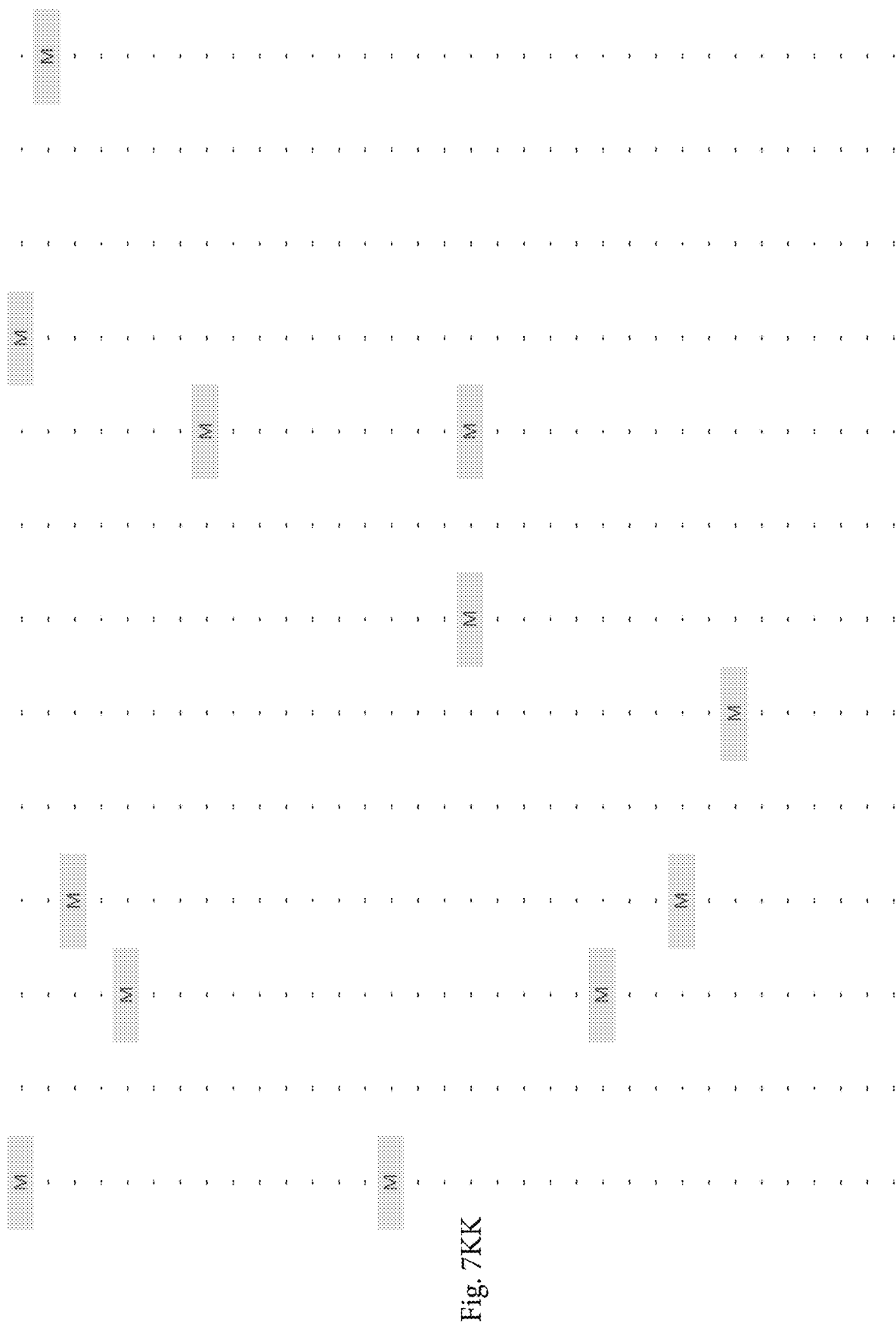
Figure 7L:
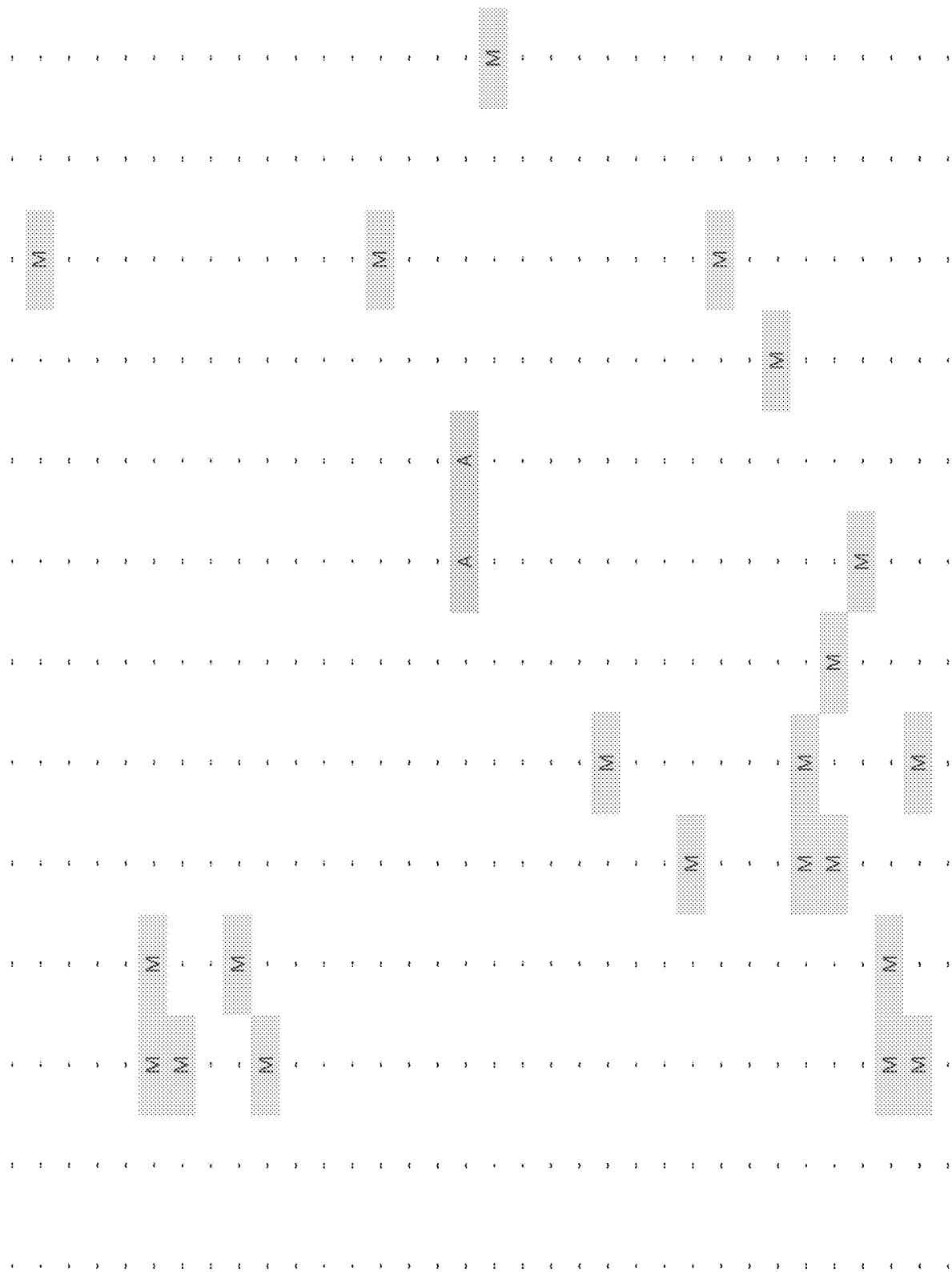
Figure 7M:
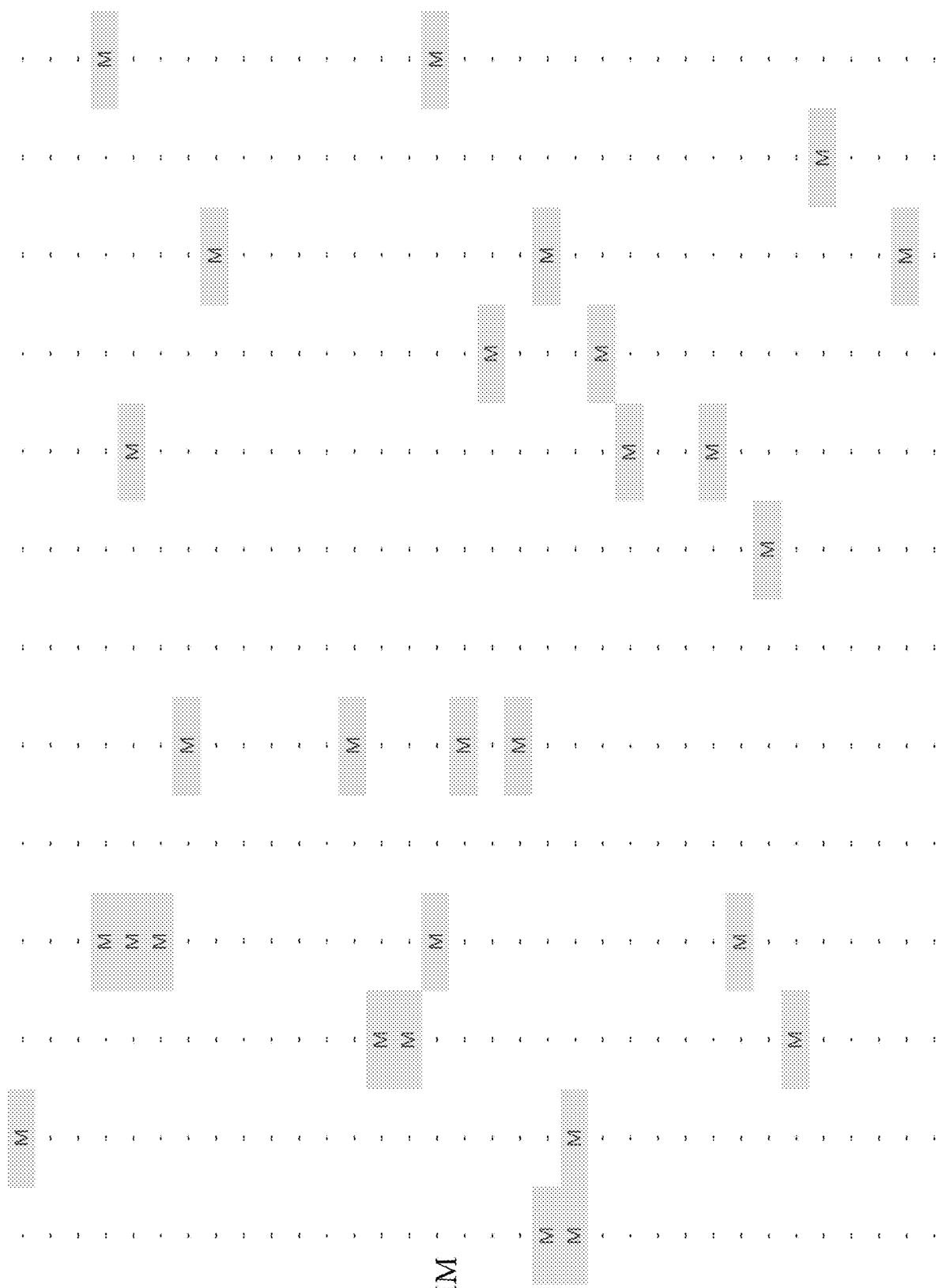
Figure 7N:
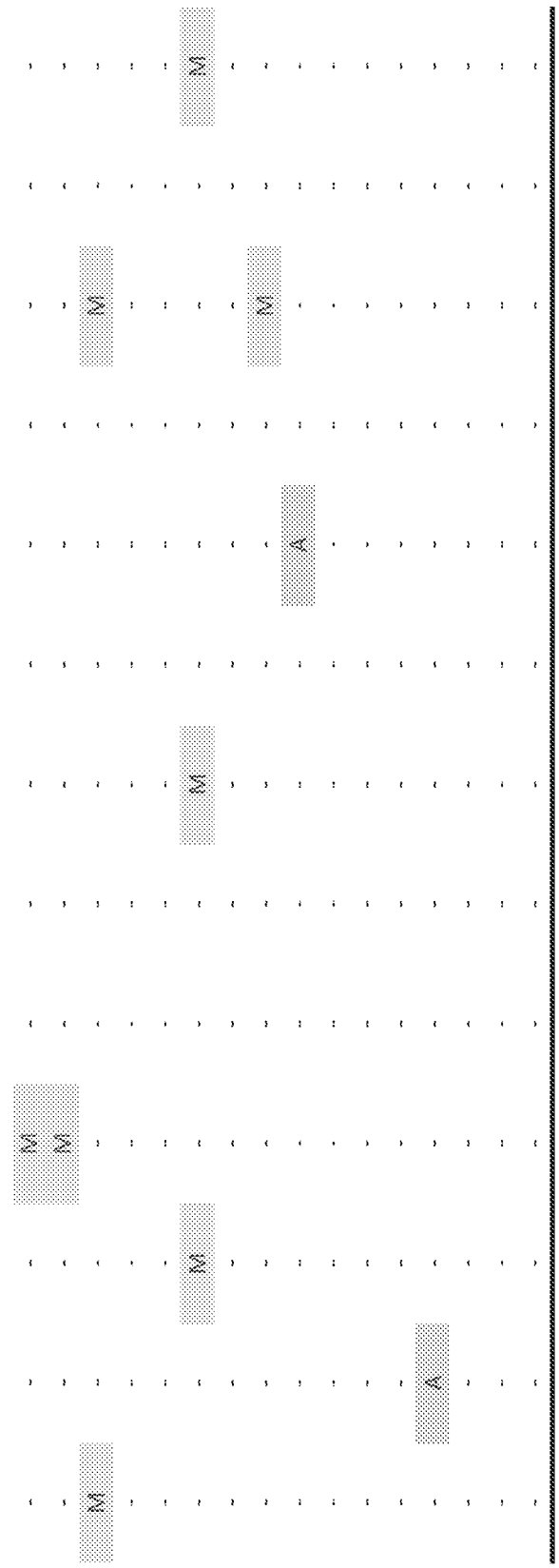
Figure 7O:
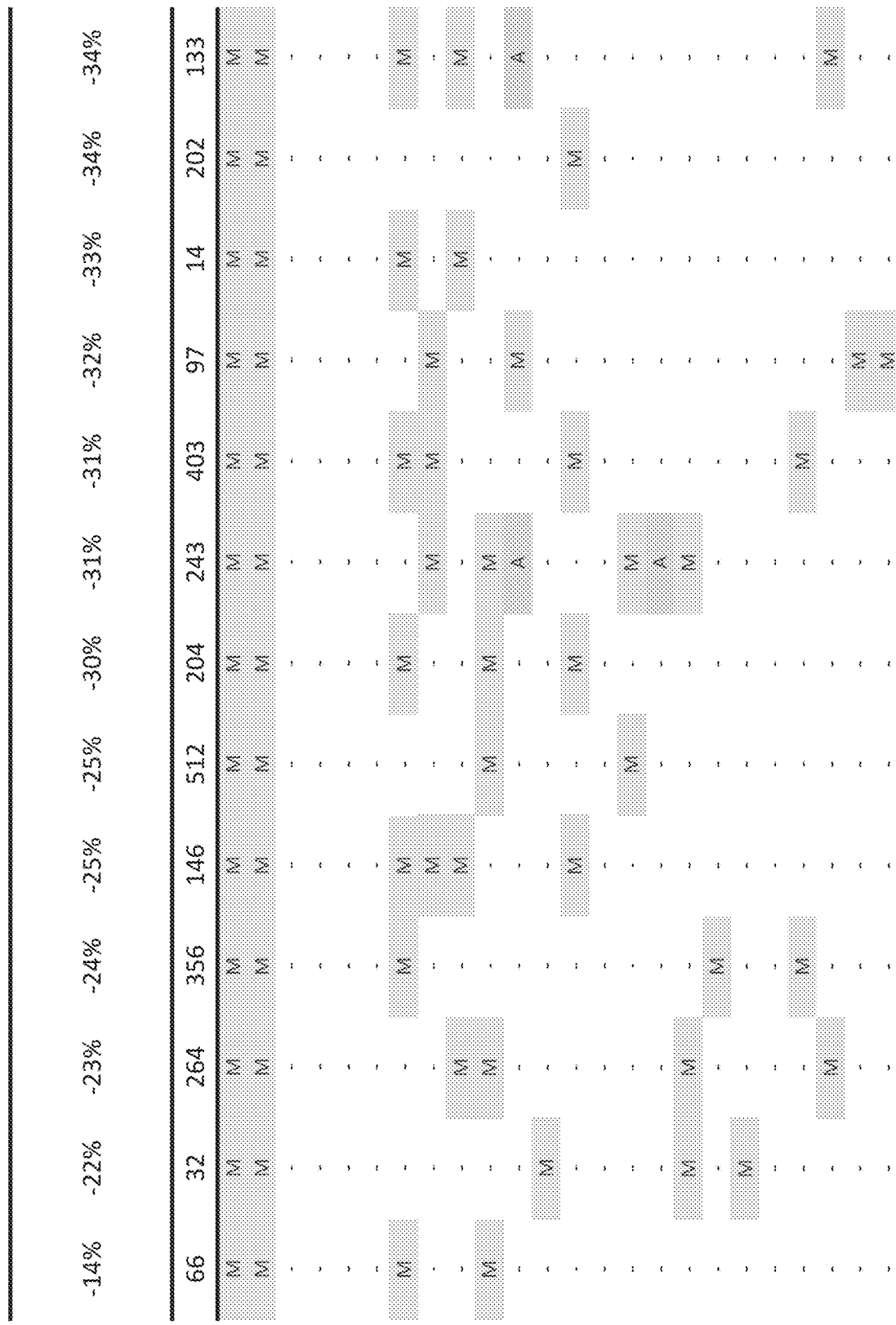
Figure 7P:
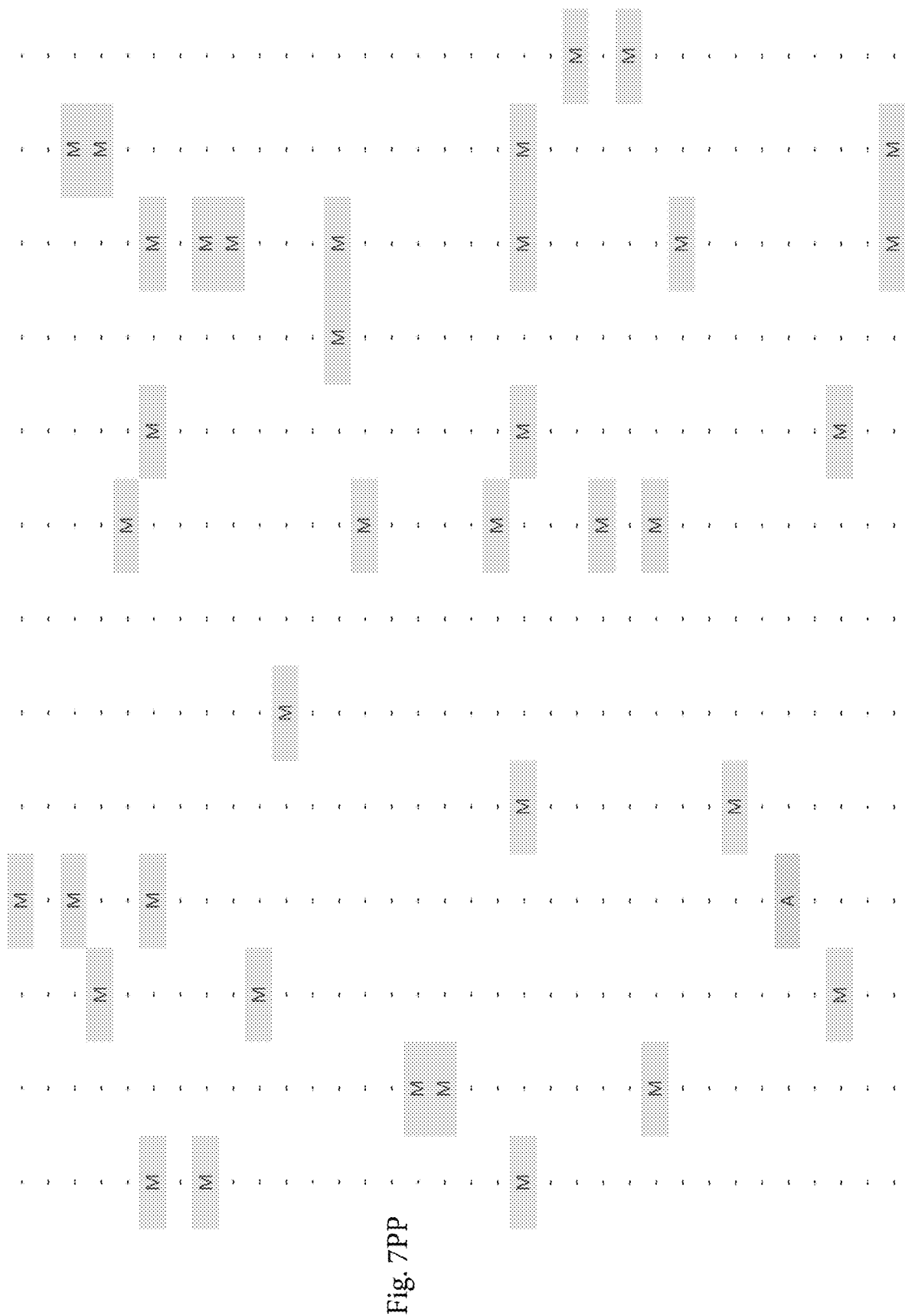
Figure 7Q:
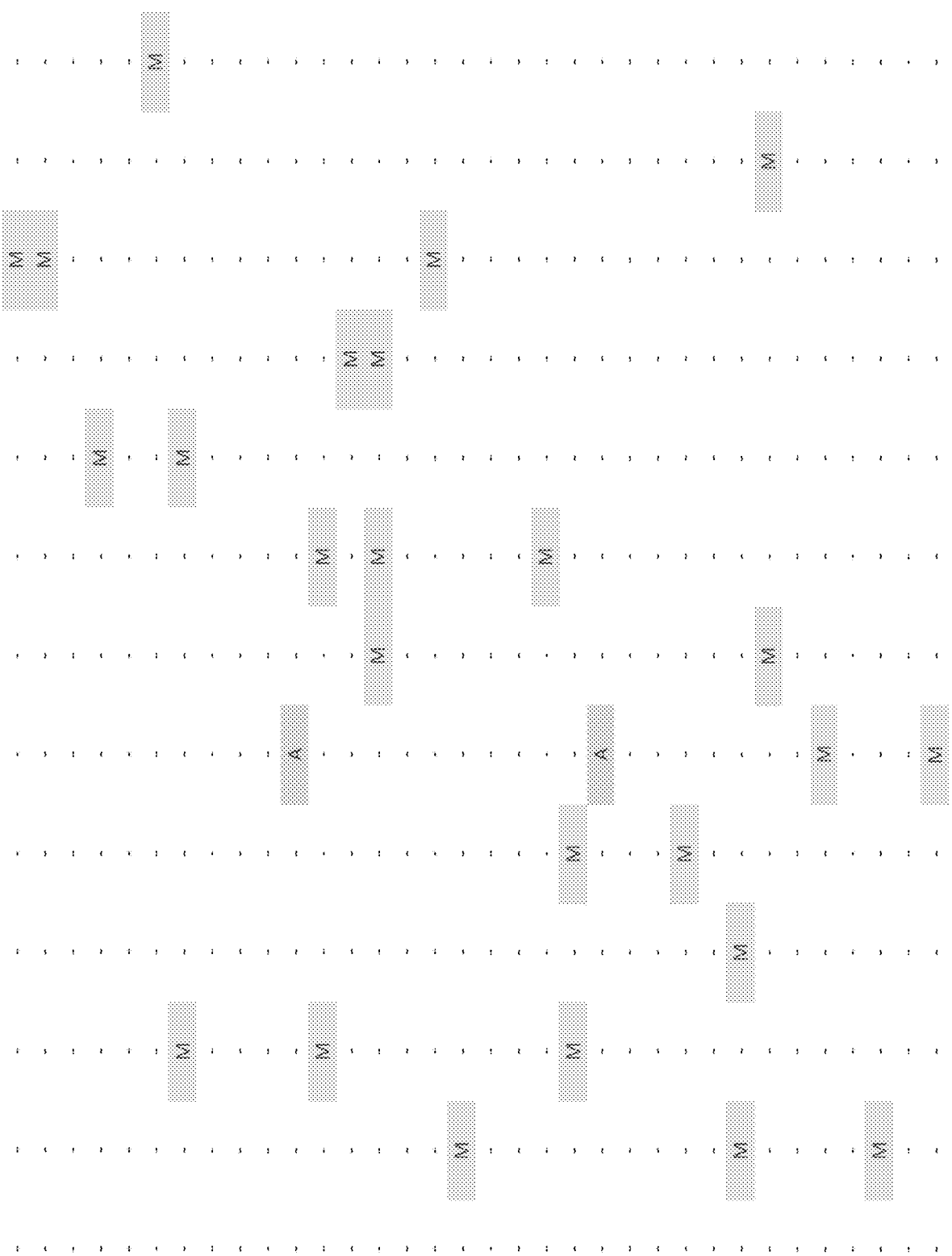
Figure 7R:
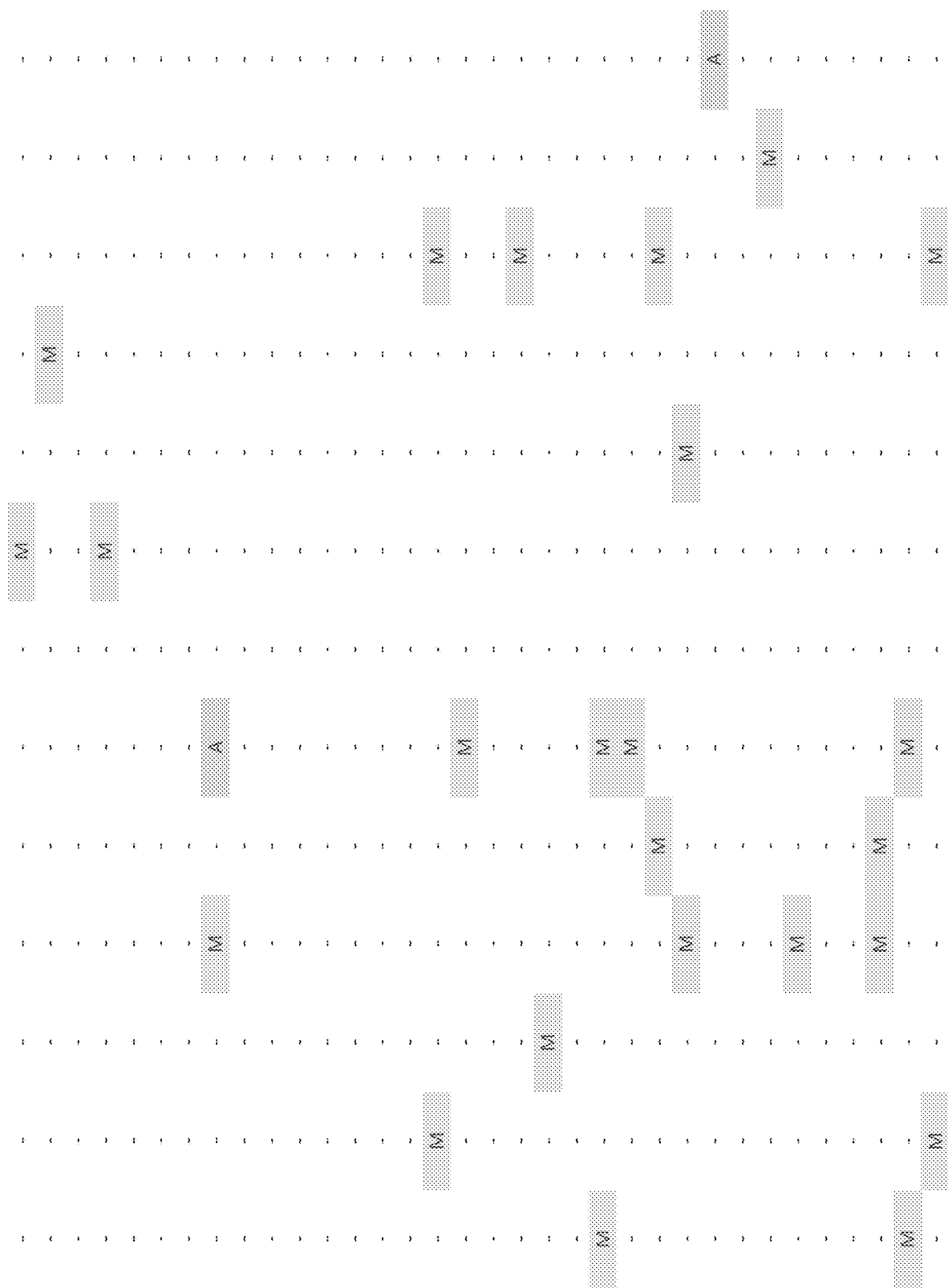
Figure 7S:
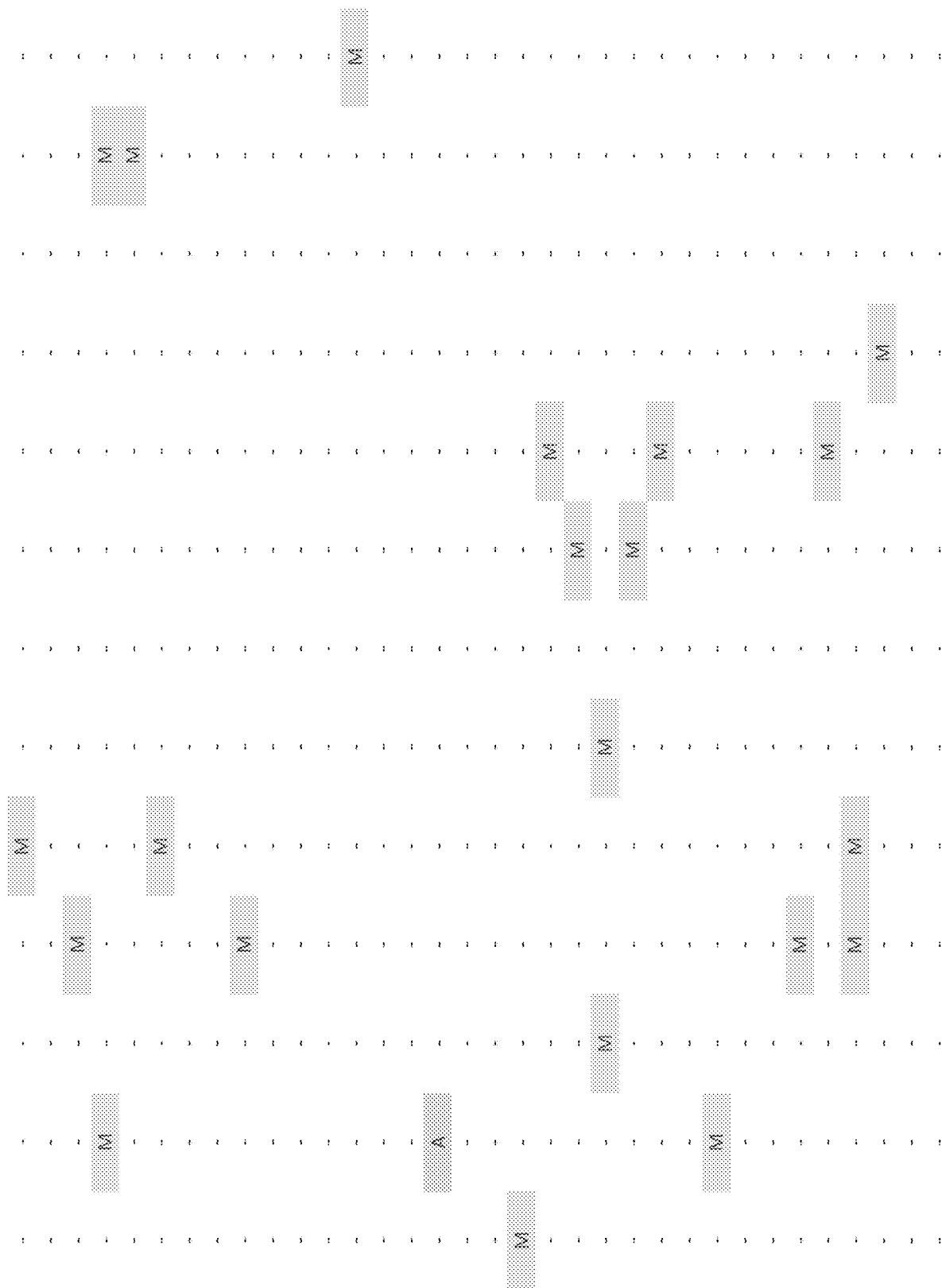
Figure 7T:
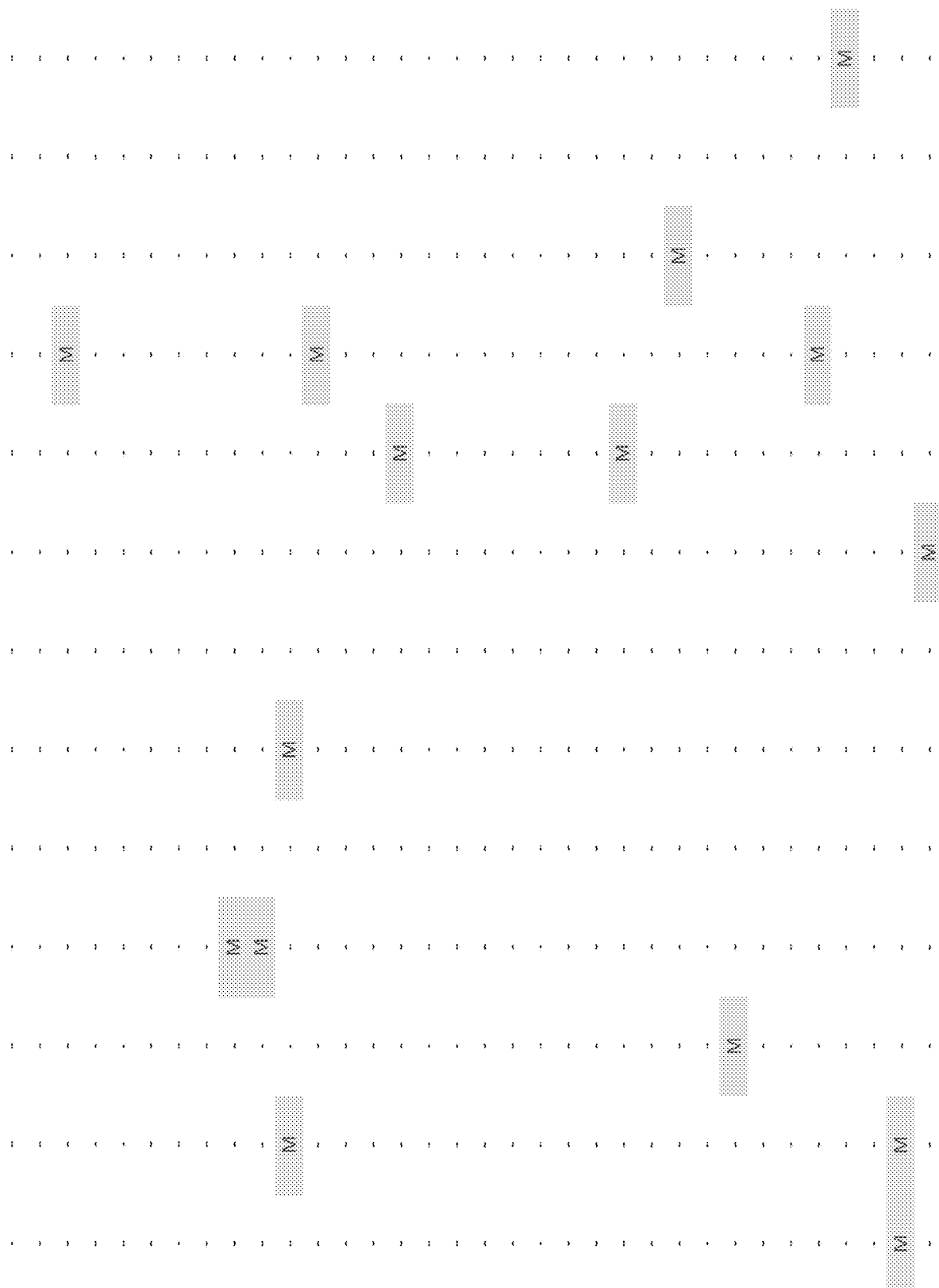
Figure 7U:
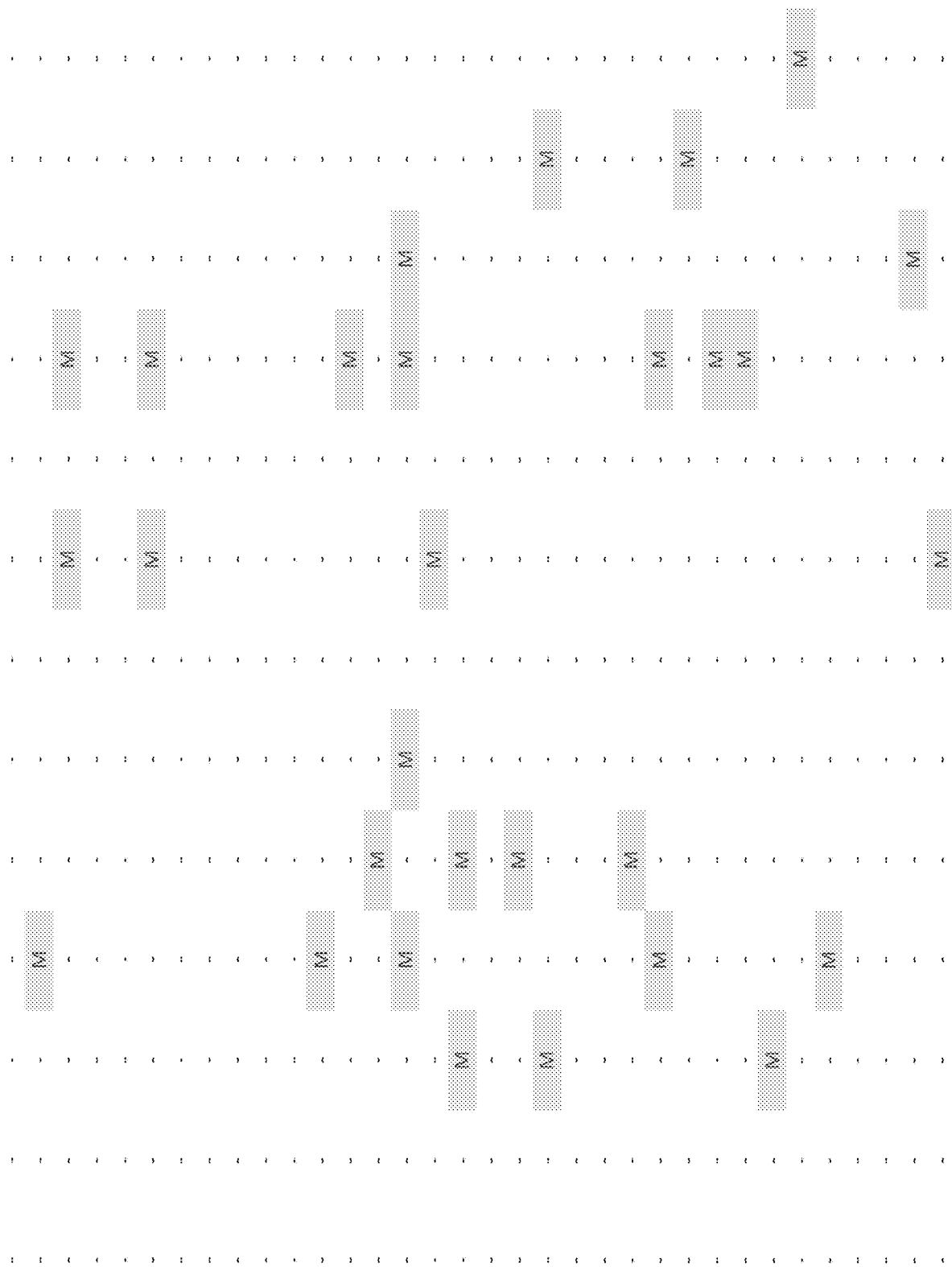
Figure 7V:
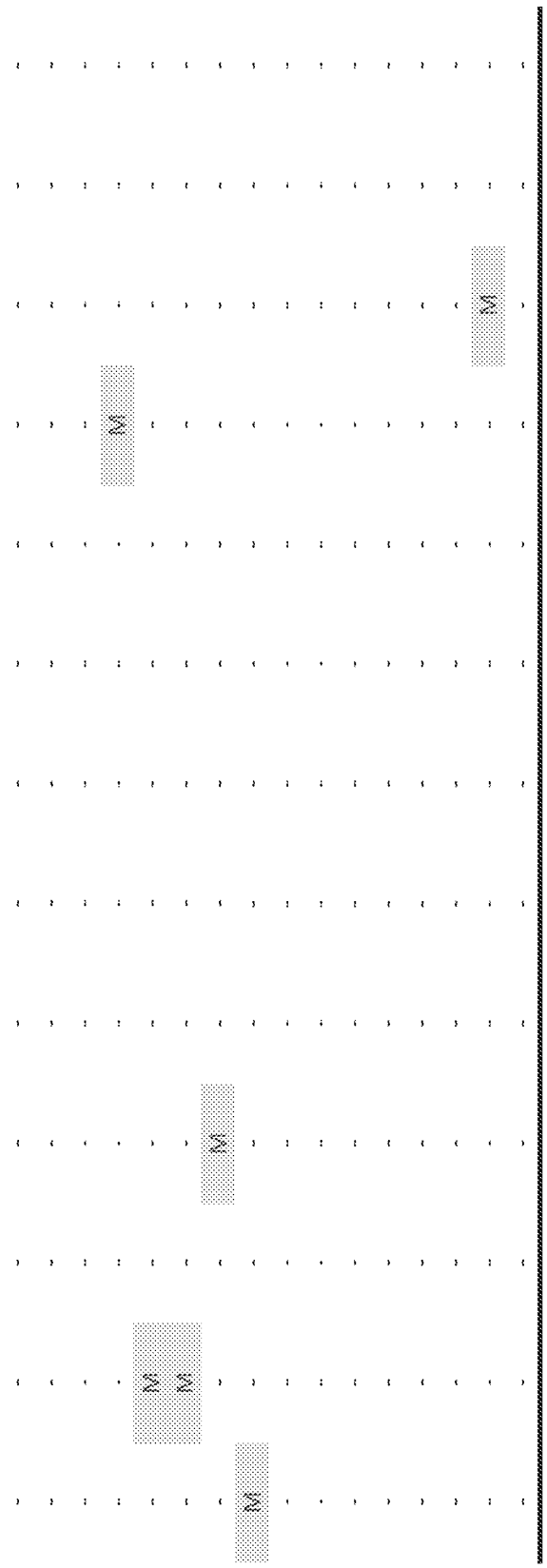
Figure 7W:
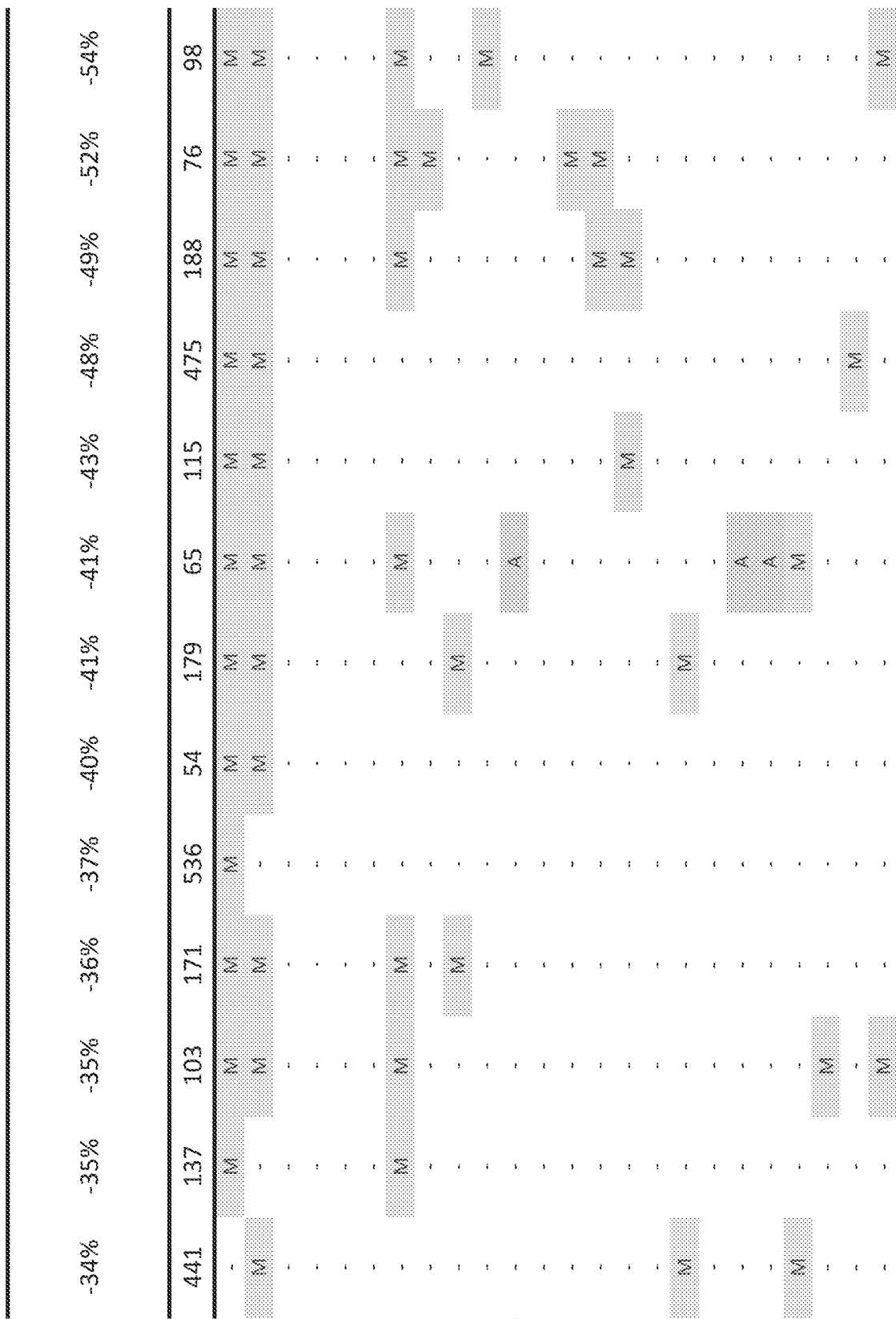
Figure 7X:
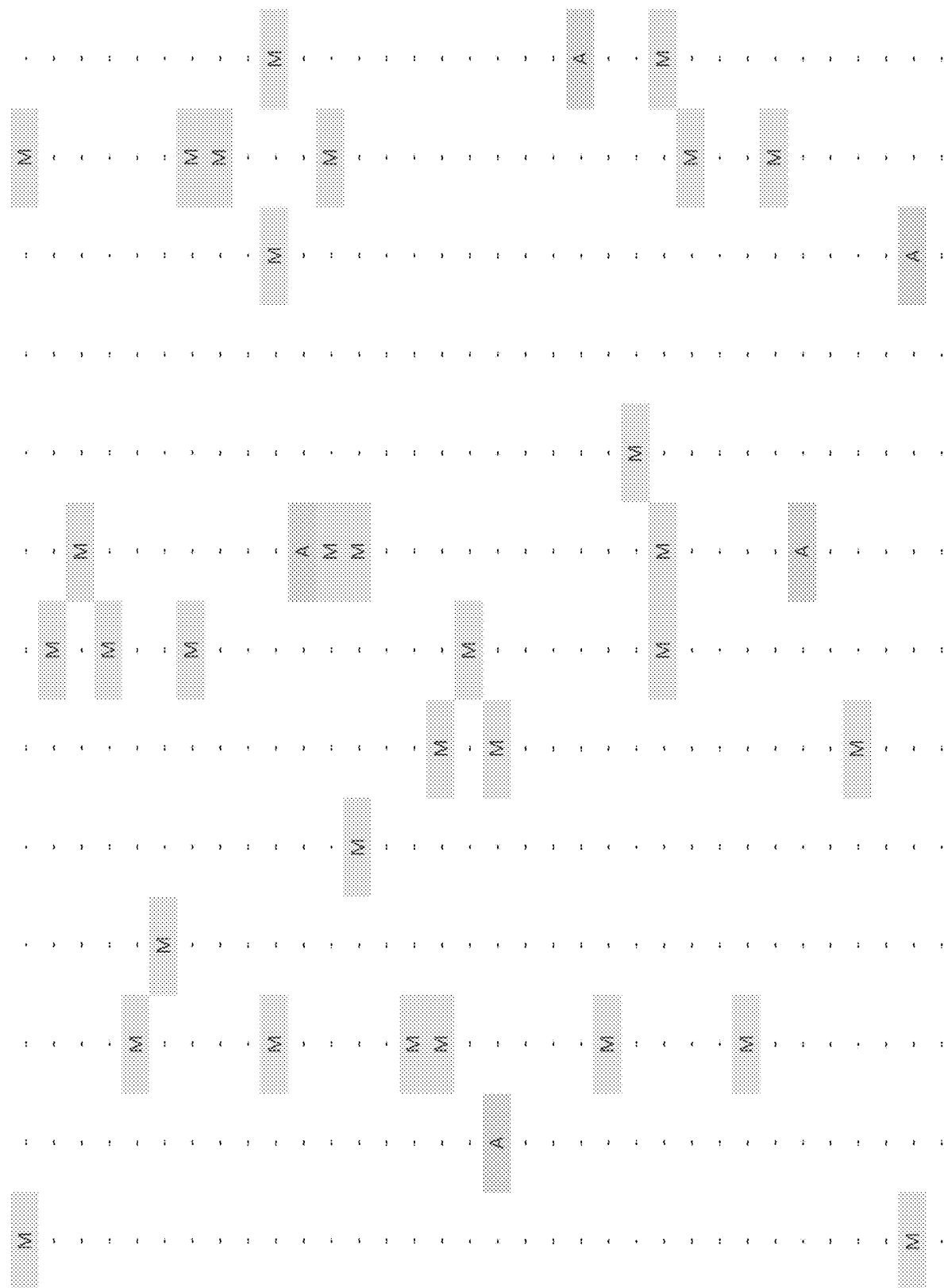
Figure 7Y:
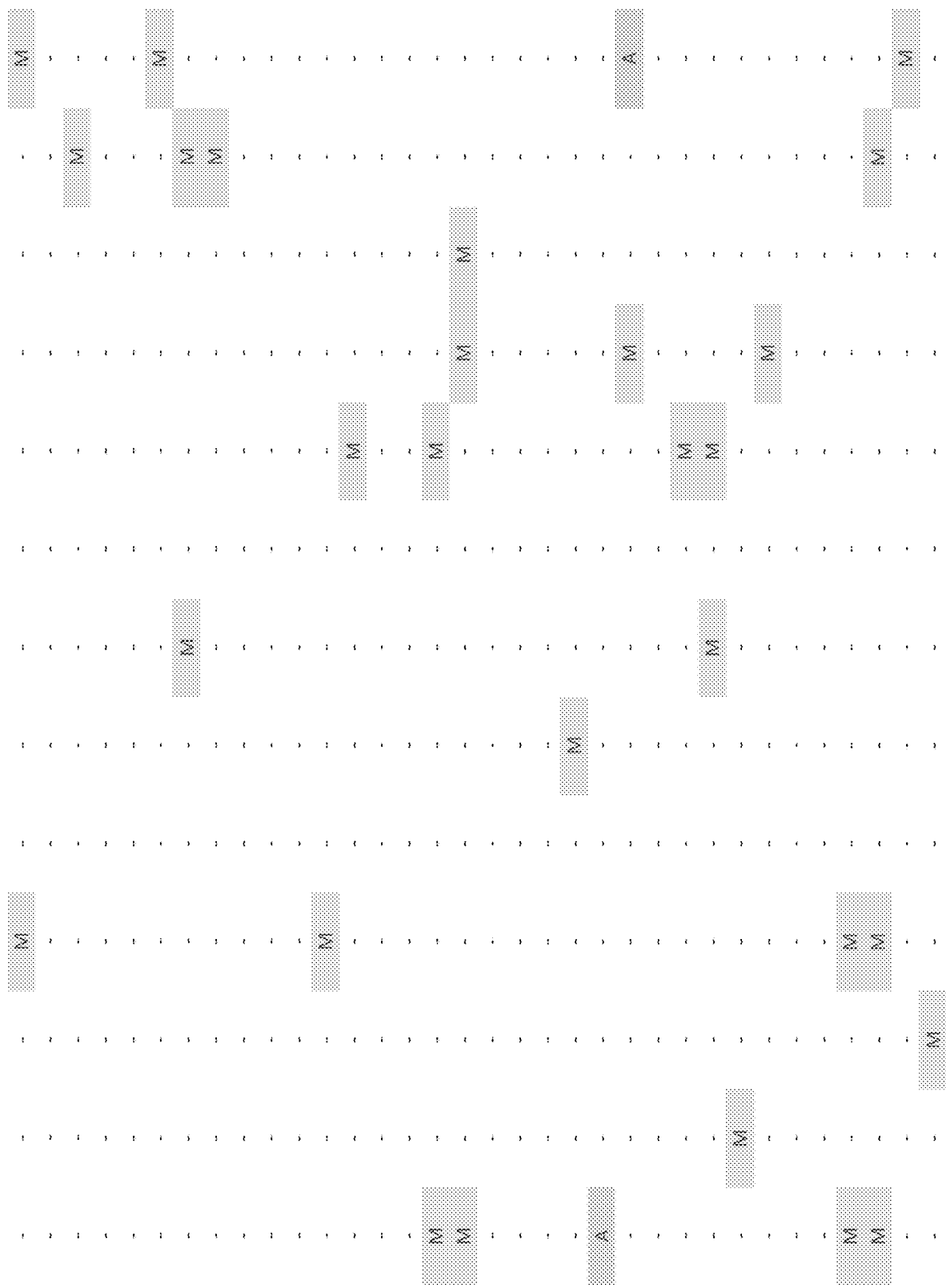
Figure 7Z:
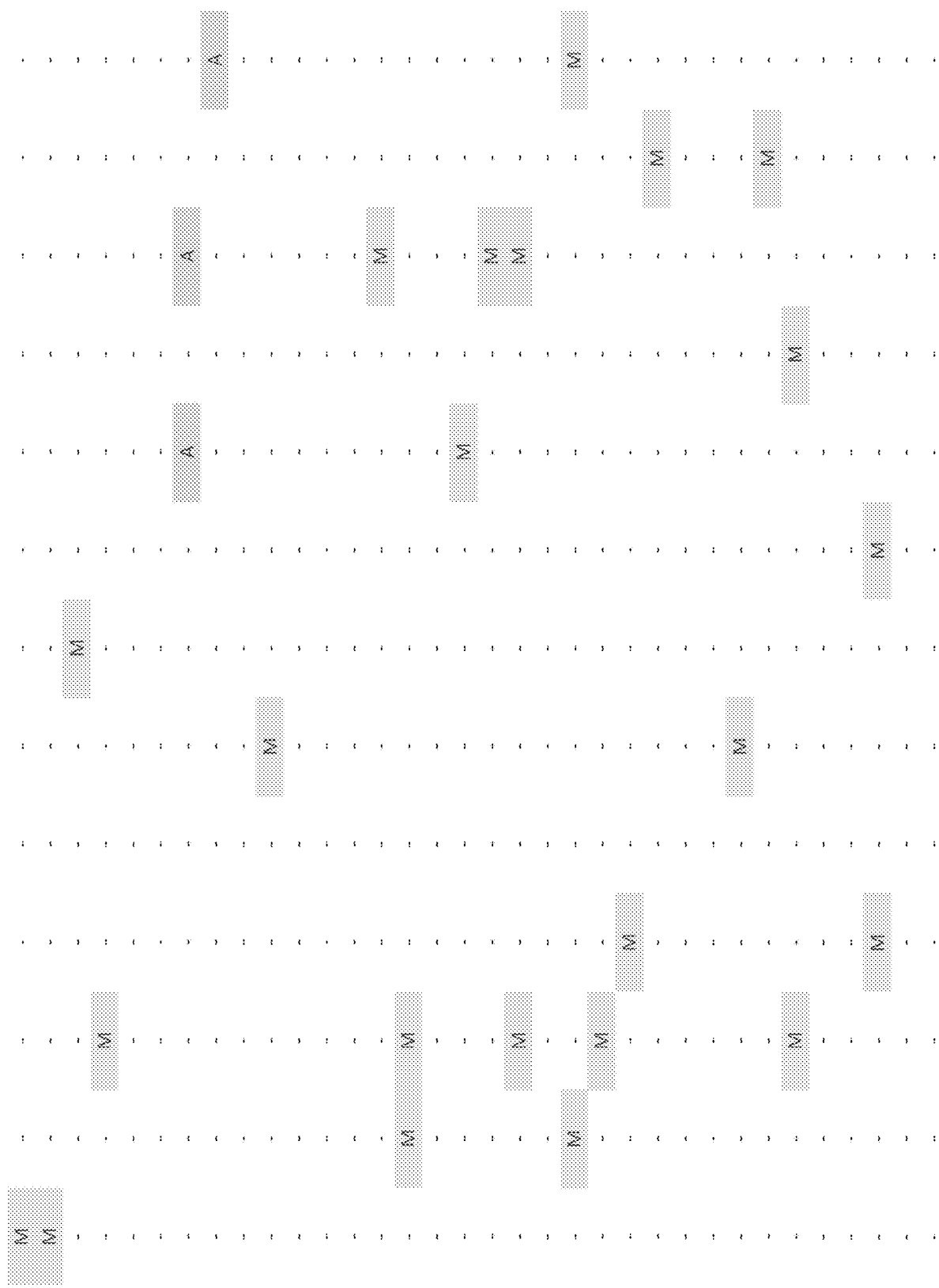
Figure 7:
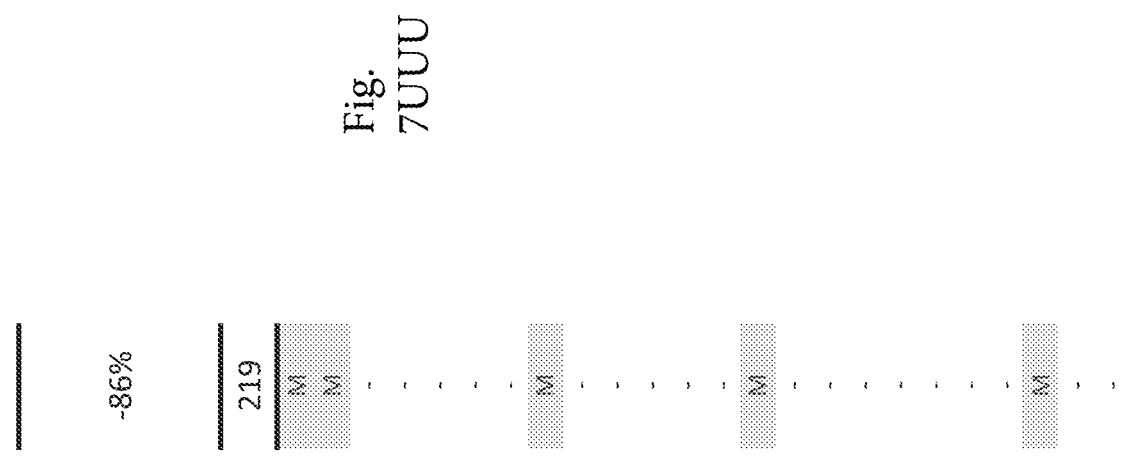
Figure 7:
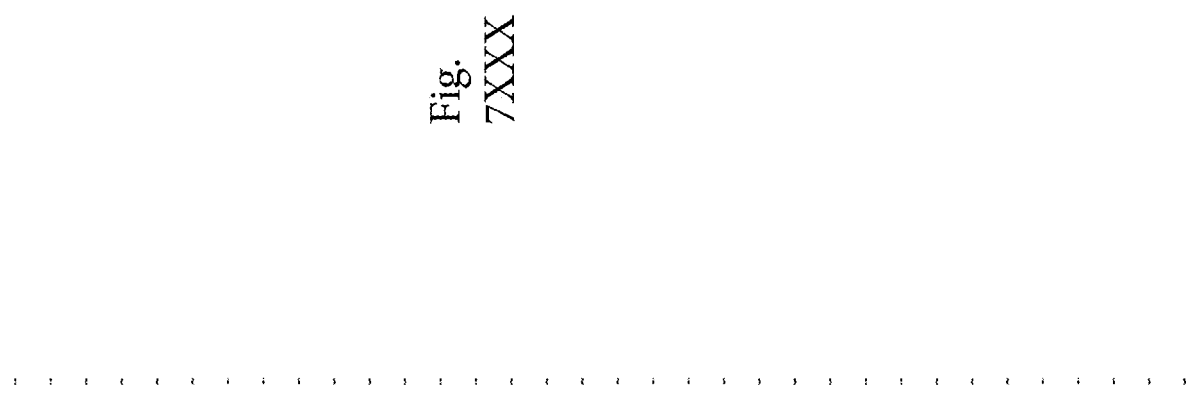

FIG. 6A-6D. (Supplementary Table 5) Frequently Altered Genes in KRAS WT metastatic CRC FIG. 7A-7CCCC. (Supplementary Table 6) Integration of Somatic Alterations with Response to anti-EGFR Blockade

DETAILED DESCRIPTION OF THE INVENTION

The inventors have developed methods for treating tumors that have developed resistance to agents which blockade or inhibit epidermal growth factor receptor (EGFR). The inventors have also found the certain combinations of anti-tumor agents act synergistically to inhibit tumor progression. The inventors have also found that certain genetic changes indicate sensitivity to EGFR blockade or inhibition.

Agents which can be used to inhibit or block EGFR include any that are known in the art. The agents may be, for example, small molecule inhibitors, particularly kinase inhibitors, or antibodies. These include, without limitation, Afatinib, Bevacizumab, BMS-690514, Brivanib, Cabozantinib, Cetuximab, Cixutumumab, Dacomitinib. Dalotuzumab, Figitumumab, Ganitumab. Neratinib, Onartuzumab, Rilotumumab, Sorafenib, Sunitinib, Tivantinib, and Vandetanib.

Tumors which can be treated according to the invention include any which are treated with EGFR inhibitors or blocking agents. Such tumors include without limitation non-small-cell lung cancer, pancreatic cancer, breast cancer, colon cancer, rectal cancer, and glioma. Other tumors which may be treated include prostate cancer, ovarian cancer, cervical cancer, uterine cancer, melanoma, astrocytoma.

Testing for amplification or activating mutations in tyrosine kinase receptor adaptor gene IRS2 can be accomplished by any means known in the art. Targeted assays for this particular gene or assays of the entire genome may be used. Targeted assays may use amplification and sequencing, amplification and specific probes, digital amplification, primer specific extension, etc. Assays of the whole genome or whole exome may be used. Any format and technique may be selected as is convenient.

Testing for BRAF mutations or MET amplification or FGFR1 amplification or FGFR mutations, PDGFR mutations, MAP2K1 mutations, and ERBB2 mutations can be accomplished by any techniques known in the art. Gene sequencing, mutation specific probes, mutation-specific amplification, digital amplification or digital karyotyping, are examples of techniques which may be used to identify mutations or amplifications.

Inhibitors of MET, ERBB2, FGFR, and PDGFR which can be administered or prescribed are any which are known in the art. They may be, for example, antibodies or small molecule kinase inhibitors. These include without limitation: nilotinib, AM7, SU11274, BMS-777607 and PF-02341066, MK-2461, JNJ-38877605, PF-04217903, GSK 1363089 (XL880, foretinib), trastuzumab, AZD4547, Ponatinib, Dovitinib, BGJ398, E-3810, JNJ-42756493, ARQ 087, Tyrphostin AG 1295, Pan-HER, and AG-370.

Mutations which may be identified in EGFR related to resistance to certain anti-EGFR antibodies are V8431, G465E, and G465R. These mutations may be associated with resistance to cetuximab or panitumumab.

MEK inhibitors which may be used therapeutically without limitation include ACZD6244, Trametinib (GSK1120212). Selumetinib, Binimetinib or MEK162, PD-325901, Cobimetinib or XL518, CI-1040, and PD035901. ERK inhibitors which may be used include SCH772984.

The studies described below represent the most comprehensive analysis of genetic determinants of response to a targeted therapeutic agent in cancer. Through this effort we detected essentially all previously known mechanisms of primary resistance to cetuximab in CRC. Our data identified additional candidate mechanisms of primary and secondary resistance through alterations affecting EGFR, its downstream signaling pathway, and other cell surface receptors (FIG. 3). These alterations, together with KRAS, account for over three quarters of cetuximab resistant tumors and suggest that the vast majority of underlying causes of primary resistance have now been determined and can be identified prior to the initiation of anti-EGFR treatment.

The fact that a majority of tumors contain genetic changes resulting in resistance to EGFR therapy is a clinical challenge for late stage CRC patients. Fortunately, some of the mechanisms of resistance provide avenues for intervention, including amplification of FGFR1, mutation of PDGFR1 or ERBB2, and the previously identified amplification of ERBB2 and MET receptors. These receptors are targets of therapies that are already established or in development and could be useful in tumors with mutations in these genes. The observed alterations in MAP2K1 also suggest that targeting pathways downstream of EGFR, including the MAPK pathway, may prove beneficial (57). As we have shown through our tumorgraft studies, a combination of therapies targeting both the protein products encoded by resistance genes as well as EGFR or other signaling partners are likely to be crucial for inhibiting the multiple genetic components within a tumor. The high fraction of tumors with actionable alterations suggests that additional combinatorial therapies may be useful for CRC patients.

An unexpected finding of this study was the identification of an additional mechanism of sensitivity to anti-EGFR therapy. Although many late stage patients with KRAS wild-type tumors receive cetuximab or panitumumab, less than 15% have durable responses (24, 58). We have shown that in addition to the absence of other potential resistance alterations, the presence of genetic changes in IRS2 was significantly associated with response to cetuximab therapy. IRS2 signaling is activated through ligand-mediated cell surface receptors, including EGFR (59, 60). Our data suggest that IRS2 alterations may identify tumors that are most dependent on receptor signaling and therefore most sensitive to its therapeutic inhibition. Consistent with this prediction are reports that IRS2 amplification is a significant indicator of response to the IGF1R inhibitor figitumumab in colorectal and lung cancer cell lines (61). Given the interaction of IRS2 with multiple cell surface receptors, we predict that combinatorial inhibition of the receptors in tumors with IRS2 alterations may provide even more long-lasting responses in such patients.

This study highlights information that may be obtained through the integration of large-scale genomic and targeted therapeutic analyses in CRC. Although careful measures were taken to increase the sensitivity of detecting genetic changes in these tumors, some alterations may not have been detected due to low tumor purity, poor sequence mapping, or low coverage using next-generation sequencing approaches. Likewise, although the use of tumorgrafts has shown promise as "avatars" for individual patient therapies (62), they may not fully represent the range of therapeutic responses observed clinically. Despite these limitations, these data provide an unprecedented view into mechanisms of response to EGFR blockade. Through integrated genomic analyses, we have identified a compendium of markers of primary and secondary resistance as well as sensitivity in this disease. This information provides a framework for analysis of responses to targeted therapies in CRC and suggests interventional clinical therapies using combinatorial therapies based on potentially actionable alterations.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Overall Approach

As KRAS alterations are a well-established mechanism of resistance to EGFR inhibitors (22-24), we selected 137 colorectal tumors that were wild-type at codons 12, 13 and 61 of KRAS as determined by Sanger sequencing (36). The colorectal cancers analyzed were all liver metastases in patients who underwent potentially curative resections. To elucidate genetic alterations in the coding regions of these cancers, we used next-generation sequencing platforms to examine the entire exomes of matched tumor and normal specimens (36) (FIG. 1. Given the low neoplastic cellularity of colorectal cancers (37), we enriched for neoplastic cells using patient-derived tumorgrafts and performed deep sequencing (high coverage) of the enriched tumor samples and matched normal DNA (36). This approach allowed us to identify sequence changes, including single base and small insertion or deletion mutations, as well as copy number alterations in >20,000 genes in the whole-exome analyses. We obtained a total of 4.23 Tb of sequence data, resulting in an average coverage within the target regions of nearly 150-fold for each patient.

Sequence analyses of 135 of 137 tumors identified a median of 117 somatic mutations in each cancer, similar to previous whole exome studies in CRC (18-20). Two tumors displayed an elevated number of somatic sequence alterations (2979 and 2480 changes per exome), consistent with a mutator phenotype (20). Common CRC driver genes, including APC, TP53, PIK3CA, PTEN, SWAD4, FBXW7, TCF7L2 and SOX9 were identified at expected frequencies in the tumors analyzed (FIG. 6A-6D: Table S5). A total of 8 tumors were identified as having KRAS alterations at codons 12 or 13 that were not initially detected by Sanger sequencing and were excluded from further analysis.

Example 2

Primary Resistance to Anti-EGFR Therapy

Figure 1:
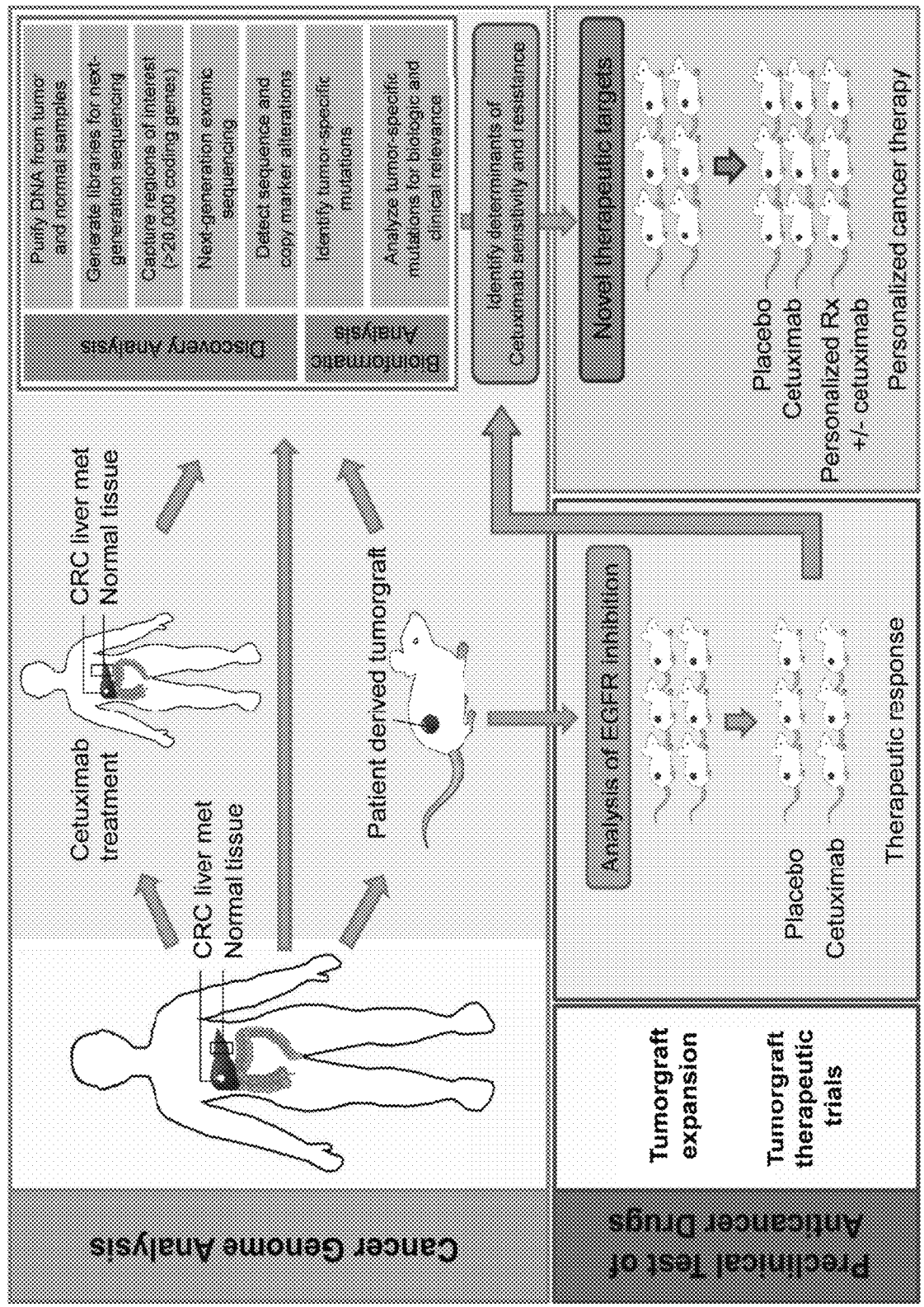
FIG. 1. Schematic diagram of integrated genomic and therapeutic analyses. Resected colorectal cancer hepatic metastases were directly implanted in NOD/SCID mice. One hundred thirty seven early passage tumorgrafts and matched normal samples were analyzed using whole exome sequence and copy number analyses. In parallel, tumorgrafts were established and evaluated for response to cetuximab in preclinical therapeutic trials. For a subset of cases, pre-implanted material and cetuximab treated hepatic metastases were also analyzed by targeted sequencing. Integration of genomic and therapeutic information was used to identify candidate resistance and response genes, as well as to design preclinical trials using therapeutic compounds to overcome resistance to anti-EGFR blockade.
Figure 2:
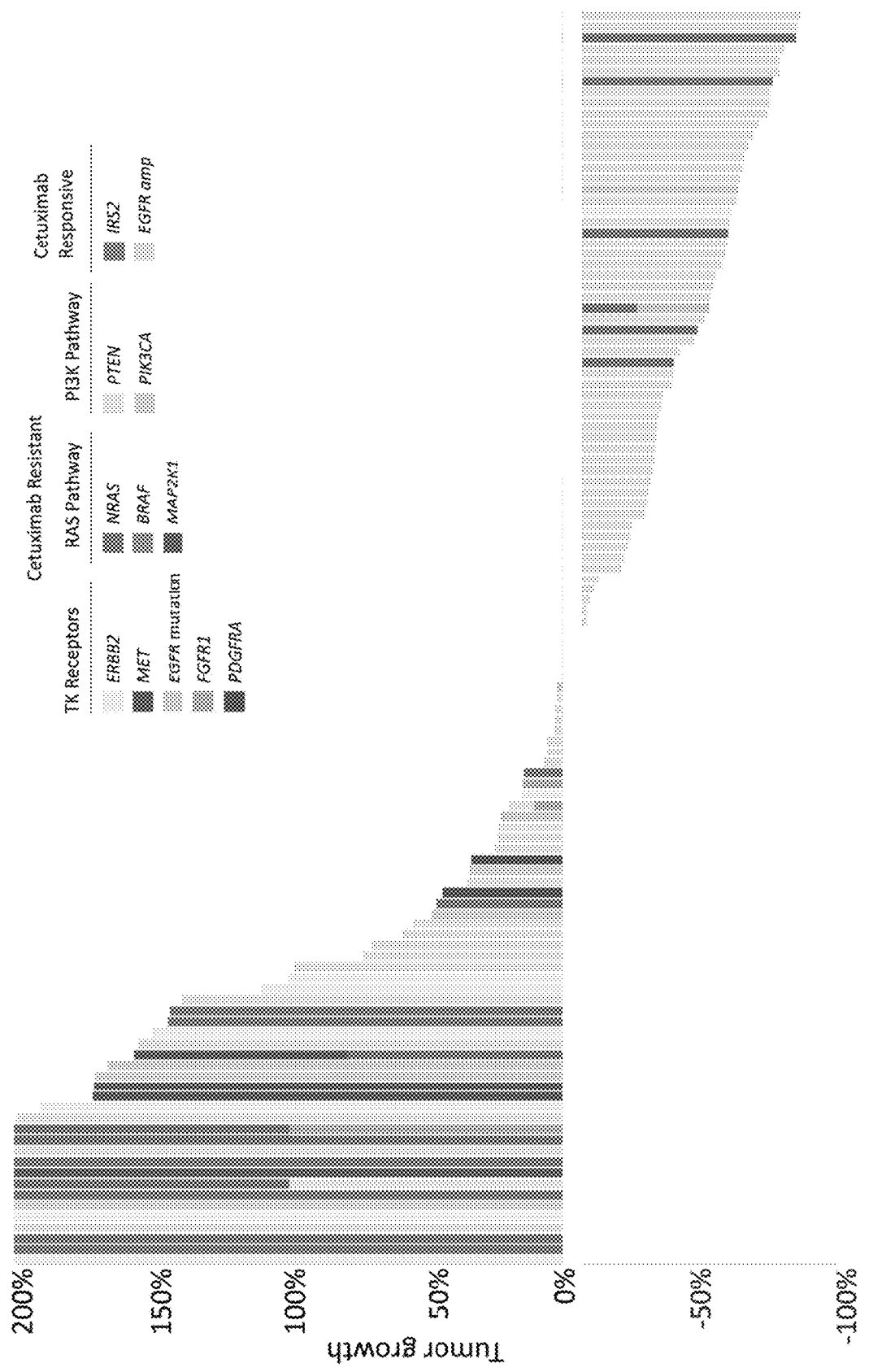
FIG. 2. Effect of cetuximab treatment on growth of colorectal tumors with different somatic alterations. The change in tumor growth in preclinical trials is determined as the fold growth or shrinkage from baseline in 116 KRAS wild-type tumorgrafts. Candidate alterations related to therapeutic resistance or sensitivity are shown in the indicated colors (complete list of alterations are in Tables S3, S4 and S6). For the following genes a subset of alterations are indicated: MET amplification; FGFR1 amplification; PDGFRA kinase domain mutations; BRAF V600 hotspot mutations; PTEN homozygous deletion or truncating mutations.

To evaluate whether the alterations that we identified were associated with resistance to EGFR inhibitors, we determined tumorgraft response to cetuximab therapy for 116 of the CRCs after tumor implantation (FIGS. 1, 2). The volume of each tumorgraft was evaluated at three and six weeks in 12 or 24 mice (depending on individual models) that were randomized to treatment and control arms at a 1:1 ratio. Tumors were categorized as showing disease progression (36 cases, 31%), regression (39 cases, 34%), or stabilization (41 cases, 35%) (36). We compared the integrated profiles of genomic alterations and therapeutic responses of the tumors analyzed and focused on genes that were predominantly altered in cases showing tumor growth in the presence of anti-EGFR therapy (FIG. 2, FIG. 7A-7CCCC; Table S6). Among tumorgrafts with disease progression or stabilization, we detected coding alterations in all genes known to be involved in EGFR therapeutic resistance: NRAS sequence mutations in codons 12 or 61 (7 cases), BRAF V600E mutation (3 cases), MET amplification (3 cases), and ERBB2 amplification (4 of 5 cases). Additionally, 3 of 4 tumors with alterations in exon 20 of PIK3CA and 4 of 5 tumors with protein truncating or homozygous deletions of PTEN were resistant to anti-EGFR blockade, consistent with previous studies (25, 38).

In addition to genes known to confer resistance to EGFR blockade, we also evaluated potential mechanisms of resistance that have not been previously described in colorectal cancer. We focused on other cell surface protein kinase receptors or members of the EGFR signaling pathway and identified candidate genes that were preferentially altered in therapy-resistant tumors (FIGS. 2, 3; Tables S3, S4) We observed point mutations affecting the ERBB2 kinase domain, including in two patient tumors with exactly the same change at 777V>L and another tumor harboring an 866L>M mutation, as well as a sequence change in the ectodomain at 310S>Y, all of which correlated with cetuximab resistance. Although ERBB2 amplification has been liked to colorectal cancer (30, 31, 37), sequence alterations are more frequently observed in other tumor types including breast and lung cancers (39, 40) and have not been linked to therapeutic resistance of anti-EGFR blockade. Previous reports have shown that alterations at residue 777 lead to constitutive activation of ERBB2 both in vitro and in vivo (40). These data suggest that somatic mutations in ERBB2 may provide an alternative mechanism for ERBB2 pathway activation that is complementary to ERBB2 amplification in colorectal cancer. Similar to ERBB2, we found sequence alteration in the kinase domain of EGFR (843V>I) in one case that showed tumor growth in the presence of cetuximab. Although EGFR kinase alterations are rare in colorectal cancer (41, 42), the observed case suggests that in principle such changes may provide a mechanism of resistance to anti-EGFR therapy.

We identified alterations in additional cell surface protein kinase receptors: amplification of the fibroblast growth factor receptor FGFR1 and sequence alterations in the platelet-derived growth factor receptor PDGFRA. Each of these was altered in four of the 129 CRC samples analyzed (8 samples total, 6%). Tumor growth was observed in all cetuximab treated cases with FGFR1 and PDGFRA alterations. FGFR1 is a known driver gene in a variety of human cancers (43) and has been reported to be amplified in different tumor types, including lung cancer, breast and colorectal cancers (44-46). PDGFRA is a tyrosine kinase receptor that is known to be mutated in gastro-intestinal stromal tumors (47). The detected sequence alterations in PDGFRA, including a mutation that affected the same residue in two different patients (981R>H), were all located in or near the protein catalytic domain of the protein. Similar to ERBB2 and MET, the receptors encoded by these genes transmit signals through the RAS/MEK cascade and when mutated can lead to constitutive activation of oncogenic pathways (43, 48).

We further examined candidate alterations within the RAS pathway and observed a nucleotide sequence change resulting in an amino acid swap of lysine to arginine at residue 57 in the mitogen activated protein kinase kinase gene MAP2K1 in a cetuximab-resistant case. Alterations of MAP2K1 at the same or nearby residues have been described in CRC, melanoma and lung cancer (49, 50) and are adjacent to the catalytic domain. The 57K>N alteration has been shown to confer IL-3-independent cell growth in BaF3 cells, suggesting that this mutation may be functionally active (49). Overall, the enrichment of mutations in known and previously unknown pathways in the resistant tumorgrafts was statistically significant (p<0.001. Welch Two Sample t-test) and suggests that alterations in any of these members may be sufficient to render cells insensitive to EGFR inhibition (36).

Example 3

Acquired Resistance to Anti-EGFR Therapy

Although some tumors initially respond to cetuximab, virtually all CRC patients treated with anti-EGFR therapy eventually develop disease recurrence (38). In our analyses, 22 tumors were resected from patients that had received cetuximab within six months prior to surgical resection. We examined whether novel alterations in these cases may have arisen as acquired (secondary) resistance to this therapy. Two of these 22 tumors (9%) had G to A sequence substitution in the EGFR coding region at nucleotide positions 1393 and 1394, resulting in a substitution of glycine to glutamic acid (465G>E) or arginine (465G>R) in domain III of the extracellular portion of the receptor. Sequencing of normal liver from these patients revealed only wild-type sequences at these residues and confirmed that the 465G>E and 465G>R mutations were somatic. Structural analyses suggested that these mutations were likely to affect cetuximab binding as they were located at the interface of EGFR-cetuximab interaction (FIG. 4A). Interestingly, through an intervening parallel beta-sheet, G465 is structurally adjacent to residue S492 within the ectodomain region of EGFR that has been shown, when altered, to interfere with cetuximab binding (32) (FIG. 4A).

To determine whether the putative resistance mutations affecting EGFR amino acid residue 465 were present in the cetuximab naïve tumor or were acquired following treatment, we examined pre- and post-therapy specimens for subjects CRC104 and CRC177 whose tumor harbored the 465G>E and 465G>R EGFR ectodomain mutations, respectively (FIG. 4B). Targeted capture and deep sequencing (723× coverage) of the post-cetuximab hepatic metastatic specimen resected from patient CRC104 confirmed the 465G>E mutation while the original colectomy specimen obtained before treatment did not have a detectable alteration (530× coverage) (FIG. 4C). Interestingly, patient CRC104 experienced an early relapse in December 2009 while on treatment with cetuximab, suggesting resistance to anti-EGFR therapy in the clinical setting. Similarly, longitudinal analyses of tumor specimens from subject CRC177 revealed wild-type EGFR in the pre-treatment biopsy of a liver metastasis (December 2009), emergence of the 465G>R mutation in a liver deposit resected after cetuximab-containing neo-adjuvant therapy (June 2010), and persistence of this mutation in resected tissue from a second-stage hepatectomy after an additional line of neo-adjuvant cetuximab (September 2010) (FIG. 4B, 4C). Although these findings do not rule out the presence of these alterations in one or a small number of cells in the pre-treatment tumors, the genomic analyses suggest that the alterations were clonally detectable only after selection in the presence of cetuximab.

Example 4

Determinants of Sensitivity to EGFR Blockade

Among colorectal cancer patients that have KRAS wild-type tumors, only 12-17% have durable responses to anti-EGFR antibody monotherapy (24, 27). We wondered whether such responses may be due to alterations in genes that confer therapeutic sensitivity in addition to the absence of alterations that confer resistance. Amplification of the EGFR gene has been shown to increase anti-EGFR antibody sensitivity (51, 52) but other genetic markers of cetuximab response have not yet been identified. In our analyses, EGFR was found to be amplified in two tumors that showed either regression (CRC98, 26 fold amplified) or disease stabilization (CRC400, 3 fold amplified) (FIG. 2).

To discover indicators of anti-EGFR response, we examined the mutational landscape of tumors that showed tumorgraft regression following in vivo treatment with cetuximab. Given the importance of EGFR signaling, we analyzed other members of the pathway that were preferentially mutated in responsive tumors (36). The only other gene within the EGFR pathway that we identified to be associated with cetuximab response was IRS2, a cytoplasmic adaptor that mediates signaling between receptor tyrosine kinases and downstream targets (FIG. 2, FIG. 7A-7CCCC; Table S6) (p<0.05, Welch Two Sample t-test)(36). This gene had amplifications or sequence alterations in 7 CRC tumors (6%) that showed increased sensitivity or stable disease when treated with cetuximab. Similarly, expression analyses of the CRC tumors identified increased IRS2 levels as a significant predictor of cetuximab sensitivity (p<0.001. Student's t-test) (36). Two additional tumorgrafts with IRS2 alterations (CRC508 and CRC106) that were not responsive to cetuximab harbored a MET amplification or BRAF mutation, highlighting that IRS2 mutation is likely to be predictive for anti-EGFR response in cases without other mechanisms of resistance to EGFR therapy. We and others have previously identified alterations in IRS2 in CRCs and other tumor types (17, 20, 37, 53), but no reports to date have linked the effects of these alterations to therapeutic sensitivity.

Example 5

Therapeutic Targets for CRC Patients

Given the poor outcome of patients diagnosed with late stage colorectal cancer, and especially of those that are resistant to anti-EGFR inhibitors, we investigated whether mutant genes observed in individual cases may be clinically actionable using existing or investigational therapies. We examined altered genes that were associated with 1) FDA-approved therapies for oncologic indications, 2) therapies in published prospective or retrospective clinical studies, and 3) ongoing clinical trials for patients with colorectal cancer or other tumor types.

Figure 5A:
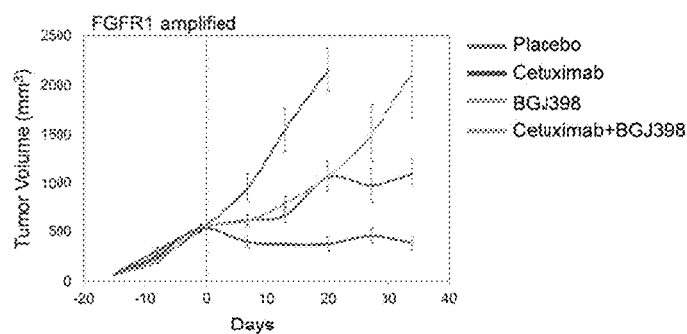

Through these analyses we identified somatic alterations with potentially actionable consequences in 100 of the 129 patients (77%). To test whether any of the identified actionable alterations may be successfully targeted in tumors with cetuximab resistance, we used the tumorgrafts to perform proof of principle trials for specific targeted therapies. We first chose as an example a cetuximab-resistant tumor with FGFR1 amplification (CRC477) and examined whether inhibition of both FGFR1 and EGFR would be more effective than inhibition of EGFR alone. The rationale for this approach is that such tumors have multiple active pathways providing growth signals from the cell surface that need to be simultaneously targeted. The original tumor specimen was serially passaged in vivo until production of final treatment arms. In vivo administration of the selective FGFR kinase inhibitor BGJ398, which is currently in clinical trials (54), began when the tumorgrafts reached an average volume of approximately 400 mm3. Mice were randomized into 4 independent treatment cohorts, each consisting of 6 mice:
  (i) vehicle (placebo); (ii) cetuximab alone; (iii) BGJ398 alone: (iv) cetuximab and BGJ398. We confirmed resistance to cetuximab alone and as may be expected using a single pathway inhibitor, the tumorgraft was also resistant to BGJ398 alone (FIG. 5A). However, a combination of BGJ398 together with cetuximab led to a substantial and durable suppression of tumor growth in all treated mice (p<0.01, two-way ANOVA). This model confirmed that combinatorial therapies may be effective in overcoming EGFR therapeutic resistance in tumors with alterations in other cell surface receptors.

Figure 5B:
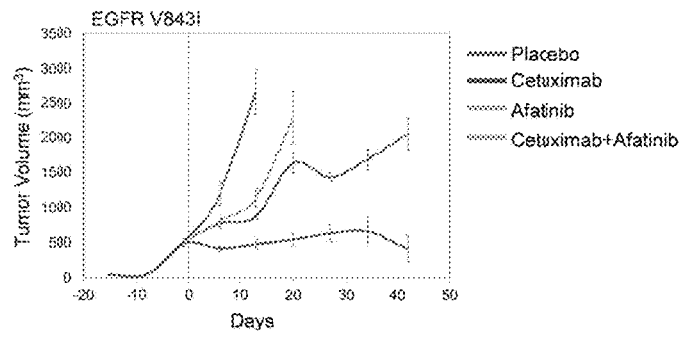
Figure 5C:
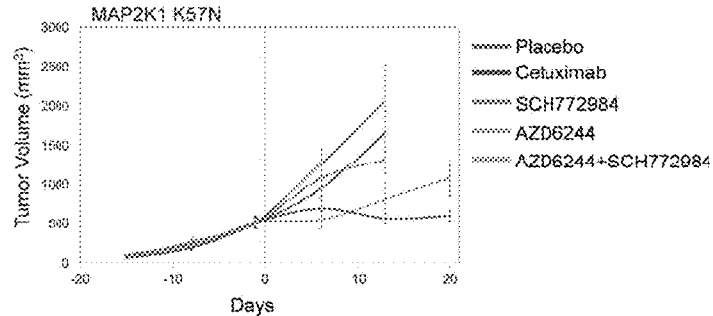

A similar approach was used to evaluate the EGFR small-molecule inhibitor afatinib in tumor CRC334 containing sequence change 843V>A in the protein kinase domain of EGFR (FIG. 5B). In this case, the mechanism of resistance to cetuximab could be through constitutive activation of the receptor kinase domain, abolishing dependence on extracellular signaling. We wondered whether afatinib could overcome cetuximab resistance as it has been shown to be effective primarily in EGFR mutant tumors. However, the resistant subclone containing the EGFR kinase domain alteration only affected 23% of the tumor cells in this sample which was highly tumor-enriched as measured by the prevalence of genetic alterations in highly mutated genes such as TP53 (present in 98% of the analyzed tumor). Given this heterogeneity, targeting the tumorgrafts with afatinib or cetuximab alone was not effective. In contrast, a combination of afatinib and cetuximab, presumably targeting both components of the tumor, resulted in marked and long lasting tumor growth inhibition (p<0.01, two-way ANOVA).

We also targeted resistance-conferring alterations in EGFR downstream effectors. Case CRC343 with MAP2K 157K>N substitution, encoding a mutant form of MEK1, was treated with small-molecule inhibitors against MEK1 (AZD6244) or against its direct substrate ERK (SCH772984). Similar to cetuximab, single-agent blockade of MEK1 was unproductive. However, inactivation of both MEK1 and ERK led to effective arrest of tumor growth (FIG. 5C) (p<0.01, two-way ANOVA). These results encourage concomitant targeting of MEK1 and ERK as a promising strategy to overcome aberrant MEK and potentially RAS signaling in CRC.

Figure 5D:
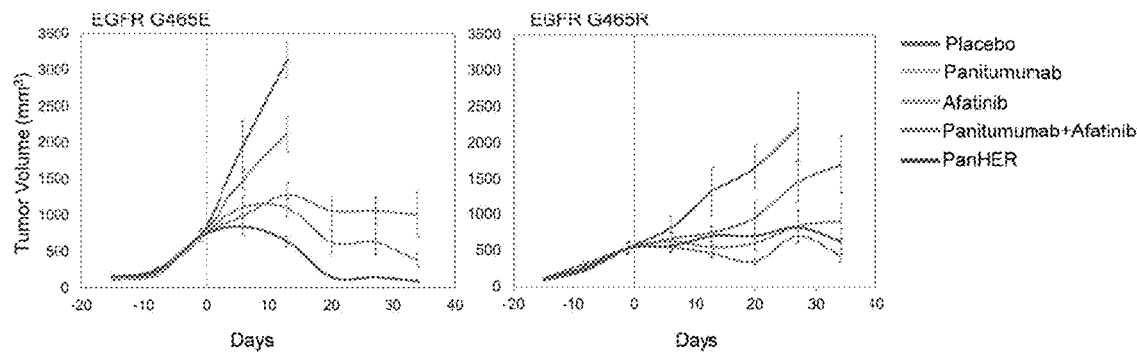

Next, we evaluated whether alternative therapeutic approaches may be helpful in tumors with acquired (secondary) cetuximab-resistant alterations in the EGFR ectodomain. As previous reports have shown that cetuximab-resistant tumors with 492S>R alterations in EGFR are sensitive to panitumumab (32), we wondered whether tumors with alterations at the structurally adjacent residue 465 in the ectodomain may also be sensitive to this therapy. Tumorgrafts derived from patient CRC104 with EGFR 465G>E mutation were randomized into independent treatment cohorts (n=6 for each arm) consisting of different anti-EGFR therapies or vehicle control. Unlike tumors with alterations at residue 492, the tumorgraft was poorly sensitive to panitumumab. Structural analyses indicate that S492 belongs solely to the cetuximab binding site within the large conformational epitopes of cetuximab and panitumumab in EGFR domain III. Conversely. G465 is located in the center of the region in which the epitopes of both antibodies overlap (55), suggesting that mutations affecting this codon may weaken antigen recognition by both therapies. This lack of sensitivity was not due to absence of EGFR dependence as kinase inhibition of EGFR using afatinib resulted in manifest reduction of tumor growth that could be further augmented by concomitant administration of panitumumab (p<0.01, two-way ANOVA), likely due to residual antibody activity (FIG. 5D).

We also explored whether EGFR inhibition by therapeutic antibodies targeting epitopes far from G465 could overcome resistance. We used Pan-HER (Symphogen), a monoclonal antibody mixture against several ERBB family members with an anti-EGFR component that binds epitopes different from those recognized by cetuximab and panitumumab (56) (FIG. S1). Notably, for this tumor Pan-HER was the most effective in inducing tumor regression (FIG. 5D) (p<0.01, two-way ANOVA), further suggesting that mutations in G465 do not affect the biological function of the receptor and are permissive for target blockade by antibodies that interact with other regions of the EGFR ectodomain. Similar results using the afatinib-panitumumab combination or Pan-HER were observed in CRC177 with EGFR 465G>R mutation (FIG. 5D).

Example 6

Materials and Methods

Specimen Obtained for Sequencing Analysis

The study population consisted of matched tumor and normal samples from 137 colorectal cancer patients that underwent surgical resection of liver metastases at the Candiolo Cancer Institute (Candiolo, Torino, Italy), the Mauriziano Umberto 1 Hospital (Torino) and the San Giovanni Battista Hospital (Torino) from 2008-2012. Informed consent for research use was obtained from all patients at the enrolling institution prior to tissue banking and study approval was obtained from the different centers. Tumors with KRAS alterations at codons 12, 13 and 61 that were detected using Sanger sequencing were not included in the study. From the resected tumor samples, tumorgraft models were established as described below. Following exome sequence analyses, 8 patients were detected to have KRAS mutations (patients CRC18, CRC58, CRC68, CRC237, CRC312, CRC328, CRC344, CRC382) and were excluded from further analyses.

Tumorgraft Model and In Vivo Treatments

Tissue from hepatic metastasectomy in affected individuals was fragmented and either frozen or prepared for implantation as described previously (1, 2). NOD/SCID (nonobese diabetic/severe combined immunodeficient) female mice (4 to 6 weeks old) were used for tumor implantation. Nucleic acids were isolated from early passaged tumorgrafts. The remaining tumorgraft material was further passaged and expanded. Animals (at least 6 mice per cohort) with established tumors defined as an average volume of 400 mm3 were treated with vehicle or drug regimens, either as a single-agent or in combination as indicated: cetuximab (Merck, White House Station, NJ) 20 mg/kg/twice-weekly i.p.; BGJ398 (*Sequoia* Research Products, Pangbourne, United Kingdom) 30 mg/kg/once-daily by oral gavage; panitumumab (Amgen, Thousand Oaks, CA), 20 mg/kg/twice-weekly i.p.; afatinib (*Sequoia* Research Products), 20 mg/kg/once-daily by oral gavage; AZD6244 (*Sequoia* Research Products), 25 mg/kg/once-daily by oral gavage: SCH772984 (ChemieTek, Indianapolis, IN), 75 mg/kg/once daily i.p.: Pan-HER (Symphogen), 60 mg/kg twice-weekly i.p. Each tumorgraft was evaluated at three and six weeks in 12 or 24 mice (depending on individual models) that were randomized to treatment and control arms at a 1:1 ratio. For assessment of tumor response to therapy, we used volume measurements normalized to the tumorgraft volume at the time of cetuximab treatment initiation. Tumorgrafts were classified as follows: (i) tumor regression with a decrease of at least 35% in tumor volume, (ii) disease progression with at least a 35% increase in tumor volume, and (iii) disease stabilization with a tumorgraft volume at levels <35% growth and <35% regression. Tumors displaying regression or stabilization continued treatment for additional 3 weeks. Tumor size was evaluated once per week by caliper measurements and the approximate volume of the mass was calculated. In vivo procedures and related biobanking data were managed using the Laboratory Assistant Suite (LAS), a web-based proprietary data management system for automated data tracking (3). All experiments were conducted with approval from the Animal Care Committee of the Candiolo Cancer Institute, in accordance with the Italian legislation on animal experimentation.

Massively Parallel Paired-End Sequencing and Somatic Mutation Identification

Sample library construction, exome or targeted capture, next generation sequencing, and bioinformatic analyses of tumor and normal samples were performed as previously described (4). In brief, fragmented genomic DNA from patient's tumor, tumorgraft developed from a liver metastasis or normal samples (adjacent non-cancerous liver or peripheral blood) was used for whole-exome enrichment or targeted regions using the Agilent SureSelect 50 Mb kit according to the manufacturer's instructions (Agilent, Santa Clara, CA). Captured DNA libraries were sequenced with Illumina HiSeq 2000 Genome Analyzer or a MiSeq System (Illumina, San Diego, CA). Sequence reads were analyzed and aligned to the human genome sequence (hg18) with the Eland v.2 algorithm in CASAVA 1.7 software (Illumina, San Diego, CA). Potential somatic mutations and copy number alterations were identified as described previously (4, 5). Mutations of interest were further visually inspected in tumor and normal sample sequences through using Integrative Genomics Viewer (IGV), version 2.3.23.

Gene Expression Analyses

Data were obtained using a HumanHT-12 v4 Illumina beadarray technology. Following data normalization, genes were collapsed to the probe displaying highest mean signal. Gene expression values were then Log 2-transformed and centered to the median. IRS2 expression in tumorgrafts scored as sensitive or resistant to cetuximab was compared by two-tailed Student's t-test.

Statistical Analyses for Genes with Somatic Alterations

Using the approach previously described in (6), we analyzed 24,334 somatic mutations (nonsynonymous and synonymous single base substitutions plus indels) identified in the protein coding sequence of 127 tumorgraft samples, after samples with KRAS hotspot mutations (codons 12 or 13) and those with a mutator phenotype were excluded. We implemented the following statistical framework to identify significantly mutated genes by incorporating background mutation rates, gene length, and base composition.

Inspired by previous works (7, 8), our model defines gene-specific background mutation rates, which capture exome-wide as well as gene-specific sequence-based parameters. We define 8 exhaustive and disjoint sequence-based dinucleotide contexts: C in CpG, G in CpG, C in TpC, G in GpA, and all other A, G, C, T. We represent the occurrences of each context in the entire protein coding sequence by $N_i$, and in each gene of interest by $g_i$. Subsequently, we identify, the dinucleotide context for all single base substitution (SBS) somatic mutations identified and derive the counts of mutations in each context over all CDS (protein coding sequence) ($n_i$). We derive the expected probability of observing a mutation in a base occurring in the CDS of a gene of interest as follows:

$$P_{mut} = \frac{\sum_{i=1}^{I} g_i f_i}{\sum_{i=1}^{I} g_i} \quad (1)$$

$$f_i = \frac{n_i}{N_i} \quad (2)$$

where $f_i$ denotes the fraction of bases in dinucleotide context i in the entire CDS, where a mutation has been observed. The context parameters $N_i$ and $g_i$ are defined as the total number of occurrences of each context sequenced across all of the samples, therefore following the simplifying assumption of full coverage of the entire protein coding sequence, and assuming K samples total, these parameters will be K times those of a single haploid exome.

Following the definition of $f_i$, we derive the background probability of observing at least $m_{g,obs}$ mutations in a gene of interest, using the binomial tail probability of $L_g$ trials with $m_{g,obs}$ successes and $P_{mut}$ probability of success in each trial. Here, $L_g$ represents the length of the CDS of the gene times the number of samples.

$$P_{freq}^{mut} = P(m_{g,mut} \geq m_{g,obs}) = \sum_{j=m_{g,obs}}^{L_g} \binom{L_g}{j} P_{mut}^j (1-P_{mut})^{L_g-j} \quad (3)$$

We use an equivalent formulation to model the statistical significance of observing $g_{g,obs}$ insertions/deletions (indels) in a gene of interest. The background indel frequency ($P_{indel}$) is defined as the number of indels recovered in the entire CDS of the sequenced samples divided by the length of the entire CDS available in these samples.

$$P_{freq}^{indel} = P(q_{g,indel} \geq q_{g,obs}) = \sum_{j=q_{g,obs}}^{L_g} \binom{L_g}{j} P_{indel}^j (1-P_{indel})^{L_g-j} \quad (4)$$

The two statistical tests described above (3, 4) reflect the significance of mutation counts in a gene, but are blind to the protein-level consequence of mutations. To capture the impact of mutation on protein, we apply an extension of the tests above that examines enrichment for nonsynonymous mutations in the set of single base substitution mutations identified in a gene of interest. We define a background, gene-specific ratio of non-synonymous to synonymous (NS/S) mutations, given the exome-wide NS/S ratio in each dinucleotide context ($r_i$) and the sequence composition of each gene as follows. Note that $g_i$ has the same definition as in (1).

$$r_g = \frac{\sum_{i=1}^{I} r_i g_i}{\sum_{i=1}^{I} g_i} \quad (5)$$

Given the NS/S ratio for a gene of interest, the probability of an observed mutation in the gene being nonsynonymous is:

$$P_{g,NS} = \frac{r_g}{r_g + 1} \quad (6)$$

Following this step, the binomial tail probability of observing $m_{g,obs}^{NS}$ from the total of $m_{g,obs}$ mutations in a gene of interest is:

$$P_{composition}^{mut} = \quad (7)$$
$$p(m_{g,mut}^{NS} \geq m_{g,obs}^{NS}) = \sum_{j=m_{g,obs}^{NS}}^{m_{g,obs}} \binom{m_{g,obs}}{j} P_{g,NS}^j (1-P_{g,NS})^{m_{g,obs}-j}$$

The three test statistics (3, 4, 7) rely on three distinct measures for calling a gene significantly mutated: the counts of single base substitutions, the counts of indels, and the relative counts of non-synonymous to synonymous single base substitutions. Assuming the independence of these measures, given gene-specific parameters of $g_i$ and $L_g$, we combine them using Fisher's combined probability test to derive a measure of overall significance for each gene of interest (combined p-value). We acknowledge the fact that Fisher's combined probability test is best suited to p-values derived from continuous probability distribution functions; however, it has been shown that its application to p-values derived from discrete probability distributions results in conservative estimates of p-value.

Finally, we apply Bonferroni and Benjamini-Hochberg's correction method to combined p-values to control for multiple testing.

Statistical Analyses for Therapeutic Resistance or Sensitivity

Statistical models for tumor growth were implemented for each of four mutation profiles that were correlated to resistance or sensitivity to cetuximab treatment. Group A samples had ERBB2 mutations and/or amplification. MET amplification, EGFR mutations affecting the ectodomain or kinase domain, NRAS mutation, BRAF 600V>E, FGFR1 amplification, PDGFRA mutations affecting the kinase domain and MAP2K1 57K>N. Group B samples had ERBB2 mutations, EGFR mutations affecting the ectodomain or kinase domain, FGFR1 amplification, PDGFRA mutations affecting the kinase domain or MAP2K1 57K>N. Group C samples had amplification of EGFR or a mutation or amplification of IRS2 while group D samples had amplification or mutation of IRS2. As IRS2 alterations are likely to be predictive of anti-EGFR response in cases without other mechanisms of resistance to EGFR therapy, we excluded two samples that harbored a MET amplification or BRAF mutation from Group C and D. For each group, Wilcoxon rank sum and two sample Welch t-tests were used to evaluate differences in the mean tumor growth between samples with mutation and those without. For preclinical models, statistical comparisons of treatment efficacy in were performed by two-way ANOVA.

Protein Structure Modeling

The crystal structure of the extracellular domain of the epidermal growth factor receptor in complex with the Fab fragment of cetuximab was retrieved from the protein data bank (PDB entry #IYY9). This PDB entry contains a complex of 3 biomacromolecules including the extracellular portion of EGFR, cetuximab Fab Light chain, and cetuximab Fab Heavy chain. The EGFR-cetuximab complex was visualized using Deep View Swiss-pdbviewer (SPDBV_4.10_PC).

References (for Example 6 Only) Incorporated by Reference Here

1. F. Galimi et al., Genetic and expression analysis of MET, MACC1, and HGF in metastatic colorectal cancer: response to met inhibition in patient xenografts and pathologic correlations. Clin Cancer Res 17, 3146 (May 15, 2011).
2. A. Bertotti et al., A molecularly annotated platform of patient-derived xenografts ("xenopatients") identifies HER2 as an effective therapeutic target in cetuximab-resistant colorectal cancer. Cancer discovery 1, 508 (November, 2011).
3. E. Baralis, A. Bertotti, A. Fiori, A. Grand, LAS: a software platform to support oncological data management. Journal of medical systems 36 Suppl 1, S81 (November, 2012).
4. M. Sausen et al., Integrated genomic analyses identify ARID1A and ARID1B alterations in the childhood cancer neuroblastoma. Nat Genet 45, 12 (January, 2013).
5. S. Jones et al., Core signaling pathways in human pancreatic cancers revealed by global genomic analyses. Science 321, 1801 (Sep. 26, 2008).
6. Y. Jiao et al., Exome sequencing identifies frequent inactivating mutations in BAP1, ARID1A and PBRM1 in intrahepatic cholangiocarcinomas. Nat Genet 45, 1470 (December, 2013).

7. T. Sjoblom et al., The consensus coding sequences of human breast and colorectal cancers. *Science* 314, 268 (Oct. 13, 2006).
8. Z. Kan et al., Diverse somatic mutation patterns and pathway alterations in human cancers. *Nature* 466, 869 (Aug. 12, 2010).
9. K. Koefoed et al., Rational identification of an optimal antibody mixture for targeting the epidermal growth factor receptor. mAbs 3, 584 (November-December, 2011).
10. C. Montagut et al., Identification of a mutation in the extracellular domain of the Epidermal Growth Factor Receptor conferring cetuximab resistance in colorectal cancer. *Nat Med* 18, 221 (February, 2012).

References

The disclosure of each reference cited is expressly incorporated herein.

1. G. Joslyn et al., Identification of deletion mutations and three new genes at the familial polyposis locus. *Cell* 66, 601 (1991).
2. J. Groden et al., Identification and characterization of the familial adenomatous polyposis coli gene. *Cell* 66, 589 (1991).
3. K. W. Kinzler et al., Identification of a gene located at chromosome 5q21 that is mutated in colorectal cancers. *Science* 251, 1366 (1991).
4. J. L. Bos et al., Prevalence of ras gene mutations in human colorectal cancers. *Nature* 327,293 (1987).
5. H. Davies et al., Mutations of the BRAF gene in human cancer. *Nature*, (Jun. 9, 2002).
6. H. Rajagopalan et al., Tumorigenesis: RAF/RAS oncogenes and mismatch-repair status. *Nature* 418, 934. (2002).
7. Y. Samuels et al., High frequency of mutations of the PIK3CA gene in human cancers. *Science* 304, 554 (Apr. 23, 2004).
8. M. Keniry, R. Parsons, The role of PTEN signaling perturbations in cancer and in targeted therapy. *Oncogene* 27, 5477 (Sep. 18, 2008).
9. S. A. Hahn et al., Dpc4, a Candidate Tumor Suppressor Gene At Human Chromosome 18q21.1. *Science* 271, 350 (1996).
10. S. Thiagalingam, Evaluation of Chromosome 18q in Colorectal Cancers. *Nature Genetics* 13, 343 (1996).
11. E. Montgomery et al., Nuclear localization of Dpc4 (Madh4, Smad4) in colorectal carcinomas and relation to mismatch repair/transforming growth factor-beta receptor defects. *Am J Pathol* 158, 537 (2001).
12. S. J. Baker et al., Chromosome 17 deletions and p53 gene mutations in colorectal carcinomas. *Science* 244, 217 (Apr. 14, 1989).
13. S. J. Baker, S. Markowitz, E. R. Fearon, J. K. Willson, B. Vogelstein, Suppression of human colorectal carcinoma cell growth by wild-type p53. *Science* 249, 912 (1990).
14. N. Rampino et al., Somatic frameshift mutations in the BAX gene in colon cancers of the microsatellite mutator phenotype. *Science* 275, 967 (1997).
15. A. Bardelli et al., Mutational analysis of the tyrosine kinome in colorectal cancers. *Science* 300, 949 (May 9, 2003).
16. Z. Wang et al., Mutational analysis of the tyrosine phosphatome in colorectal cancers. *Science* 304, 1164 (May 21, 2004).
17. D. W. Parsons et al., Colorectal cancer: mutations in a signalling pathway. *Nature* 436, 792 (Aug. 11, 2005).
18. T. Sjoblom et al., The consensus coding sequences of human breast and colorectal cancers. *Science* 314, 268 (Oct. 13, 2006).
19. L. D. Wood et al., The genomic landscapes of human breast and colorectal cancers. *Science* 318, 1108 (Nov. 16, 2007).
20. N. Cancer Genome Atlas, Comprehensive molecular characterization of human colon and rectal cancer. *Nature* 487, 330 (Jul. 19, 2012).
21. E. Van Cutsem, A. Cervantes. B. Nordlinger, D. Arnold, E. G. W. G. on behalf of the, Metastatic colorectal cancer: ESMO Clinical Practice Guidelines for diagnosis, treatment and follow-updagger. *Annals of oncology: official journal of the European Society for Medical Oncology/ESMO*, (Sep. 4, 2014).
22. L. A. Diaz, Jr. et al., The molecular evolution of acquired resistance to targeted EGFR blockade in colorectal cancers. *Nature* 486, 537 (Jun. 28, 2012).
23. S. Misale et al., Emergence of KRAS mutations and acquired resistance to anti-EGFR therapy in colorectal cancer. *Nature* 486, 532 (Jun. 28, 2012).
24. R G. Amado et al., Wild-type KRAS is required for panitumumab efficacy in patients with metastatic colorectal cancer. *J Clin Oncol* 26, 1626 (Apr. 1, 2008).
25. W. De Roock et al., Effects of KRAS, BRAF, NRAS, and PIK3CA mutations on the efficacy of cetuximab plus chemotherapy in chemotherapy-refractory metastatic colorectal cancer: a retrospective consortium analysis. *Lancet Oncol* 11, 753 (August, 2010).
26. C. Mao et al., BRAF V600E mutation and resistance to anti-EGFR monoclonal antibodies in patients with metastatic colorectal cancer: a meta-analysis. *Molecular biology reports* 38, 2219 (April, 2011).
27. J. Tol et al., Markers for EGFR pathway activation as predictor of outcome in metastatic colorectal cancer patients treated with or without cetuximab. *Eur J Cancer* 46, 1997 (July, 2010).
28. A. Sartore-Bianchi et al., PIK3CA mutations in colorectal cancer are associated with clinical resistance to EGFR-targeted monoclonal antibodies. *Cancer Res* 69, 1851 (Mar. 1, 2009).
29. A. Bardelli et al., Amplification of the MET receptor drives resistance to anti-EGFR therapies in colorectal cancer. *Cancer discovery* 3, 658 (June, 2013).
30. A. Bertotti et al., A molecularly annotated platform of patient-derived xenografts ("xenopatients") identifies HER2 as an effective therapeutic target in cetuximab-resistant colorectal cancer. *Cancer discovery* 1, 508 (November, 2011).
31. K. Yonesaka et al., Activation of ERBB2 signaling causes resistance to the EGFR-directed therapeutic antibody cetuximab. *Sci Transl Med* 3, 99ra86 (Sep. 7, 2011).
32. C. Montagut et al, Identification of a mutation in the extracellular domain of the Epidermal Growth Factor Receptor conferring cetuximab resistance in colorectal cancer. *Nat Med* 18, 221 (February, 2012).
33. C. Bettegowda el al., Detection of circulating tumor DNA in early- and late-stage human malignancies. *Sci Transl Med* 6, 224ra24 (Feb. 19, 2014).
34. L. A. Diaz, Jr., M. Sausen, G. A. Fisher, V. E. Velculescu, Insights into therapeutic resistance from whole-genome analyses of circulating tumor DNA. *Oncotarget* 4, 1856 (October, 2013).
35. B. O. Van Emburgh, A. Sartore-Bianchi, F. Di Nicolantonio, S. Siena, A. Bardelli, Acquired resistance to EGFR-targeted therapies in colorectal cancer. *Mol Oncol*, (May 14, 2014).

36. See supporting materials.
37. R. J. Leary et al., Integrated analysis of homozygous deletions, focal amplifications, and sequence alterations in breast and colorectal cancers. *Proc Natl Acad Sci USA* 105, 16224 (Oct. 21, 2008).
38. G. Perkins, C. Pilati, H. Blons, P. Laurent-Puig, Beyond KRAS status and response to anti-EGFR therapy in metastatic colorectal cancer. *Pharmacogenomics* 15, 1043 (May, 2014).
39. P. Stephens et al., Lung cancer: intragenic ERBB2 kinase mutations in tumours. *Nature* 431, 525 (Sep. 30, 2004).
40. R. Bose et al., Activating HER2 mutations in HER2 gene amplification negative breast cancer. *Cancer discovery* 3, 224 (February, 2013).
41. T. D. Barber, B. Vogelstein, K. W. Kinzler, V. E. Velculescu, Somatic mutations of EGFR in colorectal cancers and glioblastomas. *N Engl J Med* 351, 2883 (Dec. 30, 2004).
42. M. Moroni et al., Somatic mutation of EGFR catalytic domain and treatment with gefitinib in colorectal cancer. *Annals of oncology: official journal of the European Society for Medical Oncology/ESMO* 16, 1848 (November 2005).
43. J. Wesche, K. Haglund, E. M. Haugsten, Fibroblast growth factors and their receptors in cancer. *Biochem J* 437, 199 (Jul. 15, 2011).
44. J. Weiss et al., Frequent and focal FGFR1 amplification associates with therapeutically tractable FGFR1 dependency in squamous cell lung cancer. *Sci Transl Med* 2, 62ra93 (Dec. 15, 2010).
45. R M. Neve et al., A collection of breast cancer cell lines for the study of functionally distinct cancer subtypes. *Cancer Cell* 10, 515 (December, 2006).
46. F. Goke et al., Fibroblast growth factor receptor 1 as a putative therapy target in colorectal cancer. *Digestion* 88, 172 (2013).
47. M. C. Heinrich et al., PDGFRA activating mutations in gastrointestinal stromal tumors. *Science* 299, 708 (Jan. 31, 2003).
48. N. J. Dibb, S. M. Dilworth, C. D. Mol, Switching on kinases: oncogenic activation of BRAF and the PDGFR family. *Nat Rev Cancer* 4, 718 (September, 2004).
49. J. L. Marks et al., Novel MEK1 mutation identified by mutational analysis of epidermal growth factor receptor signaling pathway genes in lung adenocarcinoma. *Cancer Res* 68, 5524 (Jul. 15, 2008).
50. A. K. Murugan, J. Dong, J. Xie, M. Xing, MEK1 mutations, but not ERK2 mutations, occur in melanomas and colon carcinomas, but none in thyroid carcinomas. *Cell Cycle* 8, 2122 (Jul. 1, 2009).
51. M. Moroni et al., Gene copy number for epidermal growth factor receptor (EGFR) and clinical response to antiEGFR treatment in colorectal cancer: a cohort study. *Lancet Oncol* 6, 279 (May, 2005).
52. A. Algars, M. Lintunen, O. Carpen, R. Ristamaki, J. Sundstrom. EGFR gene copy number assessment from areas with highest EGFR expression predicts response to anti-EGFR therapy in colorectal cancer. *Br J Cancer* 105, 255 (Jul. 12, 2011).
53. E. Day et al., IRS2 is a candidate driver oncogene on 13q34 in colorectal cancer. *International journal of experimental pathology* 94, 203 (June, 2013).
54. V. Guagnano et al., Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase. *Journal of medicinal chemistry* 54, 7066 (Oct. 27, 2011).
55. M. Voigt et al., Functional dissection of the epidermal growth factor receptor epitopes targeted by panitumumab and cetuximab. *Neoplasia* 14, 1023 (November, 2012).
56. K. Koefoed et al., Rational identification of an optimal antibody mixture for targeting the epidermal growth factor receptor. *mAbs* 3, 584 (November-December, 2011).
57. S. Misale et al., Blockade of EGFR and MEK intercepts heterogeneous mechanisms of acquired resistance to anti-EGFR therapies in colorectal cancer. *Sci Transl Med* 6, 224ra26 (Feb. 19, 2014).
58. C. S. Karapetis et al., K-ras mutations and benefit from cetuximab in advanced colorectal cancer. *N Engl J Med* 359, 1757 (Oct. 23, 2008).
59. R. K. Dearth, X. Cui, H. J. Kim, D. L. Hadsell, A. V. Lee, Oncogenic transformation by the signaling adaptor proteins insulin receptor substrate (IRS)-1 and IRS-2. *Cell Cycle* 6, 705 (Mar. 15, 2007).
60. T. Fujioka et al., Further evidence for the involvement of insulin receptor substrates in epidermal growth factor-induced activation of phosphatidylinositol 3-kinase. *European journal of biochemistry/FEBS* 268, 4158 (August, 2001).
61. A. Pavlicek et al., Molecular predictors of sensitivity to the insulin-like growth factor 1 receptor inhibitor Figitumumab (CP-751,871). *Mol Cancer Ther* 12, 2929 (December, 2013).
62. E. Garralda et al., Integrated next-generation sequencing and avatar mouse models for personalized cancer treatment. *Clin Cancer Res* 20, 2476 (May 1, 2014).

The invention claimed is:

1. A method of treating a colorectal tumor in a human, wherein the colorectal tumor is resistant to EGFR blockade and comprises an FGFR1 amplification, the method comprising:

administering to the human BGJ398 and cetuximab.

2. The method of claim 1 wherein prior to the step of administering, a sample from the tumor is tested and amplification of FGFR1 is determined.

* * * * *